(12) United States Patent
Tryggvason et al.

(10) Patent No.: US 6,955,924 B2
(45) Date of Patent: Oct. 18, 2005

(54) LAMININ CHAINS: DIAGNOSTIC USES

(75) Inventors: Karl Tryggvason, Oulu (FI); Pekka Kallunki, La Jolla, CA (US); Charles Pyke, Hilleroo (DK)

(73) Assignee: BioStratum, Inc., Durham, NC (US)

( * ) Notice: Subject to any disclaimer, the term of this patent is extended or adjusted under 35 U.S.C. 154(b) by 0 days.

(21) Appl. No.: 09/756,071

(22) Filed: Jan. 8, 2001

(65) Prior Publication Data

US 2002/0052307 A1 May 2, 2002

Related U.S. Application Data

(60) Continuation-in-part of application No. 09/663,147, filed on Sep. 15, 2000, which is a continuation of application No. 08/800,593, filed on Feb. 18, 1997, now Pat. No. 6,143,505, which is a division of application No. 08/317,450, filed on Oct. 4, 1994, now Pat. No. 5,660,982.
(60) Provisional application No. 60/175,005, filed on Jan. 7, 2000.

(51) Int. Cl.[7] .................. A61K 33/00; C07K 14/78; C12N 5/10; C12Q 1/02; G01N 33/53

(52) U.S. Cl. ................. 436/514; 435/1.49; 435/7.1; 435/7.2; 435/7.8; 435/9.34; 435/29; 435/40.51; 435/40.52; 435/325; 435/326; 435/330; 435/332; 435/344.1; 435/371; 435/375; 435/173.9; 424/574

(58) Field of Search .................. 424/9.1, 9.2, 9.34, 424/141.1, 155; 435/723; 436/64, 506, 512, 547, 548; 530/387.7, 828

(56) References Cited

U.S. PATENT DOCUMENTS 6,294,356 B1 9/2001 Jones et al.

FOREIGN PATENT DOCUMENTS

| WO | WO 00/26342 | 5/2000 |
| WO | WO 00/34441 | 6/2000 |
| WO | WO 01/87239 | 11/2001 |

OTHER PUBLICATIONS

Giannelli et al. 1997. Science. vol. 277: 225–228.*
Seaver. 1994. Genetic Engineering. 14(14):10 and 21.*
Aberdam et al., (1994), Nature Genetics, "Herlitz's junctional epidermolysis bullosa is linked to mutations in the gene (LAMC2) for the γ2 subunit of nicein/kalinin (LAMANIN-5)", vol: 6: pp. 299–304.
Amano, et al., (2000), The Journal of Biological Chemistry, "Bone morphogenetic protein 1 is an extracellular processing enzyme of the laminin 5 γ2 chain", vol: 275(30), pp. 22728–22735.
Anderson, et al., (2001), The Laryngoscope, "Tumor deposition of laminin-5 and the relationship with perineural invasion", vol: 111, pp. 2140–2143.
Calaluce, et al., (2001), Molecular Carcinogenesis, "Laminin-5-mediated gene expression in human prostate carcinoma cells", vol: 30, pp. 119–129.
Davis, et al., (2001), The Prostate, "Unique expression pattern of the α6β4 integrin and Laminin-5 in human prostate carcinoma", vol: 46, pp. 240–248.
Engvall, et al., (1990), Cell Regulation, "Distribution and isolateion of four laminin variants; tissue restricted distribution of heterotrimers assembled from five subunits", vol: 1, pp. 731–740.

(Continued)

Primary Examiner—Lynette R. F. Smith
Assistant Examiner—Ja-Na Hines
(74) Attorney, Agent, or Firm—McDonnell Boehnen Hulbert & Berghoff

(57) ABSTRACT

The instant invention provides for the identification, diagnosis, monitoring, and treatment of invasive cells using the laminin 5 gamma-2 chain protein or nucleic acid sequence, or antibodies thereto.

6 Claims, 14 Drawing Sheets

OTHER PUBLICATIONS

Fukushima, et al., (2001), Mod. Pathol., "Expression of laminin–5–γ–2 chain in intraductal papillary–mucinous and invasive ductal tumors of the pancreas", vol: 14(5), pp. 404–409.

Gianelli, et al., (1997), Science, "Induction of Cell Migration by Matrix Metalloprotease–2 Cleavage of Laminin–5", vol: 277, pp. 225–228.

Gianelli and Antonaci, (2001), Clinical and Experimental Metastasis, "Biological and Clinical Relevance of Laminin–5 in Cancer", vol: 18, 439–443.

Goldfinger, et al., (1998), J. Cell Biol., "Processing of Laminin–5 and its functional consequences: Role of Plasmin and Tissue–type Plaminogen Activator", vol: 141, pp. 255–265.

Gonzales, et al., (1999), Mol. Biol. of the Cell, "A cell signal pathway involving laminin–5, α3β1 integrin, and mitogen–activated protein kinase can regulate epithelial cell proliferation", vol: 10, pp. 259–270.

Grassi, et al., (1999), Journal of Cell Science, "The SFL activity secreted by metastatic carcinoma cells is related to laminin 5 and mediates cell scattering in an integrin–independent manner", vol: 112, pp. 2511–2520.

Haas, et al., (2001), The Journal of Histochemistry & Cytochemistry, "A comparative quantitative analysis of laminin–5 in the basement membrane of normal, hyperplastic, and malignant oral mucosa by confocal immunofluorescence imaging", vol: 49(10), pp. 1261–1268.

Habermann, et al., (2001), Scand J. Gastroenterol, "Ulcerative colitis and colorectal carcinoma", vol: 7, pp. 751–758.

Hao, et al., (1996), American Journal of Pathology, "Differential expression of laminin 5 (α3β3γ2) by human malignant and normal prostate", vol: 149(4):, pp. 1341–1349.

Heagerty, et al., (1986), Lancet, "GB3 monoclonal antibody for diagnosis of junctional epidermolysis bullosa", vol: 860, p. 8485.

Heagerty, et al., (1987), British J. Dermatol, "Raid prenatal diagnosis of epidermolysis bullosa letalis using GB3 monoclonal antibody", vol: 17, pp. 271–275.

Hellman, et al., (2000), Int. J. Gynecol. Cancer., "Cancer of the vagina: Laminin–5γ2 chain expression and prognosis", vol: 10, pp. 391–396.

Henning, et al., (1999), Histopathology, "Loss of laminin–5 in the epithelium–stroma interface: an immunohistochemical marker of malignancy in epithelial lesions of the breast", vol: 34, pp. 305–309.

Hlubek, et al., (2001), Cancer Research, "Expression of the invasion factor laminin γ2 in colorectal carcinomas is regulated by β–catenin[1]", vol: 61, pp. 8089–8093.

Hsi, et al., (1986), J. Reprod. Immunology, "Monoclonal antibodies to human amnion", vol: 9, pp. 11–21.

Kagesato, et al., (2001), Japan J. Cancer Research, "Sole expression of laminin γ2 chain in invading tumor cells and its associateion with stromal fibrosis in lung adenocarcinomas", vol: 21, pp. 184–192.

Katoh, et al., (2002), Oncology, Correlation between laminin–5 γ2 chain expression and epidermal growth factor receptor expression and its clinicopathological significance in squamous cell carcinoma of the tongue, vol: 62, pp. 318–326.

Kallunki, et al., (1992), J. Cell Biol., "A truncated laminin chain homologous to the B2 chain: Structuree, spatial expression, and chromosomal assignment", vol: 118, pp. 679–693.

Koshikawa, et al., (1999), Cancer Research, Overexpression of laminin γ2 chain monomer in invading gastric carcinoma cells, vol: 59, pp. 5596–5601.

Lenander, et al., (2001), Analytical Cellular Pathology, "Laminin–5 γ2 chain expression correlates with unfavorable prognosis in colon carcinomas", vol: 22, pp. 201–209.

Lohi, et al., (2000), APMIS, "Basement membrane laminin–5 is deposited in colorectal adenomas and carcinomas and serves as a ligand for α3β1 integrin", vol: 108, pp. 161–172.

Lugassy, et al., (1999), J. Cutaneuous Pathol., "Tumor microvessels in melanoma express the beta–2 chain of laminin. Implications for melanoma metastasis", vol: 26, pp. 222–226.

Määttä, et al., (2001), The Journal of Histochemistry & Cytochemistry, "Comparative analysis of the distribution of laminin chains in the basement membranes in some malignant epithelial tumors: the α1 chain of laminin shows a selected expression pattern in human carcinomas", vol: 49(6), pp. 711–725.

Määttä, et al., (1999), Journal of Pathology, "Expression of the laminin γ2 chain in different histological types of lung carcinoma. A study by immunohistochemistry and in situ hybridization", vol: 188, pp. 361–368.

Manda, et al., (2000), Biochemical and Biophysical Research Communications, "Differential expression of the LAMB3 and LAMC2 genes between small cell and non–small cell lung carcinomas", vol: 275, pp. 440–445.

Marinkovich, et al., (1992), JBC, "The anchoring filament protein kalinin is synthesized and secreted as a high molecular weight precursor", vol: 267, pp. 17900–17906.

Martin, et al., (1998), Mol. Med., "Down–regulation of laminin–5 in breast carcinoma cells", vol: 4(9), pp. 601–613.

Matsui, et al., (1995), J. Invest. Dermatology, "γ2 chain of Laminin–5 is recognized by Monoclonal Antibody GB3", vol: 105, pp. 648–652.

Matsui, et al., (1995), JBC, "The Assembly of Laminin–5 Subunits", vol: 270(40), pp. 23496–23503.

McMillan, et al., (1997), Br. J. Dermatol., "Immunohistochemical analysis of the skin in junctional epidermolysis bullosa using laminin 5 chain specific antibodies is of limited value in predicting the underlying gene mutation", vol: 136, pp. 817–822.

Mizushima, et al., (1998), Horm. Res., "Wide Distribution of Laminin–5 γchain in basement membranes of various human tissues", vol: 50 (Suppl. 2), pp. 7–14.

Mizushima, et al., (1996), J. Biochem., "Differential expression of laminin–5/ladsin subunits in human tissues and cancer cell lines and their induction by tumor promoter and growth factors", vol: 120, pp. 1196–1202.

Moriya, et al., (2001), Cancer, "Increased expression of laminin–5 and its prognostic significance in lung adenocarcinomas of small size", vol: 19(6), pp. 1129–1141.

Niki, et al., (2002), American Journal of Pathology, "Frequent co–localization of cox–2 and laminin–5 γ2 chain at the invasive front of early–stage lung adenocarcinomas", vol: 160(3), pp. 1129–1130.

Nordemar, et al., (2001), Anticancer Research, "Laminin–5 as a predictor of invasiveness in cancer in situ lesions of the larynx", vol: 21, pp. 509–512.

Nordstrom, et al., (2002), Int. J. Gynecol., "Laminin–5 γ2 chain as an invasivity marker for uni–and multifocal lesions in the lower anogenital tract", vol: 12, pp. 105–109.

Ono, et al., (2002), Cancer Letters, "Epidermal growth fctor receptor gene amplification is correlated with laminin–5 γ2 chain expression in oral squamous cell carcinoma cell lines", vol: 175, pp. 197–204.

Patarroyo, et al., (2000), Cancer Biology, "Laminin isoforms in tumor invasion, angiogenesis and metastasis", vol: 12, pp. 197–207.

Patel, et al., (2000), Int. J. Cancer, "Laminin–γ2 overexpression in head–and–neck squamous cell carcinoma", vol: 99, pp. 583–588.

Pyke, et al., (1994), American Journal, "The γ2 chain of kalinin/laminin 5 is preferentially expressed in invading malignant cells in human cancers", vol: 145(4), pp. 782–791.

Pyke, et al., (1995), Cancer Research, "Laminin–5 is a marker of invading cancer cells in some human carcinomas and is coexpressed with the receptor for urokinase plasminogen activator in budding cancer cells in colon adenocarcinomas", vol: 55(18), pp. 4132–4139.

Rouselle, et al., (1991), J. Cell Biol., "Kalinin: an epithelium–specific basement membrane adhesion molecule that is a component of anchoring filaments", vol: 114(3), pp. 567–576.

Rouselle, et al., (1994), J. Cell Biol., "Kalinin is more efficient than laminin in promoting adhesion of primary keratinocytes and some other epithelial cells and has a different requirement ofr integrin receptors", vol: 125, pp. 205–214.

Salo, et al., (1999), Matrix Biol., "Laminin–5 promotes adhesion and migration of epithelial cells: identification of a migration–related element in the γ2 chain gene (LAMC2) with activity in transgenic mice", vol: 18, pp. 197–210.

Salo, et al., (1999), Acta Univ. Oul.D 540, "Laminin–5: Function of the γ2 chain in epithelial cell adhesion and migration, and expression in epithelial cells and carcinomas" Doctoral Dissertation.

Seftor, et al., (2001), Cancer Research, "Cooperative interactions of laminin 5 γ2 chain, matrix metalloproteinase–2 and membrane type–1–matrix/metalloproteinase are required for mimicry of embryonic vasculogenesis by aggressive melanoma", vol: 61, pp. 6322–6327.

Skyldberg, et al., (1999), Journal of the National Cancer Institute, "Laminin–5 as a marker of invasiveness in cervical lesions", vol: 91(21), pp. 1882–1887.

Soini, et al., (1996), Journal of Pathology, "Expression of the laminin γ2 chain in pancreatic adenocarcinoma", vol: 180, pp. 290–294.

Sordat, et al., (1998), J. Pathol., "Differential expression of lamini–5 subunits and integrin receptors in human colorectal neoplasia"vol: 185, pp. 44–52.

Sordat, et al., (2000), Int. J. Cancer., "Tumor cell budding and Laminin–5 expression in colorectal carcinoma can be modulated by the tissue micro–environment", vol: 88, pp. 708–717.

Takahashi, et al., (2002), Cancer, Cytoplasmic Expression of Laminin γ2 Chain Correlates with Postoperative Hepatic Metastasis and Poor Prognosis in Patient with Pancreatic Ductal Adenocarcinoma, vol: 94(6), pp. 1894–1901.

Tani, et al., (1997), American Journal of Pathology, "Pancreatic carcinomas deposit laminin–5 preferably adhere to laminin–5 and migrate on the newly deposited basement membrane", vol: 151(5), pp. 1289–1302.

Tsuji, et al., (2002), Clinical & Experimental Metastasis, Regulation of melanoma cell migration and invasion by laminin–5 and α3β1 integrin (VLA–3), vol: 19, 127–134.

Tunggal, et al., (2002), American Journal of Pathology, "Defective laminin 5 processing in cylindroma cells", vol: 160(2), pp. 459–468.

Vailly, et al., (1994), Eur. J. Biochem., "The 100–kDa chain of nicein/kalinin is a laminin B2 chain variant", vol: 219, pp. 209–218.

Verrando, et al., (1987), Exp. Cell Res., "Monoclonal antibody GB3, a new probe for the study of human basement membranes and hemidesmosomes"vol: 170, p. 116–128.

Verrando, et al, (1991), Lab. Investigation, "Monoclonal antibody GB3 defines a widespread defect of several basement membranes and a keratinocyte dysfunction in patients with lethal junctional 4perdermolysis bullosa", vol: 64, pp. 85–92.

Yamamoto, et al., (2001), Clinical Cancer Research, "Expression of the γ2 chain of Laminin–5 at the invasive front is associated with recurrence and poor prognosis in human esophageal squamous cell carcinoma", vol: 7, pp. 896–900.

* cited by examiner

FIG 4A (SEQ ID NO.:12 & 13)

```
   1 gaccacctga tcgaaggaaa aggaaggcac agcggagcgc agagtgagaa ccaccaaccg
  61 aggcgccggg cagcgacccc tgcagcggag acagagactg agcggccggg caccgccatg
   1                                                                 M
 121 cctgcgctct ggctgggctg ctgcctctgc ttctcgctcc tcctgccggc agcccgggcc
   2  P  A  L   W  L  G  C   C  L  C   F  S  L   L  L  P  A   A  R  A
 181 acctccagga gggaagtctg tgattgcaat gggaagtcca ggcagtgtat ctttgatcgg
  22  T  S  R   R  E  V  C   D  C  N   G  K  S   R  Q  C  I   F  D  R
                                 ↦ Domain V
 241 gaacttcaca gacaaactgg taatggattc cgctgcctca actgaatga caacactgat
  42  E  L  H   R  Q  T  G   N  F  R  C  L  N  C  N  D  N  T  D
 301 ggcattcact gcgagaagtg caagaatggc ttttaccggc acagagaaag ggaccgctgt
  62  G  I  H   C  E  K  C   K  N  G   F  Y  R   H  R  E  R   D  R  C
 361 ttgccctgca attgtaactc aaaggttct cttagtgctc gatgtgacaa ctctggacgg
  82  L  P  C   N  C  N  S   K  G   S   L  S  A   R  C  D  N   S  G  R
 421 tgcagctgta aaccaggtgt gacaggagcc agatgcgacc gatgtctgcc aggcttccac
 102  C  S  C   K  P  G  V   T  G  A   R  C  D   R  C  L  P   G  F  H
 481 atgctcacgg atgcggggtg cacccaagac cagagactgc tagactccaa gtgtgactgt
 122  M  L  T   D  A  G  C   T  Q  D   Q  R  L   L  D  S  K   C  D  C
 541 gacccagctg gcatcgcagg gccctgtgac gcgggccgct gtgtctgcaa gccagctgtt
 142  D  P  A   G  I  A  G   P  C  D   A  G  R   C  V  C  K   P  A  V
 601 actggagaac gctgtgatag gtgtcgatca ggttactata atctggatgg ggggaaccct
 162  T  G  E   R  C  D  R   C  R  S   G  Y  Y   N  L  D  G   N  P
 661 gagggctgta cccagtgttt ctgctatggg cattcagcca gctgccgcag ctctgcagaa
 182  E  G  C   T  Q  C  F   C  Y  G   H  S  A   S  C  R  S   S  A  E
                                                         ↦ Domain IV
 721 tacagtgtcc ataagatcac ctctaccttt catcaagatg ttgatggctg gaaggctgtc
 202  Y  S  V   H  K  I  T   S  T  F   H  Q  D   V  D  G  W   K  A  V
 781 caacgaaatg ggtctcctgc aaagctccaa tggtcacagc gccatcaaga tgtgtttagc
 222  Q  R  N   G  S  P  A   K  L  Q   W  S  Q   R  H  Q  D   V  F  S
 841 tcagcccaac gactagatcc tgtctatttt gtggctcctg ccaaatttct tgggaatcaa
 242  S  A  Q   R  L  D  P   V  Y  F   V  A  P   A  K  F  L   G  N  Q
 901 caggtgagct atgggcaaag cctgtccttt gactaccgtg tggacagagg aggcagacac
 262  Q  V  S   Y  G  Q  S   L  S  F   D  Y  R   V  D  R  G   G  R  H
 961 ccatctgccc atgatgtgat cctggaaggt gctggtctac ggatcacagc tcccttgatg
 282  P  S  A   H  D  V  I   L  E  G   A  G  L   R  I  T  A   P  L  M
1021 ccacttggca agacactgcc ttgtgggctc accaagactt acacattcag gttaaatgag
 302  P  L  G   K  T  L  P   C  G  L   T  K  T   Y  T  F  R   L  N  E
1081 catccaagca ataattggag cccccagctg agttactttg agtatcgaag gttactgcgg
 322  H  P  S   N  N  W  S   P  Q  L   S  Y  F   E  Y  R  R   L  L  R
1141 aatctcacag ccctccgcat ccgagctaca tatggagaat acagtactgg gtacattgac
 342  N  L  T   A  L  R  I   R  A  T   Y  G  E   Y  S  T  G   Y  I  D
1201 aatgtgaccc tgatttcagc ccgccctgtc tctggagccc cagcaccctg ggttgaacag
 362  N  V  T   L  I  S  A   R  P  V   S  G  A   P  A  P  W   V  E  Q
1261 tgtatatgtc ctgttgggta caagggcaa ttctgccagg attgtgcttc tggctacaag
 382  C  I  C   P  V  G  Y   K  G  Q   F  C  Q   D  C  A  S   G  Y  K
      ↦ Domain III
1321 agagattcag cgagactggg gccttttggc acctgtattc cttgtaactg tcaagggga
 402  R  D  S   A  R  L  G   P  F  G   T  C  I   P  C  N  C   Q  G  G
1381 ggggcctgtg atccagacac aggagattgt tattcagggg atgagaatcc tgacattgag
 422  G  A  C   D  P  D  T   G  D  C   Y  S  G   D  E  N  P   D  I  E
1441 tgtgctgact gcccaattgg tttctacaac gatccgcacg acccccgcag ctgcaagcca
 442  C  A  D   C  P  I  G   F  Y  N   D  P  H   D  P  R  S   C  K  P
1501 tgtccctgtc ataacgggtt cagctgctca gtgattccgg agacggagga ggtggtgtgc
 462  C  P  C   H  N  G  F   S  C  S   V  I  P   E  T  E  E   V  V  C
```

FIG 4B
(SEQ ID NO.:12 & 13)

```
1561 aataactgcc ctcccggggt caccggtgcc cgctgtgagc tctgtgctga tggctacttt
 482  N  N  C     P  P  G  V     T  G  A  R     C  E  L  C     A  D  G  Y  F
1621 ggggacccct ttggtgaaca tggcccagtg aggccttgtc agccctgtca atgcaacagc
 502  G  D  P     F  G  E  H     G  P  V  R     P  C  Q  P     C  Q  C  N  S
1681 aatgtggacc ccagtgcctc tgggaattgt gaccggctga caggcaggtg tttgaagtgt
 522  N  V  D     P  S  A  S     G  N  C  D     R  L  T  G     R  C  L  K  C
1741 atccacaaca cagccggcat ctactgcgac cagtgcaaag caggctactt cggggaccca
 542  I  H  N     T  A  G  I     Y  C  D  Q     C  K  A  G     Y  F  G  D  P
1801 ttggctccca acccagcaga caagtgtcga gcttcaact gtaacccat gggctcagag
 562  L  A  P     N  P  A  D     K  C  R  A     C  N  C  N     P  M  G  S  E
1861 cctgtaggat gtcgaagtga tggcacctgt gtttgcaagc caggatttgg tggccccaac
 582  P  V  G     C  R  S  D     G  T  C  V     C  K  P  G     F  G  G  P  N
1921 tgtgagcatg gagcattcag ctgtccagct tgctataatc aagtgaagat tcagatggat
 602  C  E  H     G  A  F  S     C  P  A  C     Y  N  Q  V     K  I  Q  M  D
                                            !→ Domain I/II
1981 cagtttatgc agcagcttca gagaatggag gccctgattt caaaggctca gggtggtgat
 622  Q  F  M     Q  Q  L  Q     R  M  E  A     L  I  S  K     A  Q  G  G  D
2041 ggagtagtac ctgatacaga gctggaaggc aggatgcagc aggctgagca ggcccttcag
 642  G  V  V     P  D  T  E     L  E  G  R     M  Q  Q  A     E  Q  A  L  Q
2101 gacattctga gagatgccca gatttcagaa ggtgctagca gatcccttgg tctccagttg
 662  D  I  L     R  D  A  Q     I  S  E  G     A  S  R  S     L  G  L  Q  L
2161 gccaaggtga ggagccaaga gaacgctac cagagccgcc tggatgacct caagatgact
 682  A  K  V     R  S  Q  E     N  S  Y  Q     S  R  L  D     D  L  K  M  T
2221 gtggaaagag ttcgggctct gggaagtcag taccagaacc gagttcggga tactcacagg
 702  V  E  R     V  R  A  L     G  S  Q  Y     Q  N  R  V     R  D  T  H  R
2281 ctcatcactc agatgcagct gagcctggca gaaagtgaag cttccttggg aaacactaac
 722  L  I  T     Q  M  Q  L     S  L  A  E     S  E  A  S     L  G  N  T  N
2341 attcctgcct cagaccacta cgtggggcca aatggctta aaagtctggc tcaggaggcc
 742  I  P  A     S  D  H  Y     V  G  P  N     G  F  K  S     L  A  Q  E  A
2401 acaagattag cagaaagcca cgttgagtca gccagtaaca tggagcaact gacaagggaa
 762  T  R  L     A  E  S  H     V  E  S  A     S  N  M  E     Q  L  T  R  E
2461 actgaggact attccaaaca agccctctca ctggtgcgca aggccctgca tgaaggagtc
 782  T  E  D     Y  S  K  Q     A  L  S  L     V  R  K  A     L  H  E  G  V
2521 ggaagcggaa gcgtagccc ggacggtgct gtggtgcaag ggcttgtgga aaaattggag
 802  G  S  G     S  G  S  P     D  G  A  V     V  Q  G  L     V  E  K  L  E
2581 aaaaccaagt ccctggccca gcagttgaca agggaggcca ctcaagcgga aattgaagca
 822  K  T  K     S  L  A  Q     Q  L  T  R     E  A  T  Q     A  E  I  E  A
2641 gataggtctt atcagcacag tctccgcctc ctggattcag tgtctccgct tcagggagtc
 842  D  R  S     Y  Q  H  S     L  R  L  L     D  S  V  S     P  L  Q  G  V
2701 agtgatcagt cctttcaggt ggaagaagca aagaggatca acaaaaagc ggattcactc
 862  S  D  Q     S  F  Q  V     E  E  A  K     R  I  K  Q     K  A  D  S  L
2761 tcaagcctgg taaccaggca tatggatgag ttcaagcgta cacaaaagaa tctgggaaac
 882  S  S  L     V  T  R  H     M  D  E  F     K  R  T  Q     K  N  L  G  N
2821 tggaaagaag aagcacagca gctcttacag aatggaaaaa gtgggagaga gaaatcagat
 902  W  K  E     E  A  Q  Q     L  L  Q  N     G  K  S  G     R  E  K  S  D
2881 cagctgcttt cccgtgccaa tcttgctaaa agcagagcac aagaagcact gagtatgggc
 922  Q  L  L     S  R  A  N     L  A  K  S     R  A  Q  E     A  L  S  M  G
2941 aatgccactt tttatgaagt tgagagcatc cttaaaaacc tcagagagtt tgacctgcag
 942  N  A  T     F  Y  E  V     E  S  I  L     K  N  L  R     E  F  D  L  Q
3001 gtggacaaca gaaaagcaga agctgaagaa gccatgaaga gactctccta catcagccag
 962  V  D  N     R  K  A  E     A  E  E  A     M  K  R  L     S  Y  I  S  Q
3061 aaggtttcag atgccagtga caagacccag caagcagaaa gagccctggg gagcgctgct
 982  K  V  S     D  A  S  D     K  T  Q  Q     A  E  R  A     L  G  S  A  A
3121 gctgatgcac agagggcaaa gaatggggcc ggggaggccc tggaaatctc cagtgagatt
1002  A  D  A     Q  R  A  K     N  G  A  G     E  A  L  E     I  S  S  E  I
```

FIG 4C (SEQ ID NO.:12 & 13)

```
3181 gaacaggaga ttgggagtct gaacttggaa gccaatgtga cagcagatgg agccttggcc
1022  E  Q  E   I  G  S  L   N  L  E   A  N  V   T  A  D  G   A  L  A
3241 atggaaaagg gactggcctc tctgaagagt gagatgaggg aagtggaagg agagctggaa
1042  M  E  K   G  L  A  S   L  K  S   E  M  R   E  V  E  G   E  L  E
3301 aggaaggagc tggagtttga cacgaatatg gatgcagtac agatggtgat tacagaagcc
1062  R  K  E   L  E  F  D   T  N  M   D  A  V   Q  M  V  I   T  E  A
3361 cagaaggttg ataccagagc caagaacgct gggggttacaa tccaagacac actcaacaca
1082  Q  K  V   D  T  R   A  K  N  A   G  V  T   I  Q  D  T   L  N  T
3421 ttagacggcc tcctgcatct gatggaccag cctctcagtg tagatgaaga ggggctggtc
1102  L  D  G   L  L  H  L   M  D  Q   P  L  S   V  D  E  E   G  L  V
3481 ttactggagc agaagctttc ccgagccaag acccagatca acagccaact gcggcccatg
1122  L  L  E   Q  K  L  S   R  A  K   T  Q  I   N  S  Q  L   R  P  M
3541 atgtcagagc tggaagagag ggcacgtcag cagaggggcc acctccattt gctggagaca
1142  M  S  E   L  E  E  R   A  R  Q   Q  R  G   H  L  H  L   L  E  T
3601 agcatagatg ggattctggc tgatgtgaag aacttggaga acattaggga caacctgccc
1162  S  I  D   G  I  L  A   D  V  K   N  L  E   N  I  R  D   N  L  P
3661 ccaggctgct acaataccca ggctcttgag caacagtgaa gctgccataa atattcctca
1182  P  G  C   Y  N  T  Q   A  L  E   Q  Q  *

3721 actgaggttc ttgggataca gatctcaggg ctcggagcc atgtcatgtg agtgggtggg
3781 atggggacat ttgaacatgt ttaatgggta tgctcaggtc aactgacctg accccattcc
3841 tgatcccatg gccaggtggt tgtcttattg caccatactc cttgcttcct gatgctgggc
3901 atgaggcaga taggcactgg tgtgagaatg atcaaggatc tggaccccaa agatagactg
3961 gatggaaaga caaactgcac aggcagatgt ttgcctcata atagtcgtaa gtggagtcct
4021 ggaatttgga caagtgctgt tgggatatag tcaacttatt ctttgagtaa tgtgactaaa
4081 ggaaaaaact ttgactttgc ccaggcatga aattcttcct aatgtcagaa cagagtgcaa
4141 cccagtcaca ctgtggccag taaaatacta ttgcctcata ttgtcctctg caagcttctt
4201 gctgatcaga gttcctccta cttacaaccc agggtgtgaa catgttctcc attttcaagc
4261 tggaagaagt gagcagtgtt ggagtgagga cctgtaaggc aggcccattc agagctatgg
4321 tgcttgctgg tgcctgccac cttcaagttc tggacctggg catgacatcc tttctttaa
4381 tgatgccatg caacttaga gattgcattt ttattaaagc atttcctacc agcaaagcaa
4441 atgttgggaa agtattact ttttcggttt caaagtgata gaaagtgtg gcttgggcat
4501 tgaaagaggt aaaattctct agatttatta gtcctaattc aatcctactt ttcgaacacc
4561 aaaaatgatg cgcatcaatg tatttatct tattttctca atctcctctc tcttttcctcc
4621 acccataata agagaatgtt cctactcaca cttcagctgg gtcacatcca tccctccatt
4681 catccttcca tccatctttc catccattac ctccatccat cccttccaaca tatatttatt
4741 gagtacctac tgtgtgccag gggctggtgg gacagtggtg acatagtctc tgccctcata
4801 gagttgattg tctagtgagg aagacaagca tttttaaaaa ataaatttaa acttacaaac
4861 tttgtttgtc acaagtggtg tttattgcaa taaccgcttg gtttgcaacc tcttgtctca
4921 acagaacata tgttgcaaga ccctcccatg ggcactgagt tggcaagga tgacagagct
4981 ctgggttgtg cacatttctt tgcattccag cgtcactctg tgccttctac aactgattgc
5041 aacagactgt tgagttatga taacaccagt gggaattgct ggaggaacca gaggcacttc
5101 caccttggct gggaagacta tggtgctgcc ttgcttctgt atttccttgg atttttcctga
5161 aagtgttttt aaataaagaa caattgttag atgccaaaaa //
```

FIG 4D
(SEQ ID NO.:14 & 15)
```
3421 ttagacggcc tcctgcatct gatgggtatg tgaacccaca acccacaacc ttccagctcc
1102  L   D  G   L   L   H   L    M   G   M    *

3481 atgctccagg gctttgctcc agaacactca ctatacctag ccccagcaaa ggggagtctc
3541 agctttcctt aaggatatca gtaaatgtgc tttgtttcca ggcccagata actttcggca
3601 ggttcccttaa catttactgg accctgtttt accgttgcta agatgggtca ctgaacacct
3661 attgcacttg ggggtaaagg tctgtgggcc aaagaacagg tgtatataag caacttcaca
3721 gaacacgaga cagcttggga atcctgctaa agagtctggc ctggaccctg agaagccagt
3781 ggacagtttt aagcagagga ataacatcac cactgtatat ttcagaaaga tcactagggc
3841 agccgagtgg aggaaagctt gaagagggggg ttagagagaa ggcaggttga gactacttaa
3901 gatattgttg aaataattga agagagaaat gacaggagcc tgctctaagg cagtagaatg
3961 gtggctggga agatgtgaag gaagattttc ccagtctgtg aagtcaagaa tcacttgccg
4021 gccgggtgtg gtggctcacg cctgtaattc tagcactttg ggagactgaa gcgggtggat
4081 cacccgaggt caggagttga agaccagcct ggccaacatg gtgaaaccct gtctctacta
4141 aaagtacaaa aattagctgg atgatggtgg tgggcgcctg taattccagc tactcaggag
4201 tctgaggcag gagaatcgct tgaacccagg aggcgaggtt acagtgagcc aagattgcac
4261 cactgctctt ccagcctggg aacagagaga ctgcctaaaa aaaaaaaaaa aaaaaa //
```

LAMININ CHAINS: DIAGNOSTIC USES

CROSS REFERENCE

This application claims the benefit of the filing date of U.S. Provisional Application No. 60/175,005, filed Jan. 7, 2000.

BACKGROUND OF THE INVENTION

Laminins are a family of basement membrane proteins which function in cell differentiation, adhesion, and migration, in addition to being true structural components (Tryggvason K, Curr. Opn. Cell Biol., 1993, 5:877–882, this and all following references are hereby incorporated by reference). The laminin molecule is a cross-shaped heterotrimer consisting of one heavy chain (≈400 kd) and two light chains, β and γ (130–200 kd) (nomenclature according to Burgeson et al., Matrix Biol., 1994, 14:209–211). Laminins exist as several isoforms each having a unique combination of α, β and γ chains. Thus far, ten genetically distinct laminin chains, α1–α5, β1–β3 and γ1–γ2 are known.

In the laminin molecule the three chains are associated through a carboxyl terminal coiled coil (long arm), most of the chains having a free amino terminal short arm. Additionally, all the α chains have a large globular G domain at the carboxyl terminus. Laminin can contribute to the structural framework of the basement membrane, but it is also believed to have a role in cell differentiation, proliferation, adhesion and migration (Timpl, R. & Brown, J. C. (1994) Matrix Biol. 14: 275–81, Yurchenco, P. D. & O'Rear, J. J. (1994) Curr. Opin. Cell. Biol. 6: 674–81). Many of the laminin chains have tissue- and cell-specific distribution which may vary between different developmental stages, indicating specific functions for the various chains and isoforms. Evidence for tissue-specific roles of some of the laminin chains has come from identification of mutations in the α2 chain gene in muscular dystrophies in mouse and man (Xu, H., Wu, X. R., Wewer, U. M. & Engvall, E. (1994) Nature Genet. 8: 297–301; Heibling-Leclerc, A., Zhang, X., Topaloglu, H., Cruaud, C., Tesson, F., Weissenbach, J., Tome', F., Schwartz, K., Fardeau, M., Tryggvason, K. & Guicheney, P. (1995) Nature Genet. 11: 216–218; Nissinen, M., Heibling-Leclerc, A., Zhang, X., Evangelista, T., Topaloglu, H., Cruaud, C., Weissenbach, J., Fardeau, M., Tome', F. M. S., Schwartz, K., Tryggvason, k. & Guicheney, P. (1996) Am. J. Hum. Genet. 58: 1177–1184), as well as in the genes for the α3, β3 and γ2 chains in epidermolysis bullosa (Pulkkinen, L., Christiano, A. M., Airenne, T., Haakana, H., Tryggvason, K. & Uitto, J. (1994a) Nature Genet. 6: 293–297; Pulkkinen, L., Christiano, A. M., Gerecke, D., Wagman, D. W., Burgeson, R. E., Pittelkow, M. R. & Uitto, J. (1994b) Genomics 24: 357–60; Aberdam, D., Galliano, M. F., Vailly, J., Pulkkinen, L., Bonifas, J., Christiano, A. M., Tryggvason, K., Uitto, J., Epstein, E. J., Ortonne, J. P. & Meneguzzi, G. (1994) Nature Genet. 6: 299–304; Kivirikko, S., McGrath, J. A., Baudoin, C., Aberdam, D., Ciatti, S., Dunnill, M. G. S., McMillan, J. R., Eady, R. A. J., Ortonne, J-P., Meneguzzi, G., Uitto, J. & Christiano, A. M. (1995) Hum. Mol. Genet. 4: 959–962; Vidal, F., Baudoin, C., Miquel, C., Galliano, M-F., Christiano, A. M., Uitto, J., Ortonne, J-P. & Meneguzzi, G. (1995) Genomics 30: 273–280).

Laminin-5, is a unique subepithelial basement membrane isoform with the molecular formula α3:β3:γ2 chains (Burgeson, R. E., Chiquet, M., Deutzmann, R., Ekblom, P., Engel, J., Kleinman, H., Martin, G. R., Meneguzzi, G., Paulsson, M., Sanes, J., Timpl, R., Tryggvason, K., Yamada, Y., & Yurchenco, P. D. (1994) Matrix Biol. 14: 209–211). Determination of the primary structure of the human α3, β3 and γ2 chains has revealed that all these chains are truncated in the short arm relative to the corresponding chains of laminin-1 (Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693; Ryan, M. C., Tizard, R., VanDevanter, D. R. & Carter, W. G. (1994) J. Biol. Chem. 269: 22779–22787; Gerecke, D. R., Wagman, D. W., Champliaud, M. F. & Burgeson, R. E. (1994) J. Biol. Chem). Additionally, the γ2 chain exists in two forms differing in the length of their carboxyl terminal end due to alternative splicing Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693; Ryan, M. C., Tizard, R., VanDevanter, D. R. & Carter, W. G. (1994) J. Biol. Chem. 269: 22779–22787; Gerecke, D. R., Wagman, D. W., Champliaud, M. F. & Burgeson, R. E. (1994) J. Biol. Chem; Airenne, T., Haakana, H., Sainio, K., Kallunki, T., Kallunki, P., Sariola, H. & Tryggvason, K. (1996) Genomics 32: 54–64). Immunolocalization of the laminin-5 protein (previously termed kalinin, nicein or epiligrin) to anchoring filaments (Verrando, P., Hsi, B., Yeh, C., Pisani, A., Serieys, N., & Ortonne, J. (1987) Exp. Cell Res. 170:116–128; Carter, W. G., Ryan, M. C. & Gahr, P. J. (1991) Cell 65: 599–610; Rousselle, P., Lunstrum, G. P., Keene, D. R. & Burgeson, R. E. (1991) J. Cell Biol, 114: 567–576) as well as epithelium-specific expression of the γ2 chain (Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693) already implied its role as an epithelial attachment component. The adhesion properties of laminin-5 have been demonstrated in several cell attachment studies (Carter, W. G., Ryan, M. C. & Gahr, P. J. (1991) Cell 65: 599–610; Rousselle, P., Lunstrum, G. P., Keene, D. R. & Burgeson, R. E. (1991) J. Cell Biol. 114: 567–576; Sonnenberg, A., Calafat, J., Janssen, H., Daams, H., van der Raaij-Helmer, L. M. H., Falcioni, R., Kennel, S. J., Aplin, J. D., Baker, J., Loizidou, M. & Garrod, D. (1991) J. Cell Biol. 113: 907–917; Niessen, C. M., Hogervorst, F., Jaspars, L. H., De Melker, A. A., Delwel, G. O., Hulsman, E. H., Kuikman, I. & Sonnenberg, A. (1994) Exp. Cell. Res. 211: 360–367; Rousselle, P. & Aumailley, M. (1994) J. Cell Biol. 125:205–214). The adhesive function of laminin-5 has been shown to be mediated through α3β1 and α6β4 integrins (Carter, W. G., Ryan, M. C. & Gahr, P. J. (1991) Cell 65: 599–610; Sonnenberg, A., Calafat, J., Janssen, H., Daams, H., van der Raaij-Helmer, L. M. H., Falcioni, R., Kennel, S. J., Aplin, J. D., Baker, J., Loizidou, M. & Garrod, D. (1991) J. Cell Biol. 113: 907–917; Rousselle, P. & Aumailley, M. (1994) J. Cell Biol. 125:205–214). Direct evidence for the crucial role of laminin-5 for epithelial cell attachment has come from the identification of mutations in the genes of all the subunit chains (Pulkkinen, L., Christiano, A. M., Airenne, T., Haakana, H., Tryggvason, K. & Uitto, J. (1994) Nature Genet. 6: 293–297; Pulkkinen, L., Christiano, A. M., Gerecke, D., Wagman, D. W., Burgeson, R. E., Pittelkow, M. R. & Uitto, J. (1994b) Genomics 24: 357–60; Aberdam, D., Galliano, M. F., Vailly, J., Pulkkinen, L., Bonifas, J., Christiano, A. M., Tryggvason, K., Uitto, J., Epstein, E. J., Ortonne, J. P. & Meneguzzi, G. (1994) Nature Genet. 6: 299–304; Kivirikko, S., McGrath, J. A., Baudoin, C., Aberdam, D., Ciatti, S., Dunnill, M. G. S., McMillan, J. R., Eady, R. A. J., Ortonne, J-P., Meneguzzi, G., Uitto, J. & Christiano, A. M. (1995) Hum. Mol. Genet. 4: 959–962; Vidal, F., Baudoin, C., Miquel, C., Galliano, M-F., Christiano, A. M., Uitto, J., Ortonne, J-P. & Meneguzzi, G. (1995) Genomics 30: 273–280) in the Herlitz's variant of junctional epidermolysis bullosa, a lethal skin blistering disease caused by disruption of the epidermal-dermal junction. One and possibly the only cell adhesion site of laminin-5 has been localized to the long arm (Rousselle, P. & Aumailley, M. (1994) J. Cell Biol. 125:205–214; Rousselle, P., Golbik, R., van der Rest, M. & Aumailley, M. (1995) J. Biol. Chem. 270:13766–13770). However, a mutation in one junctional epidermolysis bullosa patient causing an in-frame deletion of 73 residues from domains III and IV of the short arm of the laminin γ2 chain indicates a role for this part of the chain for the anchorage of epithelial cells to the extracellular matrix (Pulkkinen, L., Christiano, A. M., Airenne, T., Haakana, H., Tryggvason, K. & Uitto, J. (1994) Nature Genet. 6: 293–297).

By in situ hybridization the γ-2 chain was found to be expressed in epithelial cells of many embryonic tissues such as those of skin, lung, and kidney (Kallunki et al., 1992, supra.), and antibodies to kalinin/laminin 5, react with basement membranes of the same tissues (Rousselle et al., 1991, supra.; Verrando et al., Lab. Invest., 1991, 64:85–92).

The different laminin chains have been shown to have quite varying tissue distribution as determined by immunohistological studies, Northern, and in situ hybridization analyses. For example, the A and M chains on the one hand, and the B1 (β-1) and S (β-2) chains on the other, have been shown to be mutually exclusive (see for example Vuolteenaho et al., J. Cell Biol., 1994, 124:381–394). In vitro studies have indicated that laminin mediates a variety of biological functions such as stimulation of cell proliferation, cell adhesion, differentiation, and neurite outgrowth. The cellular activities are thought to be mediated by cell memebrane receptors, many of which are members of the integrin family (Ruoslahti, E. J. Clin. Invest., 1991, 87:1–5; Mecham, R. P. FASEB J., 1991, 5:2538–2546; Hynes, R. Cell, 1992, 69:11–25). Recently a new nomenclature for describing laminins has been agreed to as in the following Table 1 (after Burgeson et al., 1994, supra.):

TABLE 1

Laminin Chains and Genes

| New | Previous | Gene |
| --- | --- | --- |
| α1 | A, Ae | LAMA1 |
| α2 | M, Am | LAMA2 |
| α3 | 200 kDa | LAMA3 |
| β1 | B1, B1e | LAMB1 |
| β2 | S, B1s | LAMB2 |
| β3 | 140 kDa | LAMB3 |
| γ1 | B2, B2e | LAMC1 |
| γ2 | B2t | LAMC2 |

Heterotrimers of Laminin

| New | Chains | Previous |
| --- | --- | --- |
| Laminin-1 | α1β1γ1 | EHS laminin |
| Laminin-2 | α2β1γ1 | merosin |
| Laminin-3 | α1β2γ1 | s-laminin |
| Laminin-4 | α2β2γ1 | s-merosin |
| Laminin-5 | α3β3γ2 | kalinin/nicein |
| Laminin-6 | α3β1γ1 | k-laminin |
| Laminin-7 | α3β2γ1 | ks-laminin |

Cell migration is one of the biological functions proposed for laminin (Timpl, R. & Brown, J. C. (1994) Matrix Biol. 14: 275–81). Cellular movement is required for various physiological and pathological processes, such as during embryogenesis, wound healing, angiogenesis and tumor invasion. Immunohistochemical and in situ hybridization studies have shown induction of laminin-5 expression in migrating keratinocytes during wound healing (Ryan, M. C., Tizard, R., VanDevanter, D. R. & Carter, W. G. (1994) J. Biol. Chem. 269: 22779–22787; Larjava, H., Salo, T., Haapasalmi, K., Kramer, R. H. & Heino J. (1993) Clin. Invest. 92: 1425–1435; Pyke, C., Romer, J., Kallunki, P., Lund, L. R., Ralfkiaer, E., Dano, K. & Tryggvason, K (1994) Am. J. Pathol. 145: 782–791). The γ2 chain of laminin-5 has also been shown to be strongly expressed in malignant cells located at the invasion front of several human carcinomas, as determined by in situ hybridization and immunohistochemical staining (Pyke, C., Romer, J., Kallunki, P., Lund, L. R., Ralfkiaer, E., Dano, K. & Tryggvason, K (1994) Am. J. Pathol. 145: 782–791; Pyke, C., Salo, S., Ralfkiaer, E., Romer, J., Dano, K. & Tryggvason, K. (1995) Cancer Res. 55: 4132–4139). Since laminin-1 has been found to inhibit keratinocyte migration in vitro (Woodley, D. T., Bachmann, P. M. & O'Keefe, E. J. (1988) J. Cell. Physiol. 136: 140–146), and as the laminin α1, β1 and γ1 chains are only weakly expressed throughout cancerous areas with no apparent correlation to sites of invasion, laminin-5 has been proposed to have a role in the migration event (Pyke, C., Romer, J., Kallunki, P., Lund, L. R., Ralfkiaer, E., Dano, K. & Tryggvason, K (1994) Am. J. Pathol. 145: 782–791).

SUMMARY OF THE INVENTION

The instant invention provides for methods of detecting kalinin/laminin 5 expression in tissue comprising detecting a signal from assayed tissue, such signal resulting from specifically hybridizing tissue with an effective amount of a nucleic acid probe, which probe contains a sense or antisense portion of kalinin/laminin 5 gamma-2 nucleic acid sequence (Kallunki et al., 1992, supra.). In particular, where the nucleic acid probe is DNA, RNA, radio-labeled, enzyme labeled, chemiluminescent labeled, avidin or biotin labeled, derived from human kalinin/laminin 5 gamma-2 nucleic acid sequence, incorporated into an extrachromasomal self-replicating vector, a viral vector, is linear, circularized, or contains modified nucleotides. In the preferred embodiment the probes are linearized specific regions of the γ-2 gene.

The instant invention also provides for methods for detecting the presence of invasive cells in tissue comprising detecting a signal from assayed tissue, such signal resulting from contacting tissue with an effective amount of a nucleic acid probe, which probe contains a sense or antisense portion of kalinin/laminin 5 γ-2 nucleic acid sequence (Kallunki et al., 1992, supra.). In particular, where the nucleic acid probe is DNA, RNA, radio-labeled, enzyme labeled, chemiluminescent labeled, avidin or biotin labeled, derived from human kalinin/laminin 5 gamma-2 nucleic acid sequence, incorporated into an extrachromasomal self-replicating vector, a viral vector, is linear, circularized, or contains modified nucleotides. In the preferred embodiment the probes are linearized specific regions of the γ-2 gene. The instant method also provides for the diagnosis of the absence of γ-2 chain expression, useful for the monitoring of therapies, and the progress of malignant cell transformation leading to accurate determination of the extent of invasive cell activity.

The instant invention further provides for a method for detecting kalinin/laminin 5 expression in tissue comprising detecting a signal from assayed tissue, such signal resulting from contacting tissue with an effective amount of a labeled probe, which probe contains an antibody immunoreactive with a portion of kalinin/laminin 5 gamma-2 protein.

Further provided is a method for detecting invasive cells in tissue comprising detecting a signal from assayed tissue, such signal resulting from contacting tissue with an effective amount of a labeled probe, which probe contains an antibody immunoreactive with a portion of kalinin/laminin 5 gamma-2 protein. Also provided is a method for detecting kalinin/laminin 5 in tissue comprising detecting a signal from assayed tissue, such signal resulting from contacting tissue with an effective amount of a labeled probe, which probe contains an antibody immunoreactive with a potion of kalinin/laminin 5 gamma-2 protein. Thus the method of the instant invention provides for the absence of such signal as diagnostic for the absence of invasive cells.

Further, the present invention provides for a method of using the laminin-5 molecule to promote adhesion of cultured epithelial and carcinoma cells.

Additionally, the present invention is directed to a method for blocking migration of cells using antibodies against the γ-2 chain of the laminin-5 molecule. Evidence for the relationship of γ2 chain expression with cell migration was obtained by the identification of an enhancer element in the LAMC2 gene in studies on promoter-reporter gene constructs in transgenic mice.

BRIEF DESCRIPTION OF THE DRAWINGS

FIGS. 1A–D shows in situ hybridization of a specimen of colon adenocarcinoma for γ-2 chain mRNA using a S-35 labeled anti-sense RNA probe derived from plasmid pbb2r-02. Magnification: 1A×100; 1B–1D×640.

FIG. 3A is a photo of in situ hybridization on a stained section showing γ-2 chain signal. FIG. 3A-1 is a photo showing the dark field image of 3A.

FIGS. 4A–D shows the nucleic acid sequence for the γ-2 chain cDNA and the derived amino acid sequence. FIG. 4A-4C is the full cDNA for the 5,200 base pair sequence, available from EMB/GenBank/DDBJ under the accession number Z15008. FIG. 4D is the nucleotide and derived amino acid sequence of the alternative 3' end sequence from cDNA clones providing a sequence of 4,316 base pairs, available from EMB/GenBank/DDBJ under the accession number Z15009. (Kallunki, et al., 1992, supra.) SEQ ID NOs: 12, 13, 14, and 15.

DETAILED DESCRIPTION OF THE INVENTION

Figure 1:
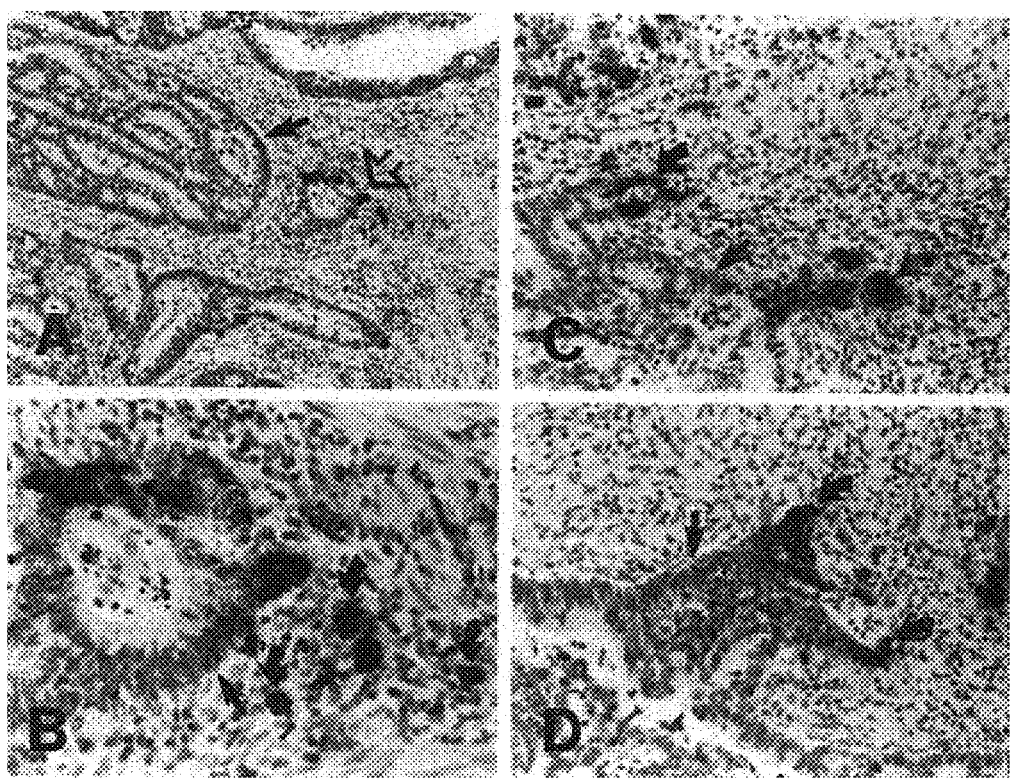

Epidermolysis bullosa (EB) is a group of mechanobullous disorders characterized by fragility of the skin and mucous membranes (see Lin & Carter eds., Epidermolysis bullosa. Basic and clinical aspects, 1992, Springer Verlag, N.Y.; Fine et al., J. Am. Acad. Dermatol., 1991, 24:119–135). The junctional forms of EB (JEB) are characterized by tissue separation at the level of the lamina lucida within the dermal-epidermal basement membrane, and no specific mutation had yet to be reported. Recently it has been proposed that the genes for a lamina lucida protein kalinin/nicein/epiligin may be a candidate in some forms of JEB (Verrando et al., 1991, supra.). Several lines of evidence suggest that anchoring filament proteins could be defective in some forms of JEB. First, attenuation or absence of immunoreactivity with anti-kalinin(epiligrin) antibodies has been noted in the skin of patients with the most severe (Herlitz) type of JEB. The immunofluorescence staining patterns may be of prognostic value in classifying JEB, and these immunoreagents have been used for prenatal diagnosis of JEB using fetal skin biopsy specimens. Second, the kalinin/laminin 5 γ-2 chain is expressed in epithelial cells of the skin, trachea and kidneys, tissues which are frequently affected by JEB.

Since the majority of cases are of the generalized (Herlitz) phenotype (H-JEB), JEB patients have been classified into Herlitz and non-Herlitz types. Clinical features of H-JEB include mechanical fragility of the skin, with widespread blistering and erosions, rapid deterioration and neonatal death, often from sepsis. Longterm survival is rare.

Efforts to identify the basic defect in JEB began with the observation that a monoclonal antibody that binds to the lamina lucida of the epidermal basement membrane zone of normal skin, fails to react with the lamina lucida of H-JEB skin (Verrando et al., 1991, supra.). The antigen recognized by this antibody was purified from keratinocyte culture medium and termed BM600/nicein. Keratinocytes cultured from the skin of H-JEB patients attach poorly to substrate and fail to accumulate immunologically detectable nicein. Further experiments with antibodies specific for the α3 chain of nicein, demonstrated that they were capable of inducing the rounding and detachment of adherent keratinocytes without affecting fibroblasts (Rousselle et al., 1991, supra.). Thus the correlation in vivo and in vitro of the dermoepidermal separation with deficient nicein/kalinin/laminin 5 immunoreactivity and the separation induced by anti-nicein antibody have made the genes encoding this protein strong candidates for the site of H-JEB mutations.

The importance of the γ-2 chain of nicein/kalinin/laminin 5 in JEB, and epithelial tissues prompted the investigation into the role such adhesion contacts between epithelial cells may play in abberant cells. Of primary interest was the role γ-2 chain of nicein/kalinin/laminin 5 abberant expression may play in cancer tissue, and a possible role in cancer dissemination.

It has been recently shown that in colon adenocarcinoma, a significant positive correlation between the degree of tumor budding and the recurrence of tumors following curative surgery exists, and that this fact is likely to reflect a higher invasive potential of budding cancer cells as compared with cancer cells located deeper in the tumor (Hase et al., Dis. Colon Rectum, 1993, 36:627–635). Therefore, as demonstrated in Example 3 below, the instant invention allows for the useful prognostic determination of success of surgery, means for monitoring progression of rumor budding and subsequent prognosis.

The identification of the role of γ-2 chain allows for the novel use of kalinin/laminin 5 γ-2 chain and its ligand, as diagnostic probes of the tumor cell/basement membrane adhesion interface that is crucial for the invasion of non-malignant tissues, and identifies invasive cells.

Thus the identification of the role of γ-2 chain allows for the novel therapeutic intervention of binding of kalinin/laminin 5 to its ligand, and thereby reducing the tumor cell/basement membrane adhesion that is crucial for the invasion of non-malignant tissues, and method for inhibiting the budding of tumor masses, and a means for determing the level of γ-2 chain expression as a measure of budding activity of a given tumor.

As demonstrated in Example 3 below, the γ-2 chain of kalinin/laminin 5 is preferentially expressed by invasively growing malignant cells in human carcinomas. Furthermore, migrating keratinocytes in wound healing also expressed this gene, pointing to a role of γ-2 chain in epithelial cell migration both in malignant and in nonmalignant pathological conditions. The consistent expression of the γ-2 chain gene in invading cancer cells reflects a functional importance of this molecule in vivo in establishing contacts between the invading malignant cells and a provisional matrix in the immediate surroundings of the cancer cells. The instant invention provides methods for the identification of, and diagnosis of invasive cells and tissues, and for the monitoring of the progress of therapeutic treatments.

In a preferred embodiment of this aspect of the instant invention the nucleic acid probe comprise a specifically hybridizing fragment of the γ-2 chain cDNA nucleic acid sequence. In this embodiment, the nucleic acid sequence comprises all or a specifically hybridizing fragment of an open reading frame of the nucleic acid sequence for the γ-2 chain (FIG. 4) encoding the amino acid sequence of the γ-2 chain (FIG. 4). It will be understood that the term "specifically hybridizing" when used to describe a fragment of nueleic acid encoding a human laminin γ-2 chain gene is intended to mean that, nueleic acid hybridization of such a fragment is stable under high stringency conditions of hybridization and washing as the term "high stringency" would be understood by those having skill in the molecular biological arts.

Further, the instant invention provides for the therapeutic treatment of such invasive tissues by using γ-2 chain or biologically active fragments thereof to interfere with the interactions between aberrant γ-2 chain and surrounding tissues. The instant invention also provides for the intervention of γ-2 chain interaction with surrounding tissues by using specific anti-γ-2 chain antibodies (monoclonal or polyclonal) to inhibit the γ-2 chain biological activity.

The instant disclosure also allows one to ablate the invasive cell phenotypic γ-2 chain expression by using genetic manipulation to "knock-out" the functional expression of the γ-2 chain gene in cancer cells, or to completely "knock-out" the functional γ-2 chain gene in the genome of cancer cells. Such knock-outs can be accomplished by using genetic molecular biological techniques for inserting by homologous recombination into genomic DNA, targeted transposon insertion, or random insertion/deletion mutations in the genomic DNA.

The instant disclosure also allows for the therapeutic treatment of invasive cell phenotype by the inhibition of functional γ-2 chain expression in targeted cells by using anti-sense technology, such methods for anti-sense production, stabilization, delivery, and therapeutic approaches are reviewed in Uhlmann et al., 1990, Chem. Reviews 90:543–584).

Moreover, the present invention is also directed to two important functional aspects of the epithelium specific laminin-5, i.e. cell adhesion and migration. First of all, according to the present invention, the γ2 subunit chain, as such, does not promote cell adhesion and, secondly, the laminin-5 isoform and its γ2 chain subunit play a role in the migratory process of cells of epithelial origin. According to the present invention, the migratory function of the γ2 chain is a characteristic for domain III, as shown with antibody inhibition studies. Furthermore, involvement of the γ2 chain in cell migration was shown to be related with a cis-acting element in LAMC2 gene, as studied in transgenic mice using promoter-reporter gene constructs.

Thus the instant invention provides for a method of detection, diagnosis, prognosis, monitoring, and therapeutic treatment of invasive cell phenotypes.

The examples below are meant by way of illustration, and are not meant to be limiting as to the scope of the instant disclosure.

EXAMPLE 1

Mutation in the γ2 Chain Gene LAMC2 is Critical in Some Cases of JEB

A unique scanning strategy using RT-PCR amplification of LAMC2 sequences was devised to detect truncated forms of γ-2 chain gene transcripts (Pulkkinen et al., Nature Genetics, 1994, 6:293–298). The 3.6 kilobase coding sequence of the LAMC2 mRNA, was reverse transcribed and amplified with eight pairs of primers, producing overlapping PCR amplimers designated A-H. The PCR products were then examined by agarose gel electrophoresis, followed by MDE heteroduplex analysis. If bands with altered mobility were detected, the PCR products were sequenced, and compared with normal sequences from unaffected family members or unrelated individuals. Intron/exon borders were identified by PCR analysis of genomic DNA, deduced by comparison with cDNA sequences.

A Point Mutation Produces Exon Skipping

When a panel of five unrelated JEB patients were analysed, the primers used to amplify segment C (nt 1046–1537) produced a markedly shortened band of 273 base pairs, as compared with the normal 491 base pairs. No evidence of the normal sized band was noted, suggesting that the patient was homozygous for this allele. Direct sequencing revealed that the shortened product resulted from the deletion of 219 base pairs corresponding to nucleotides 1184–1402 in the cDNA, thus exon 9 was deleted. The remaining nucleotide sequences within this and other PCR products did not reveal any additional mutations upon MDE analysis.

Subsequent examination of the genomic DNA revealed that the sequences for exons 8, 9 and 10 were present, however a homozygous G for A substitution at the 3' acceptor splice site at the junction of intron 8 and exon 9, abolished the obligatory splice site sequence (AG).

Examination of another patient revealed that PCR product F (nt 2248–2777) corresponding to domains I and II of the γ-2 chain, was a band with altered mobility. Sequencing the abnormal product revealed a 20 bp deletion, followed by a single base pair (G) insertion in the coding region corresponding to exon 16. This mutation causes a frameshift which results in a premature stop codon 51 base pairs downstream from the deletion-insertion, producing a truncated kalinin/laminin 5 γ-2 chain terminating at residue 830.

RT-PCR and MDE Analyses

RNA isolated from fibroblast cell cultures of JEB patients was used as template for RT-PCR of the LAMC2 mRNA. (Epidermal keratinocytes can also be used). cDNA was prepared from 50 μg of total RNA in a volume of 100 μL according to manufacturer's reccomendations (BRL), and oligonucleotide primers were synthesized on the basis of the cDNA sequence (FIG. 4; Kallunki et al., 1992, supra.), to generate about 500 base pair products, which spanned the entire coding region.

For PCR amplification, 1 μL of cDNA was used as template and amplification conditions were 94° C. for 5 min followed by 95° C. for 45 sec, 60° C. for 45 sec and 72° C. for 45 sec for 35 cycles in an OmniGene thermal cycler (Marsh Scientific). Amplification was performed in a total volume of 25 μL containing 1.5 mM MgCl.sub.2, and 2 U Taq polymerase (Boehringer Mannheim). Aliquots of 5 μL were analysed on 2% agarose gels and MDE heteroduplex analysis was performed according to the manufacturer's reccomendation (AT Biochemicals). Heteroduplexes were visualized by staining with ethidium bromide. If a band of altered mobility was detected in heteroduplex analysis, the PCR product was subcloned into the TA vector (Invitrogen), and sequenced by standard techniques.

DNA isolated either from fibroblast cultures or from specimens obtained from buccal smears, was used as template for amplification of genomic sequences. For amplification of introns 8 and 16, .about.500 ng of genomic DNA was used as template and the following oligomer primers were utilized.

```
5'GGCTCACCAAGACTTACACA 3'  (SEQ ID NO:1);

5'GAATCACTGAGCAGCTGAAC 3'  (SEQ ID NO:2);

5'CAGTACCAGAACCGAGTTCG 3'  (SEQ ID NO:3);

5'CTGGTTACCAGGCTTGAGAG 3'  (SEQ ID NO:4);

5'TTACTGCGGAATCTCACAGC 3'  (SEQ ID NO:5);

5'TACACTGTTCAACCCAGGGT 3'  (SEQ ID NO:6);

5'AAACAAGCCCTCTCACTGGT 3'  (SEQ ID NO:7);

5'GCGGAGACTGTGCTGATAAG 3'  (SEQ ID NO:8);

5'CATACCTCTCTACATGGCAT 3'  (SEQ ID NO:9);
```

-continued

5'AGTCTCGCTGAATCTCTCTT 3' (SEQ ID NO:10);

5'TTACAACTAGCATGGTGCCC 3' (SEQ ID NO:11);

Amplification conditions were 94° C. for 7 min followed by 95° C. for 1.5 min, 56° C. (intron 8) or 58° C. (intron 16) for 1 min and 72° C. for 1.5 min for 35 cycles in an OmniGene thermal cycler (Marsh Scientific). Amplification was performed in a total volume of 25 µL containing 1.5 mM MgCl.sub.2, and 2 U Taq polymerase (Boehringer Mannheim). The PCR products were subcloned and sequenced as above.

Verification of Mutations

The putative mutations detected in the PCR products were verified at the genomic level in both cases. For this purpose, a search for a potential change in restriction endonuclease sites as a result of the mutation was performed.

Amplification conditions were 94° C. for 7 min followed by 94° C. for 1 min, 58° C. for 45 sec and 72° C. for 45 sec for 35 cycles in an OmniGene thermal cycler (Marsh Scientific). PCR products were analysed on 2.5% agarose gels.

The methods described allow for the screening of patients for mutations in the γ-2 chain which will correlate with JEB. As demonstrated, the results have identified a homozygous point mutation resulting in oxon skipping, and a heterozygous deletion-insertion mutation. This demonstrating the effective screening for, and identification of, γ2 chain mutations which correlate with JEB. The methods are thus useful for diagnosis, prenatal screening, early screening and detection, as well as detailed examination of JEB. Further, the results show that the functional role of γ-2 chain expression in epithelial cells is important in determining proper intercellular connectivity, relating to the integrity of tissues and cell interactions.

EXAMPLE 2

Mutation in the γ-2 Chain Gene LAMC2 is Critical in H-JEB

The correlation both in vivo and in vitro of the dermoepidermal separation in H-JEB, with deficient immunoreactivity of anti-nicein/kalinin/laminin 5 antibodies, and the separation induced by anti-nicein/kalinin/laminin 5 antibodies have made the genes encoding this protein strong candidates for the site of H-JEB mutations. In this example, it is demonstrated that the molecular defect which causes H-JEB is linked to the gene encoding nicein/kalinin/laminin 5 γ-2 chain. In particular, the occurence of a homozygous premature termination codon mutation is the specific cause in an examined case of H-JEB (Aberdam et al., Nature Genetics, 1994, 6:299–304).

Expression of mRNA encoding the three nicein subunits by northern analysis of RNA isolated from primary keratinocyte culture of a H-JEB patient was determined as the initial screen. Hybridization with probes for the α-3 and β-3 subunits was normal, but no hybridization with a cDNA encoding the γ-2 subunit was detected. Examination of the genomic DNA for gross abnormalities, such as large deletions, insertions or rearrangements, in LAMC2 (the γ-2 subunit gene) by Southern blot analysis turned up no abnormalities when the genomic DNA was digested with BamHI, BglI, HindIII, PstI or PvuII and probed with full length LAMC2 cDNA.

Possible mutations in the γ-2 subunit were sought by using cDNA reverse transcribed from total RNA purified from cultured keratinocytes of the H-JEB patient, and subjected to PCR amplification. The size of the amplified products was checked by electrophoresis on 2% agarose gels and compared with that obtained from healthy controls.

No major differences were detected in the agarose gels, and the PCR products were examined by heteroduplex analysis (MDE). Heteroduplex analysis of the most 5' PCR product (nt 35–726) revealed the presence of a homoduplex in the proband (pateint) and the controls. However, when the amplified PCR products from the patient and control were mixed together, an additional band with altered mobility, representing heteroduplexes, was detected, suggesting a homozygous mutation in the patient's LAMC2 cDNA. This amplified fragment corresponded to domain V of the γ-2 protein (Vailly et al., Eur. J. Biochem., 1994, 219:209–218). Sequencing detected a C to T transition at position +283, leading to a nonsense mutation in which a termination codon TGA replaces an arginine (CGA), perhaps arising as a result of the hypermutability of 5-methyl-cytosine to thymine at CpG nucleotides. This mutation, R95X, leads to truncation of the γ-2 subunit polypeptide at amino acid 95 and loss of a TaqI restriction site (TCGA). Digestion of cDNA with TaqI confirmed the presence of a homozygous mutation in the DNA of the H-JEB patient. No other mutations were detected.

To confirm the cosegregation of the mutation with the loss of the TaqI restriction site, eight genotyped individuals of the family of the patient were screened. In each case, a 120 base pair fragment was amplified by PCR using genomic DNA templates and primers flanking the restriction site. Upon digestion of the wild type amplification product, two clevage fragments of 80 and 40 base pairs are generated. Consistent with the presence of a heterozygous mutation in carriers of this genotype, DNA fragments of 120, 80 and 40 base pairs, indicative of a wild type genotype, were found in the paternal grandmother and two other relatives.

Cell Culture

Epidermis was separated from dermis by dispase treatment at 37 C. Keratinocytes were dissociated in 0.25% trypsin at 37° C. and plated onto a feeder layer of irradiated mouse 3T3 cells (ICN) (Rheinwald & Green, Cell, 175, 6:331–334). Keratinocytes were grown in a 1:1 mixture of DMEM and Ham's F12 (BRL) containing 10% Fetal Calf Serum (FCS), 1 mM sodium pyruvate, 2 mM L-glutamine, 10 µg/mL of penicillin and strptomycin, 10 ng/mL transferrin, 180 µM adenine and 20 pM T3 (Simon & Green, Cell, 1985, 40:677–683). H-JEB keratinocytes were expanded after gentle dissociation in 0.05% trypsin, 0.02% EDTA.

Northern Blot Analysis

Total RNA was prepared from H-JEB and normal cultured keratinocytes according to standard methods (Chomzynski & Sacchi, Anal. Biochem., 1987, 162: 156–159). RNA was electrophoresed in 1.2% denaturing agarose gels containing 1.2M formaldehyde and transferred onto Hybond N membrane (Amersham). Membranes were hybridized at high stringency with P-32 labeled cDNA probes corresponding to the different chains of nicein, and then exposed on Hyperfilm MP (Amersham) with intensifying screens. Radiolabeled cDNA probes NA1 (Baudoin et al., J. Invest. Dermatol., 1994, in press), KAL-5.5C (Gerecke et al., Eur. J. Biochem., 1994, in press), and PCR 1.3 (Vailly et al., 1994, supra.), were used to detect the mRNAs for nicein chains α-3, β-3 and γ-2, respectively.

RT-PCR and Heteroduplex Analysis (MDE)

50 µg of total RNA isolated from cultured keratinocytes from JEB patient, and unrelated healthy controls were reverse transcribed in a volume of 100 μL as recommended by the manufacturer (BRL). 1 μL of the reaction product was used to amplify overlapping regions of the cDNA that spanned the open reading frame. Primer pair used to identify the mutation R95X: (L) 5'-GAGCGCAGAGTGAGAACCAC-3' SEQ ID NO:16, (R) 5'-ACTGTATTCTGCAGAGCTGC-3' SEQ ID NO:17. PCR cycling conditions were: 94° C., 5 min, followed by 94° C., 45 sec; 60° C., 45 sec; 72° C., 45 sec; for 35 cycles, and extension at 72° C. for 5 min. 5 μL aliquots were run in 2% agarose gels. Heteroduplex analysis was performed as recommended by the manufacturer (MDE, AT Biochemicals). Heteroduplexes were visualized under WV light in the presence of ethidium bromide and photographed. Amplified cDNA fragments with altered mobility were subcloned into the TA vector according to the manufacturer's recommendations (Invitrogen). Sequence analysis were then performed using standard techniques.

Verification of the Mutation

PCR reactions on genomic DNA (50 μg) were carried out using the upstream primer 5'-TTCCTTTCCCCTACCTTGTG-3' (SEQ ID NO:18) and the downstream printer 5'-TGTGGAAGCCTGGCAGACAT-3' (SEQ ID NO: 19), which are located in the intron 2 and exon 3 of LAMC2 respectively. PCR conditions were: 95° C., 5 min, followed by 94° C., 45 sec; 56° C., 45 sec; 72° C., 45 sec; for 35 cycles, and extentions at 72° C. for 5 min. PCR products were used for restriction analysis. 20 μL of PCR product obtained from genomic DNA was digested with TaqI for 2 hours (Boehringer Mannheim). Cleavage products were electrophoresed (2.4% agarose) stained and visualized under UV light.

Thus the methods allow for the screening of patients for mutations in the γ-2 chain which correlate with H-JEB. As demonstrated, the results have identified a nonsense mutation resulting in a truncated γ-2 chain, leading to severe H-JEB. This was further confirmed by specific amplification and restriction enzyme analysis of both the patient and relatives. Thus demonstrating the effective screening for, and identification of, γ-2 chain mutations which correlate with H-JEB. The methods are thus useful for diagnosis, prenatal screening, early screening and detection, as well as detailed examination of H-JEB. Furthermore, the results demonstrate the significance of the γ-2 chain in forming proper cellular contacts.

EXAMPLE 3

γ-2 Chain as Diagnostic for Invasive

In this example, in situ hybridization is used to demonstrate the expression of the kalinin/laminin 5 γ-2 chain in a variety of human cancer tissues and in skin wound healing in mice (Pyke et al., Amer. J. Pathol., October. 1994, 145(4):1–10).

Thirty-six routinely processed, formalin-fixed and paraffin wax-embedded specimens from cancer surgery performed from 1991 to 1993 were drawn from pathology department files at Herlev Hospital (Copenhagen, Denmark). The specimens were evaluated according to standard criteria and included 16 cases of moderately or well-differentiated colon adenocarcinomas, 7 cases of ductal mammary carcinomas, 4 squamous cell carcinomas (2 skin, 1 cervix, 1 vulva), 3 malignant melanomas, and 6 sarcomas (3 leiomyosarcomas, 2 malignant fibrous histiocytomas, 1 neurofibrosarcoma).

All samples were selected upon histological examination of a hematoxylin and eosinstained section to ensure that they showed a well preserved morphology throughout and contained representative areas of both cancerous tissue and surrounding apparently normal, unaffected tissue. The broad zone separating these two tissue compartments is referred to as the invasive front in the following. No estimation of the effect of variations in fixation conditions was attempted, but in a previous study of plasminogen activating system components using specimens of colon adenocarcinomas collected using the same procedures, very little variation in relative mRNA levels was found (Pyke, C. PhD. Thesis, 1993, University of Copenhagen, Denmark). In addition, tissue from incisionally wounded mouse skin prepared as described by Romer et al. (J. Invest. Dermatol., 1994, 102:519–522), was fixed and paraffin-embedded the same way as the human cancer specimens.

For preparation of total RNA from six samples of colon adenocarcinomas, tissues were snap-frozen in liquid nitrogen immediately following resection and RNA was prepared as described by Lund et al., (Biochem. J., 1994).

Probes:

Fragments of the cDNA for the γ-2 chain of human kalinin/laminin 5 were inserted into RNA transcription vectors by restriction enzyme cutting of clone L15 covering base pairs 2995 to 3840 (FIG. 4; Kallunki et al., 1992, supra.). In brief, plasmids phb2t-01 and phb2t-02 were prepared by insertion of the complete L15 γ-2 chain cDNA in sense and anti-sense orientation into the polylinker of plasmid vectors SP64 and SP65 (both Promega, Madison, Wis.), respectively. In addition, two non-overlapping fragments of clone L15 were bluntend cloned into the EcoRV-site of pKS(Bluescript)II(+) (Stratagene, La Jolla, Calif.) transcription vector and the resulting plasmids were verified by dideoxy sequencing according to Sanger et al. (PNAS (USA), 1977, 74:5463–5471). Plasmid phb2t-03 cover bases 3003–3239 and phb2t-05 cover bases 3239 to 3839, numbers referring to cDNA sequence Z15008 in the EMBL/GenBank/DDBJ database as reported by Kallunki et al., (1992, supra.; FIG. 4).

Similarly, cDNA fragments of other human laminin chains were prepared in RNA transcription vectors, yielding the following plasmid constructs (numbers in brackets refer to base pair numbers in the EMBL/GenBank/DDBJ sequence database by the listed accession numbers); chain α-1: plasmid phae-01 (3244–3584 (accession No. X58531, Nissinen et al., Biochem. J., 1991, 276:369–379) in pKS (Bluescript)II(+)); chain β-1: plasmid phble-01 (3460–4366 (accession No. J02778, Pikkarainen et al., J. Biol. Chem., 1987, 262:10454–10462) in pKS(Bluescript)II(+)); chain γ-1: plasmids A1PSP64 and A1PSP65 (919–1535 (accession No. M55210, Pikkarainen et al., J. Biol. Chem., 1988, 263:6751–6758) in SP64 and SP65 repectively (sense and anti-sense orientation)).

All plasmids were linearized for transcription using restriction endonucleases and 5 μg of the linearized plasmids was extracted with phenol and with choloroform/isoamyl alcohol (25:1), precipitated with ethanol, and redissolved in water. Each transcription reaction contained 1 μg linearized DNA template, and transcriptions were performed essentially as recommended by the manufacturer of the polymerases. The RNA was hydrolyzed in 0.1 mol/L sodium carbonate buffer, pH 10.2, containing 10 mmol/L dithiothreitol (DTT) to an average size of 100 bases. RNA probes transcribed from opposite strands of the same plasmid template, yielding sense and anti-sense transcripts, were adjusted to ×10.sup.6 cpm/μL and stored at −20° C. until used. Probes were applied to tissue sections.

In situ Hybridization:

In situ hybridization was performed as described by Pyke et al., (Am. J. Pathol., 1991, 38:1059–1067) with 35S labeled RNA probes prepared as described above. In brief, paraffin sections were cut, placed on gelatinized slides, heated to 60° C. for 30 minutes, deparaffinized in xylene, and rehydrated through graded alcohols to PBS (0.01 mol/L sodium phosphate buffer, pH 7.4, containing 0.14 mol/L NaCl). The slides were then washed twice in PBS, incubated with 5 μg/mL proteinase K in 50 mmol/L Tris/HCl, pH 8.0, with 5 mmol/L EDTA for 7.5 minutes, washed in PBS (2 minutes), dehydrated in graded ethanols, and air-dried before the RNA probe (.about.80 pg/μL) was applied. The hybridization solution consisted of deionized formamide (50%), dextran sulfate (10%), tRNA (1 μg/μL), Ficoll 400 (0.02% (w/v)), polyvinylpyrrolidone (0.02% (w/v)), BSA fraction V (0.02% (w/v)), 10 mmol/L DTT, 0.3M NaCl, 0.5 mmol/L EDTA, 10 mmol/L Tris-HCl, and 10 mmol/L NaPO.sub.4 (pH 6.8). Sections were covered by alcohol-washed, autoclaved coverslips and hybridized at 47° C. overnight (16 to 18 hours) in a chamber humidified with 10 ml of a mixture similar to the hybridization solution, except for the omission of probe, dextran sulfate, DTT, and tRNA (washing mixture). After hybridization, slides were washed in washing mixture for 2×1 hour at 50° C., followed by 0.5 mol/L NaCl, 1 mmol/L EDTA, 10 mmol/L Tris-HCl (pH 7.2) (NTE) with 10 mmol/L DTT at 37° C. for 15 minutes. After treatment with RNAse A (20 μg/mL) in NTE at 37° C. for 30 minutes, the sections were washed in NTE at 37° C. (2×30 minutes), and in 2 L of 15 mmol/L sodium chloride, 1.5 mmol/l sodium citrate, pH 7.0, with 1 mmol/L DTT for 30 minutes at room temperature with stirring. Sections were then dehydrated and air-dried. Finally, autoradiographic emulsion sec applied according to the manufacturer's reccomendations, and sections were stored in black airtight boxes at 4 C. until they were developed after 1 to 2 weeks of exposure.

Results; Laminin α-1, γ-1, and γ-2 Chains

All rounds of in situ hybridization include both sense and anti-sense RNA probes for each of the genes studied. As negative controls, sense RNA probes are applied to adjacent sections and these probes consistently are negative. As a positive control of the γ-2 chain hybridizations, two anti-sense probes derived from non-overlapping γ-2 chain cDNA clones are used on a number of sections. To summarizes the γ-2 chain expression found; all carcinomas were positive except for one case of mammary duct carcinoma, and all three cases of leiomyosarcomas, both cases of malignant fibrous histiocytoma, and the only case of neurofibrosarcoma. The positive controls always give similar staining on adjacent sections (see FIG. 2, E and G). Fifteen of the malignant cases and all mouse tissue blocks were hybridized on two or more separate occasions giving the same hybridization pattern. All cell types other than those described below were negative in all cases.

Colon Adenocarcinoma

Sixteen specimens of colon adenocarcinoma were investigated by in situ hybridization for expression of the γ-2 chain (FIG. 1). In all of these cases, mRNA for γ-2 chain was present exclusively in cancer cells and in most of the cases, staining was confined to a distinct subpopulation of cancer cells at the invasive front (FIG. 1, A-D). A characteristic feature of γ-2 chain containing cancer cells at the invasive front was that they appeared to represent cells in the process of branching or dissociating from larger well differentiated epithelial glands, a phenomenon referred to in the literature as tumor budding or tumor-cell dissociation.

In normal-looking colon mucosa distal from the invasive carcinoma, moderate signals for γ-2 chain MRNA were observed in two specimens in the epithelial cells of a few mucosal glands that showed clear morphological signs of glandular disintegration and phagocytic cell infiltration. Apart from this, a weak signal was seen in luminal epithelial cells in normal looking colon mucosa in most specimens.

Weak signals for laminin chains α-1, γ-1, and γ-1 mRNAs were detected in cancerous areas of the 6 colon cancers studied for the expression of these genes. The expression of each of the three genes showed a similar distribution. Expression in stromal cells with a fibroblast-like morphology as well as in endothelial cells of smaller vessels was consistently found. In marked contrast to the γ-2 chain expression in the same samples, expression of α-1, β-1, or γ-1 was never found in cancer cells and no correlation between expression of α-1, β-1, and γ-1 chains with sites of invasion was found. Adjacent normal-looking parts of the samples were negative or only weakly positive for these laminin chains.

FIG. 1 shows in situ hybridization of a specimen of colon adenocarcinoma for γ-2 chain mRNA using a S-35 labeled anti-sense RNA probe derived from plasmid pbb2r-02. FIG. 1A is a cluster of heavily labeled cancer cells at the invasive front (open arrow) in close proximity to a well-differentiated glandular structure (straight arrow). FIG. 1B shows a high-magnification view of the area at the open arrow in 1A. Note that the isolated cancer cells show prominent labeling, whereas many coherent cancer cells of an adjacent glandular structure are negative (straight arrow). FIG. 1C shows the same pattern at an invasive focus in another part of the same specimen. FIG. 1D shows strong γ2 chain expression in cancer cells engaged in a bifurcation process (curved arrows). The malignant glandular epithelium from which the γ-2 chain-positive cancer cells are branching is negative (straight arrow). Magnification: 1A×100; 1B–1D×640.

Ductal Mammary Carcinomas

Six of the seven cases showed a prominent signal for γ-2 chain in a small subpopulation of cells intimately associated with invasively growing malignant glandular structures. The most prominent signal was seen in cells located at the border between malignant and surrounding stromal tissue in glandular structures that exhibited clear histological signs of active invasion (FIG. 2A). On careful examination it was concluded that the majority of the positive cells were cancer cells but it was not possible to determine if the cells of myoepithelial origin were also positive in some cases. One case was totally negative. Normal-appearing glandular tissue was negative in all cases.

Weak signals for laminin chains α-1, β-1, and γ-1 mRNAs were detected in fibroblast-like stromal cells throughout cancerous areas in one of the cases.

Malignant Melanoma

In all three cases strong hybridization of γ-2 chain was found in a population of cancer cells in the radial growth phase (FIG. 2B). Laminin chains α-1, β-1, and γ-1 were weakly expressed in the endothelium of small vessels and in fibroblast-like stromal cells throughout the affected areas in the two cases studied for these components. In addition, a weak signal for these chains was seen in sebaceous glands of adjacent normal skin.

Squamous Cell Carcinomas

In all four squamous cell carcinomas investigated, the same pattern of γ-2 chain expression was found as in other carcinomas. The signals were found only in cancer cells, and only in areas with signs of ongoing invasion (FIG. 2, C-G).

The four cases were also studied for MRNA of α-1, β-1, and γ-1 chains. In the two skin cancers, it was found that a very weak signal occurred in malignant cells, and that the weak signal was in all cancer cells and of an equal intensity.

This is in clear contrast to the pattern of expression of the γ-2 chain. As seen in melanomas, epithelial cells of sebaceous glands present in adjacent unaffected skin were weakly positive for these laminin chains. In the other two cases (cervix and vulva) weak expression of α-1, β-1, and γ-1 chains were seen only in endothelial and fibroblast-like stromal cells throughout the cancerous areas (FIG. 2F).

Figure 2:
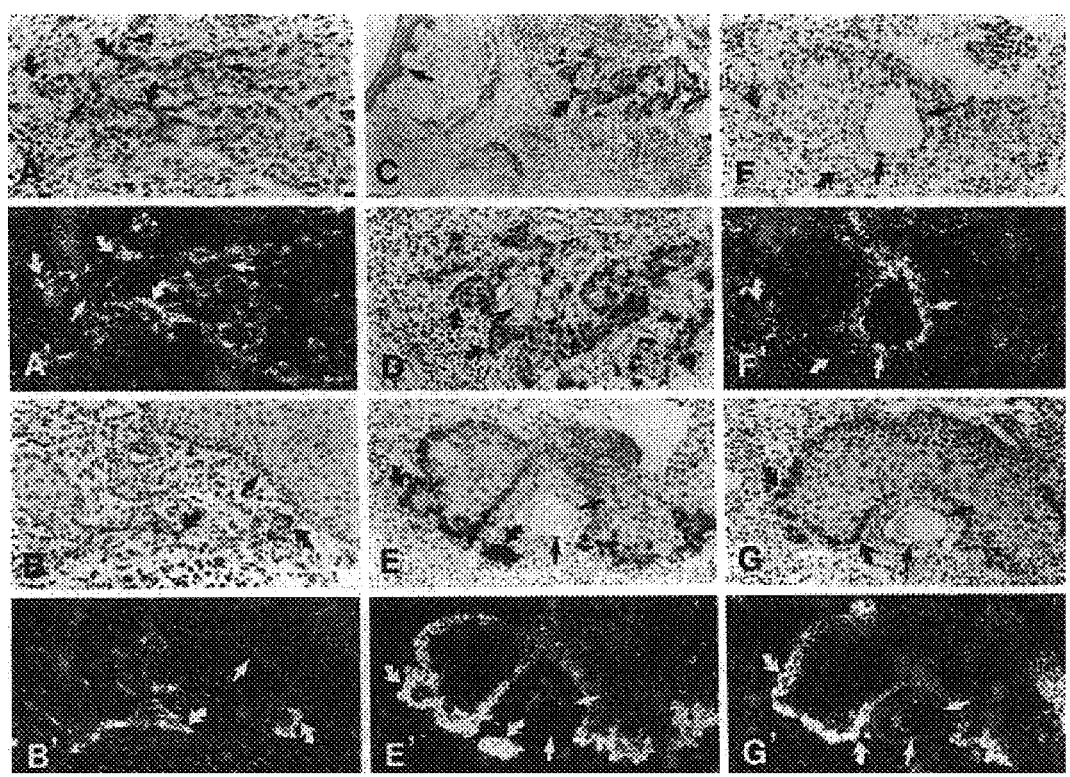
FIGS. 2A–G shows in situ hybridization for γ-2 chain mRNA on sections of ductal mammary carcinoma (2A), malignant melanoma (2B), squamous cell carcinoma of the skin (2C, 2D), and squamous cell carcinoma of the vulva (2E–2G). Magnification: 2C×100, all others ×640. Photos marked by plain letter i.e., X, show in situ hybridization results for γ-2 chain mRNA on stained sections. Photos marked by the letter +1, i.e., X–1, are the dark field images of the respective photomicrographs.

FIG. 2 shows In situ hybridization for γ-2 chain mRNA on sections of ductal mammary carcinoma (2A), malignant melanoma (2B), squamous cell carcinoma of the skin (2C–2D), and squamous cell carcinoma of the vulva (2E–2G). In 2A, cancer shows prominent signal for γ-2 chain mRNA in cells bordering the zone between malignant glandular tissue and surrounding mesenchyme (curved arrows). Cancer cells located more centrally in individual malignant glandular structures are negative for γ-2 chain mRNA (straight arrows). Note the wedge shaped form of the invading glandular tissue. (All images marked X' are dark-field images of the respective sections). FIG. 2B shows γ-2 chain mRNA signal in a subpopulation of cancer cells of radially growing malignant epithelium (curved arrows). Adjacent malignant epithelium showing a different growth pattern is devoid a signal (straight arrow). FIG. 2C shows γ-2 chain mRNA containing cancer cells at the invasive front (curved arrow). Note lack of signal in non-invasive areas of the tumor and in adjacent unaffected areas (straight arrow). FIG. 2D is a higher magnification of area of curved arrow of 2C highlighting the prominent signal in invading cells (curved arrow). Adjacent cancer cells with tumor islets are negative (straight arrow). FIG. 2E shows a strong signal for γ-2 chain mRNA is seen in invading cancer cells, using an anti-sense RNA probe derived from plasmid pb2t-03 (curved arrow). A postcapillary venule is negative (straight arrow). FIG. 2F is a near adjacent section hybridized for laminin γ-1 chain. Note that the endothelial cells of the venule show signal (straight arrow) whereas the malignant epithelium is negative (curved arrow). FIG. 2G is another near-adjacent section which was hybridized for γ-2 chain expression using an anti-sense RNA probe derived from a cDNA plasmid non-overlapping with that used for preparing the probe in 2E (phb2t-05). Note that the hybridization pattern is similar to that seen in 2E, with strong signal in invading cancer cells (curved arrow) and absence of signal in a vessel (straight arrow). Magnification: 2C×100, all others×640.

Sarcomas

All six sarcomas tested in the study were totally negative for γ-2 chain mRNA. The expression of other laminin chains was not tested.

Mouse Wounded Skin

Figure 3:
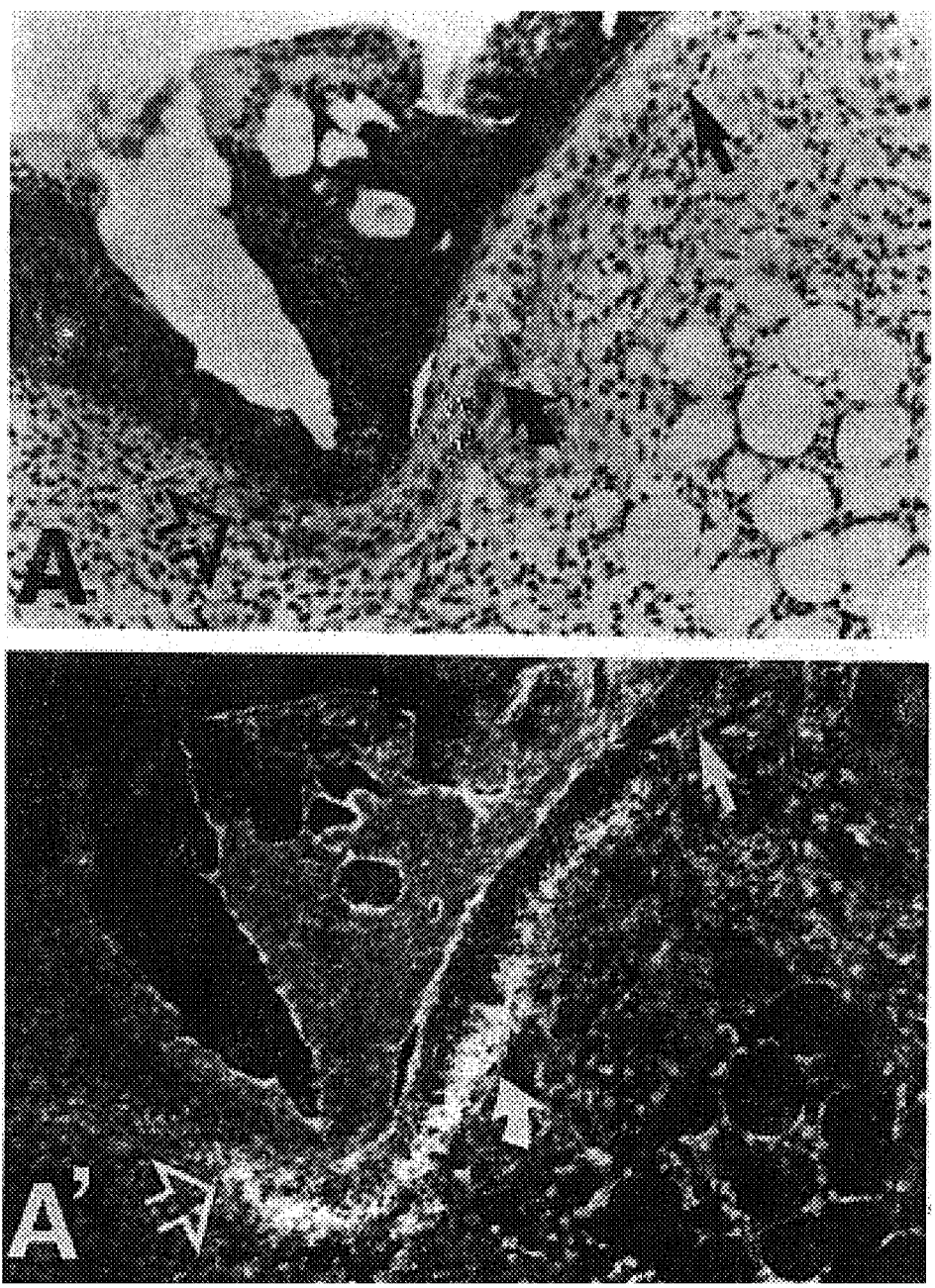
FIGS. 3A, A-1 is incisionally wounded mouse skin (72 hours after wounding) showing signal for γchain in keratinocytes at the leading edge of the migrating epithelium (curved arrow). Magnification: ×640.

To compare the gene expression of γ-2 chain in cancer tissue with a nonmalignant condition known to contain actively migrating epithelial cells showing a transient invasive phenotype, we hybridized sections of incisionally wounded mouse skin with γ-2 chain sense and anti-sense RNA probes. Weak γ-2 chain expression was observed in the keratinocytes at the edge of 12-hour old wounds, and at later time points (1–5 days), strong signals for γ-2 chain mRNA was seen exclusively in the basal keratinocytes of the epidermal tongue moving under the wound clot (FIG. 3). In adjacent normal-looking skin, keratinocytes were negative for γ-2 chain mRNA.

FIG. 3 is incisionally wounded mouse skin (γ-2 hours after wounding) showing signal for γ-2 chain in keratinocytes at the leading edge of the migrating epithelium (curved arrow). Whereas buccal keratinocytes located more distant to the site of injury show little or no signal (straight arrow). Note that the signal for γ-2 chain stops at the tip of invading keratinocytes (open arrow). A' is a dark field image of 3A. Magnification: ×640.

RNAse Protection Assay

Plasmid phbt-03 was linearized with EcoRI and a radiolabeled RNA-anti-sense probe was prepared by transcription using .sup.32 P UTP and T3 polymerase (Pyke et al., FEBS Letters, 1993, 326:69–75). RNAse protection assay, using 40 µg ethanol-precipitated and DNAse µI-treated total RNA from six samples of colon adenocarcinomas was performed as described in Pyke et al., (1993, supra.). Protected mRNA regions were analyzed on a denaturing polyacrylamide gel and autoradiography.

The RNAse protection assay carried out on total RNA from the six samples confirmed the presence of genuine γ-2 chain mRNA in all samples.

These results clearly demonstrate the important correlation of γ-2 chain expression and invasive cell phenotype in vivo, as detected in vitro. Thus the instant methods present a novel and important method for the specific identification of invasive cell phenotypes in biopsied tissues. The knowledge of any information diagnostic for the presence or absence of invasive cells is useful for the monitoring and prognosis of continuing anti-carcinoma therapies. Further the identification of the expression or non-expression of the γ-2 chain provides important information as to the phenotypic nature of the tissue examined. Thus the instant example demonstrates the use of probes of γ-2 chain for detection of the presence, or absence, of invasive cells.

EXAMPLE 4

The following example demonstrates the functional aspects of laminin-5, including the γ-2 chain of laminin-5, on cell adhesion and cell migration.

Materials and Methods

Cells and Cell Culture—A mouse squamous cell carcinoma cell line, KLN-205 (cat. no. ATCC CRL-1453), was obtained from American Type Culture Collection (Rockville, Md.). The cells were maintained as monolayer cultures in Eagle's minimum essential medium (MEM) containing non-essential amino acids and Earle's BSS supplemented with 10% fetal calf serum (FCS). The HaCat human keratinocyte cell line was a kind gift from Dr. Fuzenig (Heidelberg, Germany). The HaCat cells were cultured in Dulbecco's MEM supplemented with 10% FCS. However, when the cells were cultured for the production of laminin-5, the medium was replaced by serum-free medium. Preparation of Proteins—Mouse EHS laminin (laminin-1) was obtained from GIBCO BRL. Fibronectin was purified from FCS using a gelatin-Sepharose 4B column (Sigma) as described elsewhere (Vuento, M. & Vaheri, A. (1979) Biochem. J. 183: 331–337.34. Gillies, R. J., Didier, N. & Denton, M. (1986) Anal. Biochem. 159: 109–113). Human laminin-5 was immunoaffinity purified from the media of HaCat cells cultured for three days in the absence of serum. Briefly, the medium was first passed through a 5 ml gelatin-Sepharose column (Sigma, St. Louis, Mo.) to ensure the complete absence of fibronectin from the protein preparation, after which the medium was passed through a 10 ml anti-laminin γ2-Sepharose affinity column in order to bind laminin-5 molecules. Both columns were equilibrated in phosphate-buffered saline. The anti-laminin γ2-Sepharose affinity column was prepared by coupling a Protein A-purified anti-γ2 IgG (8 mg/ml) to 10 ml of CNBr-activated Sepharose (Pharmacia, Uppsala, Sweden). The anti-γ2 IgG was purified from a rabbit polyclonal antiserum prepared against a GST-fuision protein containing part of the short arm (domain III) of the γ2 chain (Pyke, C., Salo, S., Ralfkiaer, E., Romer, J., Dano, K. & Tryggvason, K. (1995) Cancer Res. 55: 4132–4139). The laminin-5 was eluted from the immunoaffinity column using 50 mM triethanolamine, pH 11.25, 0.1% Triton X-100 and neutralized directly with 1 M Tris-HCl, pH 7.0. Collected fractions were analyzed by SDS-PAGE and Western blotting using the same polyclonal antibodies as used for the preparation of the affinity column. Fractions containing laminin-5 were pooled and dialyzed against 50 mM Tris-HCl, 0,1 M NaCl, pH 7.4. Some batches of laminin-5 were denatured with 5 M urea and renatured to study the effects of the treatment on adhesion and migration properties.

Generation of Recombinant Baculovirus and Expression of Recombinant Laminin γ2 Chain—The γ2 chain of laminin-5 was expressed as recombinant protein using the baculovirus system and purified for studies on its functional properties. A full-length human laminin γ2 chain cDNA containing 6 bp of the 5' UTR and 822 bp of the 3' UTR was constructed from four overlapping cDNA clones L52, HT2-7, L15 and L61 (Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693). The resulting 4,402 bp cDNA was analyzed by restriction enzyme mapping and partial sequencing, and cloned into the pVL1393 recombinant transfer plasmid prior to transfer into the AcNPV-γ2 baculovirus vector kindly provided by Max Summers (Texas A&M University). This baculovirus vector containing the human laminin γ2 chain cDNA under the transcriptional control of the polyhedrin promoter was produced and purified following standard procedures (Summers, M. D. & Smith, G. E. (1987). A manual of methods for baculovirus vectors and insect cell culture procedures. Texas agricultural experiment station bulletin no. 1555, Collage Station, Tex.), except that it was first enriched according to the method of Pen et al. (Pen, J., Welling, G. W. & Welling-Wester, S. (1989). Nucl. Acid. Res. 17: 451) from the virus containing medium obtained by co-transfecting Sf9 cells with the wild-type virus (AcNPV) DNA and the recombinant transfer vector pVL1393-γ2. For expression of the recombinant protein, High Five (H5) cells were infected with the recombinant virus at a multiplicity of infection (MOI) of 5–10 pfu per cell by using the standard protocols (Summers, M. D. & Smith, G. E. (1987)).

The recombinant γ2 chain was purified by first resuspending the cells in 10 volumes of 50 mM Tris-HCl, pH 7.4, 100 mM NaCl, 2.5 mM EDTA, 1% Triton X-100, 1 mM PMSF and 1 mM NEM followed by homogenization in a Dounce homogenizer. The protein was extracted for 60 min on ice and solubilized proteins were removed by centrifugation at 1500×g for 10 min at 4° C. The pellet was extracted again with buffer containing 1–3 M urea. The recombinant γ2 chain was extracted with a buffer containing 5 M urea, and renatured by dialysis against 50 mM Tris-HCl, pH 7.4, 100 mM NaCl.

Preparation of Antibodies—Polyclonal antiserum against domain III of the laminin γ2 chain was prepared and characterized as described previously. Briefly, rabbits were immunized s.c. four times using a γ2-GST fusion protein as antigen. The antigen contained 177 amino acid residues (res. #391-567) from domain III of the γ2 (Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693). Antibodies against the GST-epitopes were removed from the antisera by negative immunoadsorption with GST-Sepharose made by coupling E. coli expressed GST protein to CNBr-activated Sepharore. The removal of anti-GST IgG was ensured by Western blotting analysis with GST-specific antibodies (data not shown). The specificity of the antibody against the laminin γ2 chain was also tested by Western blotting as well as by ELISA.

Polyclonal antibody against the C-terminus of the laminin γ2 chain was produced in rabbits essentially as above for domain III using a γ2-GST fusion protein as antigen. The antigen contained 161 amino acids (res. #1017-1178) from domain I/II of the γ2 chain and antibodies against the GST-epitopes were removed from the antisera by negative immunoadsorption with GST-Sepharose. The specificity of the antibody was tested by Western blotting and ELISA.

Polyclonal antiserum against laminin-1 was a kind gift of Dr. Foidart (University of Liege, Belgium). Normal rabbit serum was obtained prior to immunization from the rabbits used for immunization. IgG from the laminin-1 and laminin γ2 chain antisera, as well as from normal rabbit serum, was purified using Protein A Sepharose (Pharmacia, Uppsala, Sweden).

Cell Adhesion Assay—Microtiter plates (96 wells: Nunc, Copenhagen, Denmark) were coated with 100 μg/well of of laminin-1 (10 μg/ml), laminin-5 (10 μg/ml), or recombinant laminin γ2 chain (10 μg/ml) in PBS or 50 mM Tris-HCl, pH 7.4 by incubating the plates overnight at 4° C. Control wells were uncoated or coated with the same amounts of BSA. In some experiment the proteins were first denatured by dialysis overnight against 5 M urea, 50 mM Tris-HCl, pH 7.5 and then renatured by dialysis against 50 mM Tris-HCl, pH 7.5. Potential remaining active sites on the plates were blocked with 150 μl of 10 mg/ml BSA in PBS for 2 hours at room temperature. The wells were washed with PBS, and 100 ml of Eagle's MEM containing 5 mg/ml BSA was added. For the adhesion assays, KLN-205 cells were detached from subconfluent cell culture dishes with trypsin-EDTA (0.25%–0.03%) and resuspended in Eagle's MEM/BSA (5 mg/ml) at a concentration of 2×105 cells/ml and allowed to recover for 20 min at 37° C. A total of 20,000 cells were then added to each well and allowed to attach for additional 90 min at 37° C. The extent of cell adhesion was determined by measuring color yields at 600 nm, following fixation with 3% paraformaldehyde and staining with 0.1% crystal violet (Gillies, R. J., Didier, N. & Denton, M. (1986) Anal. Biochem. 159: 109–113). For inhibition assays with the anti-γ2 antibody, the substrate coated wells were incubated with 20 μg/ml of anti-γ2 chain IgG in PBS for 60 minutes prior to incubations with the cells.

Migration assay—The effect of endogenous laminin-5 on migration of KLN-205 cells was determined by using a modified Boyden chamber assay, as described by Hujanen and Terranova (Hujanen, E. & Terranova, V. P. (1985) Cancer Res. 45: 3517–3521), and the effect of exogenous laminin-5 by using a modified Transwell assay, as described by Pelletier et al. (Pelletier, A. J., Kunicki, T. and Quaranta, V. (1996). J Biol Chem 271: 1364).

The Boyden chamber assay was briefly carried out as follows. Polycarbonate filters (pore size 10 μm, diameter 12 mm; Costar, Cambridge, Mass.) were coated with 2.5 μg of EHS type IV collagen, and used to separate the upper and lower compartments of the 50 μl chamber. A total of 1×10$^5$ cells in Eagle's MEM containing 0.1% BSA were placed in the upper compartment, and the lower compartment was filled with medium with or without chemoattractants (50 μg/ml laminin-1 or fibronectin). To study the effect of the laminin γ2 chain antibodies on cell migration, anti-γ2 (III) IgG or anti-γ2 (C-term) IgG was added to the upper compartment together with the cells at a concentration 20 μg/ml. Normal rabbit IgG was used as negative control. After 8 hour incubation at 37° C. in a humidified atmosphere, the filters were removed, fixed and stained (Diff-Quick, Baxter Diagnostics, Tubingen, Germany). The cells that had not migrated were removed from the upper surface of the filter with cotton swabs. Migration of cells was quantified by counting the cells on the lower surface of each filter in 10 randomly selected high power fields (×400). All assays were performed in triplicates.

The "Transwell" plate assay (Transwell plates with pore size 12 µm, diameter 12 mm; Costar, Cambridge, Mass.) was used to determine the effect of exogenous laminin-5 on cell migration. The lower side of the membrane was coated with 2.5 µg of EHS type IV collagen for 3 hours at room temperature. Both side were blocked with 1% bovine serum albumin for 1 hour. A total of 1×10$^5$ cells were added per well in the upper compartment in Eagle's MEM containing 10% FCS, and the lower compartment was filled with 2.5 µg/ml laminin-5 as a chemoattractant. Antibodies against the C-terminus and domain III of the γ2 chains or nonimmune IgG were added to the upper compartment, together with the cells at a concentration 20 µg/ml. Following a 16 hour incubation at 37° C. the cells were fixed and stained with Diff-Quick. Cells on the top surface of the membrane were removed with cotton swabs, and cells that had migrated to the lower side of the membrane were counted (12 fields +/− S.D.)

Preparation of LAMC2-lacZ Reporter Gene Constructs—Two different segments of the LAMC2 5' flanking regions were subcloned into a pKK2480 vector containing the β-galactosidase gene and the SV40 polyadenylation signal (kind gift from Mikkel Rohde, Aarhus, Denmark) for expression in transgenic mice. The longer construct, pHH-1, contained 5946 base pairs (−5,900 to +46) and the shorter construct contained a total of 668 base pairs (−613 to +55). Briefly, the 5' end of the pHH-1 insert was made by ligating a 3,900 base pair HindIII-PstI fragment and a 1,150 base pair PstI fragment of genomic clone P14 (Airenne, T., Haakana, H., Sainio, K., Kallunki, T., Kallunki, P., Sariola, H. & Tryggvason, K. (1996) Genomics 32: 54–64). The 3' end of the construct was a PstI-SalI fragment (−699 to +46) made by PCR and ligated to the 5' end 5,050 base pair fragment. The full length fragment was blunt ended with Klenow and subcloned into the pKK2480 vector. The shorter construct pHH-2 was made by PCR from genomic clone P14, digested with SalI and XbaI and subcloned into pKK2480. All PCR made segments were sequenced to ensure that no sequence errors existed. Both constructs could be released from the vector with XhoI and EagI.

Generation and Analyses of Transgenic Mice—The plasmids pHH-1 and pHH-2 were digested with EagI and XhoI to release the inserts from the vector. Transgenic mice were produced by pronuclear microinjection of (C57B1/6+DBA/2)F1 fertilized oozytes as described elsewhere (Hogan, B., Constantini, F. & Lacy, E. (1986) Manipulating the mouse embryo: A Laboratory Manual. Cold Spring Harbor, N.Y.). Founder animals were identified by PCR analysis (Hanley, T. & Merlie, J. P. (1991) BioTechiniques 10: 56) or Southern blotting of genomic DNA isolated from the tail. Positive founder mice were mated with wild-type hybrid (C57B1/6+DBA/2)F1 mice to yield transgenic lines. Expression of the lacZ gene was detected by staining with X-gal (5bromo-4-chloro-3-indolyl-b-D-galactopyranodide) as a substrate (Behringer, R. R., Crotty, D. A., Tennyson, V. M., Brinster, R. L., Palmiter, R. D. & Wolgemuth, D. J. (1993) Development 117: 823–833).

Preparation of Tissues for Immunostaining and Staining for β-Galactosidase Activity—For immunohistochemical analyses, mouse tissues were fixed in 4% paraformaldehyde and embedded in paraffin. For analyses of β-galactosidase expression, whole embryos and postnatal tissues were fixed in 0.2% glutaraldehyde, 2% paraformaldehyde in 0.1 M phosphate buffer, pH 7.3, for 60 min at 4° C. washed three times for 30 min with a 7.3 pH 0.1 M phospate buffer containing 0.1% sodium deoxycholate, 2 mM MgCl2 and then stained with X-Gal (1 mg/ml X-Gal, 5 mM K-ferricyanide, 5 mM K-ferrocyanide) before embedding in paraffin. Experimental wounds were made to transgenic mice by small cutaneous incisions, the wounds were closed by a single suture, and the wounds surrounded by normal skin were removed surgically after three and seven days and processed for staining.

Immunohistochemical Staining—Five µm thick paraffin sections were stained with polyclonal antibodies against laminin-1 or the γ2 chain of laminin-5. In brief, the paraffin sections were first incubated with 0.4% pepsin in 0.1 M HCl at 37° C. for 20 min to expose the antigens, blocked for nonspecific binding with 5% newborn rabbit serum, 0.1% BSA, and then incubated for 1 h at 37° C. with the polyclonal IgG diluted in TBS to 5–10 µg/ml. Subsequently, a biotinylated swine-anti-rabbit antibody was applied, followed by incubation with a 1:400 dilution of Horseradish-Peroxidase-Avidin-Biotin-Complex (DAKO, Copenhagen, Denmark). The color was developed in diaminobentsamidine (DAB), followed by counterstaining of the slides with hematoxylin.

Results

Characterization of Proteins and Epithelium-Derived Cells—Immunopurified trimeric laminin-5, isolated from the culture medium of HaCat cells contained two major bands when analyzed by SDS-PAGE (FIG. 1). These bands corresponded, respectively, to the 165 kDa α3 chain, and the 155 kDa and 140 kDa γ2 and β3 chains migrating as a single band, as reported previously (Carter, W. G., Ryan, M. C. & Gahr, P. J. (1991) Cell 65: 599–610; Rousselle, P., Lunstrum, G. P., Keene, D. R. & Burgeson, R. E. (1991) J. Cell Biol. 114: 567–576; Pikkarainen, T., Schulthess, T., Engel, J. and Tryggvason, K. (1992) Eur. J Biochem. 209, 571–582). Additionally, a weak band of about 105 kDa corresponding to the processed γ2 chain could be observed.

Figure 5:
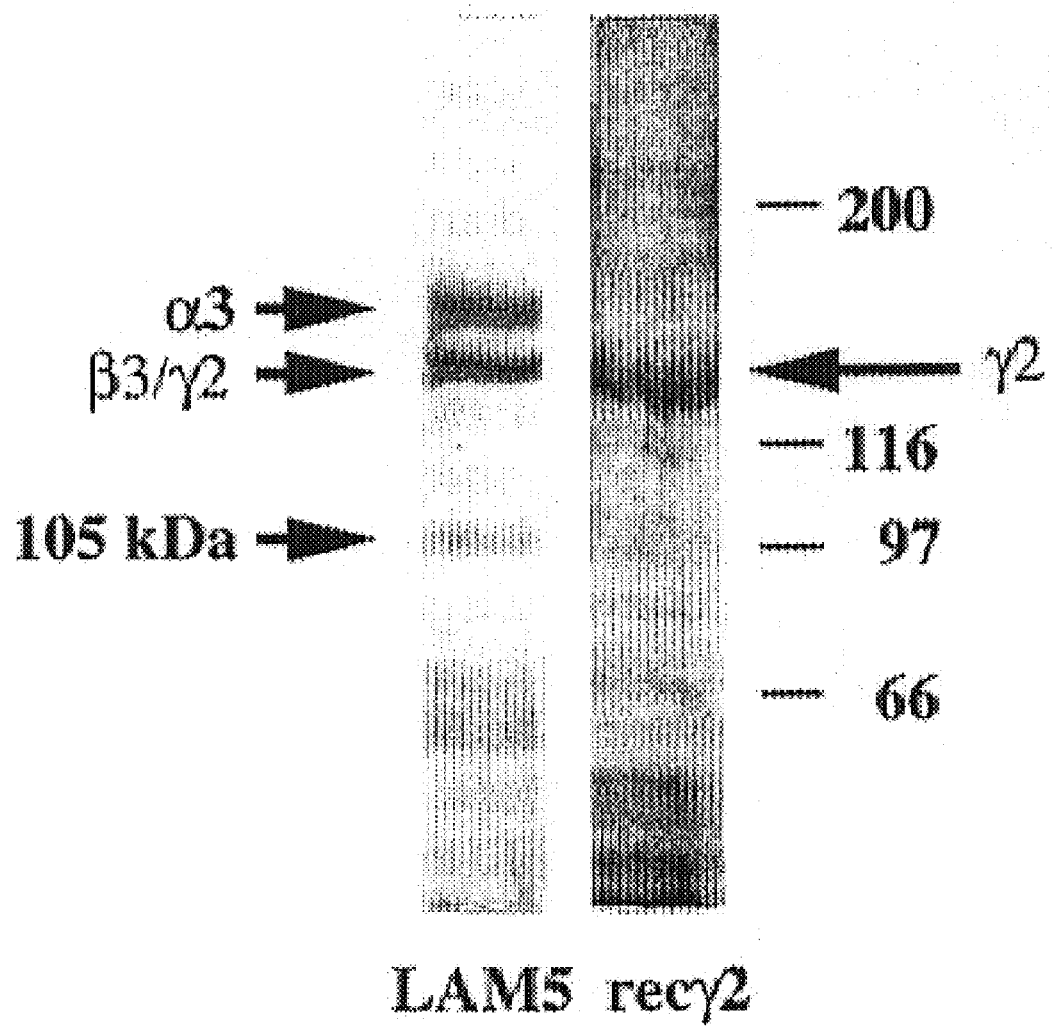
FIG. 5. Characterization of laminin-5 and recombinant laminin γ2 chain prepared and used in this study. HaCat cell culture medium proteins and the recombinant laminin γ2 chain extracted from baculovirus-infected insect cells were purified as described in *Materials and Methods* and studied on 6% polyacrylamide gels. (A) Silver stained laminin-5 (LAM5) from HaCat cells was resolved into two major bands of 165 kDa and 140–155 kDa. Additionally, a weak band of 105 kDa could be observed. These bands correspond in size to those of the α3 (165 kDa), γ2+β3 (155 kDa+140 kDa) and processed γ2 (105 kDa) chains of laminin-5. The recombinant γ2 chain (recγ2) produced by the baculovirus system showed a major silver stain band of about 155 kDa).

Full-length human recombinant laminin γ2 chain was produced in High-5 *Spodoptera frugiperda* insect cells using the baculovirus system. Since the γ2 chain was not secreted to the culture medium, possibly because it was not assembled intracellularly into a normal heterotrimer, it was isolated from the cell fraction as described in *Materials and Methods*. The protein was extracted under denaturating conditions using 5 M urea, renatured by extensive dialysis against 50 mM Tris-HCl, 100 mM NaCl, pH 7.4, and purified. The purified recombinant γ2 chain was full length and highly pure as determined by SDS-PAGE analysis (FIG. 5).

The HaCat human keratinocytes and mouse KLN-205 squamous carcinoma cells were shown to express laminin-5, based on northern analyses and immunostaining, using a cDNA probe (Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693) and/or polyclonal antibodies specific for the γ2 chain (Pyke, C., Salo, S., Ralfkiaer, E., Romer, J., Dano, K. & Tryggvason, K. (1995) Cancer Res. 55: 4132–4139), respectively. Furthermore, the KLN-205 cells developed γ2 chain positive primary tumors and metasases in mice in vivo (data not shown). Following intramuscular or subcutaneous inoculations, large primary tumors developed in 4 weeks with numerous lung metastases after 4–6 weeks. KLN-205 cells injected into the tail vein produced multiple lung tumors (experimental metastases) in four weeks. Consequently, both cell types were considered appropriate for the cell attachment and migration experiments carried out in this study.

Figure 6:
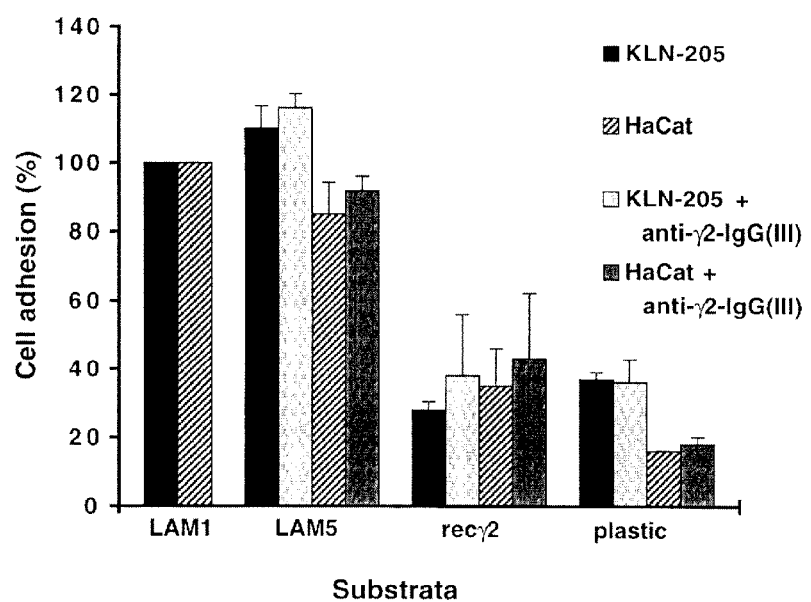
FIG. 6. Efficiency of human laminin-5 and recombinant human laminin γ2 chain for attachment of HaCat keratinocytes and KLN-205 squamous carcinoma cells in vitro. The attachment efficiency was compared with the efficiency with which the cells bound to laminin-1. Substrate concentrations (10 µg/ml) providing maximum attachment to laminin-1 and laminin-5 were used. The results are presented as means +/− SD calculated from at least four duplicate series, the values for laminin-1 were given the arbitrary value of 100%.

Laminin-5 Molecule, but not Recombinant Laminin γ2 Chain, Promotes Cell Adhesion—The laminin-5 and recombinant γ2 chain prepared in this study, as well as commercial laminin-1, were used as substrata in attachment assays (FIG. 6) with the two epithelium derived HaCat and KLN-205 cell lines that both express laminin-5. Both cell lines attached about 2.5 times more readily to laminin-1 than to plastic. Adhesion of the cells to laminin-5 appeared to be slightly higher than that to laminin-1, but the differences were not statistically significant. The cells attached equally well to laminin-5 preparations denatured in 5 M urea and then renatured by dialysis against 50 mM Tris-HCl, 100 mM NaCl, pH 7.4, as described for the recombinant γ2 chain above, indicating that this treatment did not affect the binding properties of the trimeric molecule. The attachment to laminin-5 was not significantly decreased in the presence of two different polyclonal antibodies made against the short or long arms of the γ2 chain or pre-IgG. Different amounts of the antibody against the short arm of the γ2 chain were also tested (up to 50 μg/ml), but no effects on cell adhesion were observed. When the cells were plated on the recombinant γ2 chain alone, the attachment was not significantly higher than that to plastic, this attachment not being influenced by polyclonal antibodies against the γ2 chain. The data confirm previous results showing that trimeric laminin-5 promotes adhesion of epithelial cells, but the present results further strongly suggest that this adhesion is not mediated by the γ2 chain.

Antibodies Against Laminin γ2 Domain III, but not Domain I/II, Inhibit Cell Migration—Immunohistochemical and in situ hybridization studies on healing skin wounds have indicated a role for laminin-5 in cell migration. The potential role of the γ2 chain of laminin-5 in this process was examined for the KLN-205 cells in vitro using Boyden and Transwell chamber assays as described in *Materials and Methods*.

Figure 7:
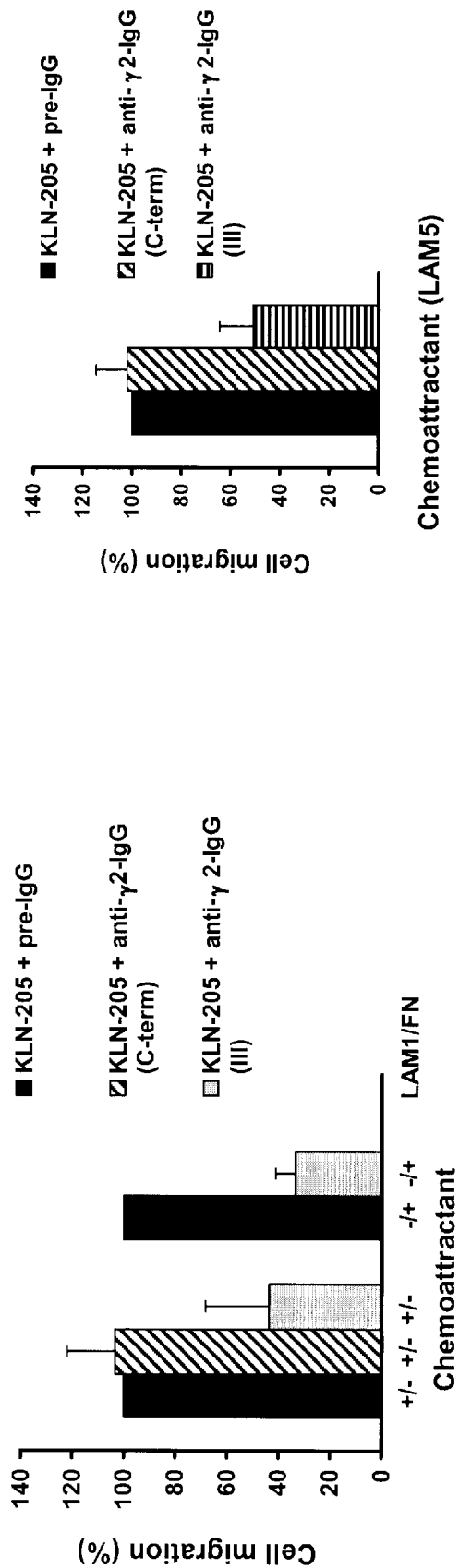
FIGS. 7A–B. Effects of polyclonal γ2 chain antibodies on the migration of KLN-205 squamous carcinoma cells in Boyden and Transwell chamber assays of migration. (7A) The two compartments of the chemotactic Boyden chambers were separated by a type IV collagen coated porous Nucleopore filter (pore size 8 µm). The cells (1×105) in MEM containing 0.1% BSA were placed in the upper compartment, and laminin-1 (+/−) or fibronectin (−/+) in MEM containing 0.1% BSA were added as chemoattractants to the lower compartment. IgG afainst γ2 chain domains III, I/II or preimmune IgG was added to the upper compartment with the cells at a concentration of 20 µg/ml. After 8-hour incubation at 37° C. the filters were removed and migration of cells to the lower surface of the filter were quantitated. The data are expressed as percentage of migrated cells (+/− SD (bars)) per high power field, setting migration in the presence of pre-immune IgG as 100%. Cells were counted in ten randomly selected high power fields to triplicate assays. (7B), Effects of exogenous laminin-5 on cell migration in a Transwell assay. The lower side of the membrane was coated with EHS type IV collagen, and the lower compartment was filled with 2.5 µg/ml laminin-5 as a chemoattractant. Pre-immune IgG, IgG against the γ2 chain domains III or I/II were added to the upper chamber containing the cells. Following 16 hour incubation the cells were fixed and cells at the lower side of the membrane were counted (12 fields +/− SD).

Migration was first studied in the Boyden chamber assay using laminin-1 and fibronectin in the lower chamber as chemoattractants. The cells were plated on type IV collagen coated filters separating the upper and lower compartments, and antibodies to different domains of the γ2 chain were added to the upper chamber. Migration of cells in the presence of preimmune IgG was arbitrarily set as 100% (FIG. 7). When polyclonal IgG against the short arm of the γ2 chain was added to the upper compartment containing the cells, the migration of cells through the filter was decreased to about 35 to 45% of that observed with the preimmune IgG (FIG. 7A). In contrast, the polyclonal IgG against C-terminal domain I/II did not affect migration of the cells (FIG. 7A).

The effects of the two antibodies were similarly used in the Transwell assay using native laminin-5 as chemoattractant in the lower compartment, and the results were essentially the same as above. Thus, addition of IgG raised against domain III of the γ2 chain inhibited the migration to about 50% as compared with preimmune IgG, while the polyclonal IgG against domain III did not affect the cell migration.

These in vitro results demonstrate that laminin-5 can have a role in the locomotion of epithelium-derived cells, and that this function can be inhibited by antibodies directed against domain III of the γ2 chain.

Figure 8:
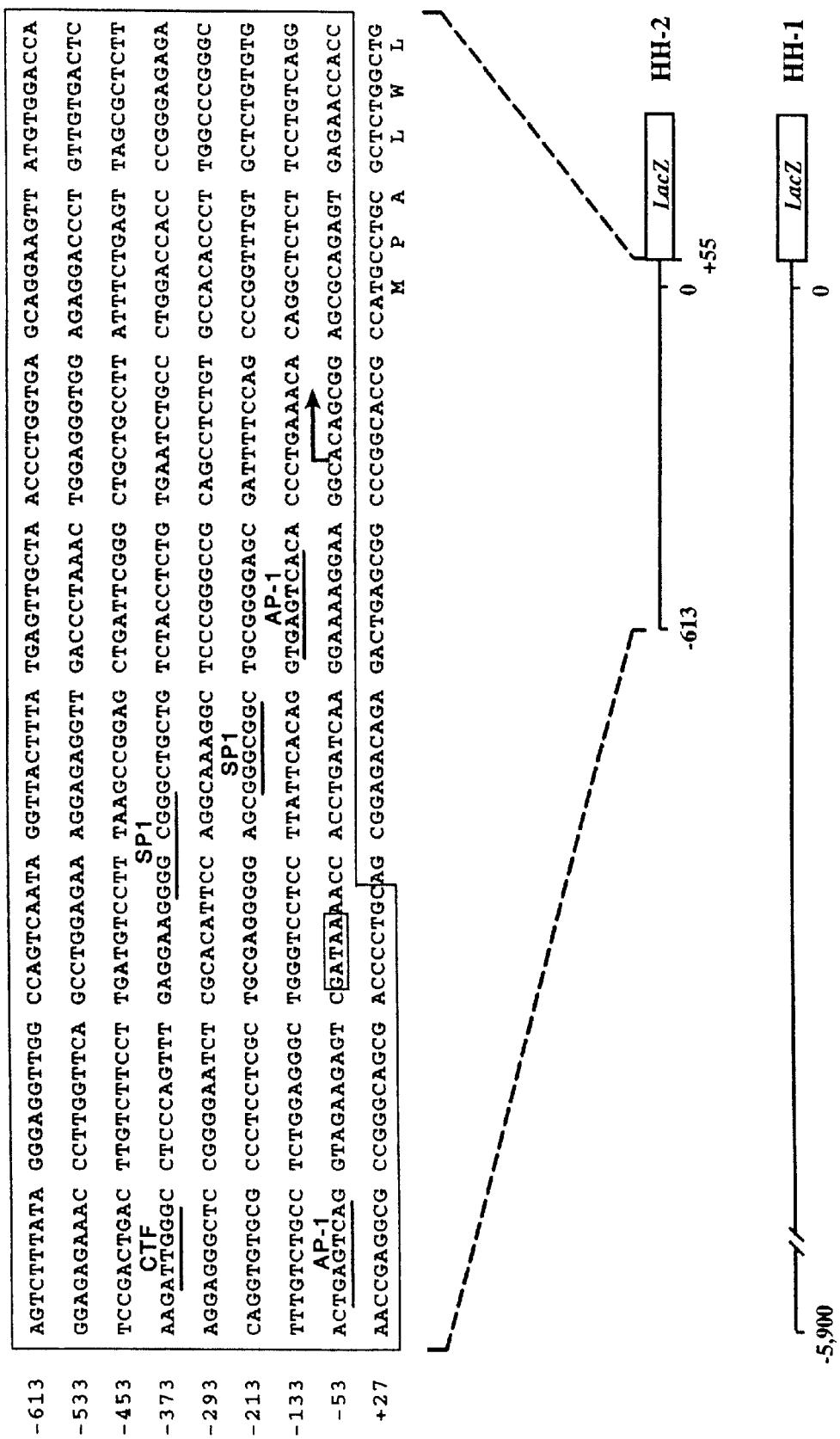
FIG. 8. LAMC2 Promoter-reporter gene constructs used for studies of expression in transgenic mice. Top, nucleotide sequence of the 5' region of the LAMC2 gene and its immediate upstream region (SEQ. ID. NO.:20). The bent arrow indicates the site of transcription inititation. The GATAA motif is boxed and the AP-1, Sp1 and CTF motifs are underlined. The translation initiator codon ATG in exon 1 for methionine is indicted by a double underline. The first amino acids of the protein are shown with the single letter code beneath the corresponding codons. The large boxed area represents the sequence cloned into construct HH-2. Bottom, schematic illustration of the two LAMC2-LacZ reporter gene constructs HH-1 and HH-2 used in transgenic mice.

Limited Expression of LAMC2 Promoter-Reporter Gene Constructs in Epithelial Cells in Transgenic Mice—In order to search for potential epithelium-specific enhancer elements in the LAMC2 gene, we made transgenic mice harboring DNA constructs containing varying lengths of the 5' flanking region of the LAMC2 gene connected with a downstream reporter gene, which in this case was LacZ coding for bacterial β-galactosidase (SEQ. ID. NO.: 20) (FIG. 8). Two different constructs were used for microinjection into pronuclei of fertilized mouse oozytes. The first construct HH-1 contained an about 5,900 bp HindIII-SalI fragment, including 55 base pairs from the 5' untranslated region and the 5' flanking region of the LAMC2 gene. The second construct, HH-2, contained 55 base pairs of the 5' untranslated region and 613 base pairs of the 5' flanking region. The sequence from the LAMC2 promoter region cloned into HH-2 (FIG. 8) contains a GATAA box starting 27 base pairs upstream of the transcription initiation site (Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693), and two AP1 binding sites immediately upstream. Additionally, there are two Sp1 binding sides and an inverted CTF sequence (CCAAT box) further upstream. Three founder lines were studied in detail for the expression pattern of HH-1, and two lines for that of construct HH-2. Both constructs yielded similar expression patterns for the β-galactosidase reporter gene.

Figure 9:
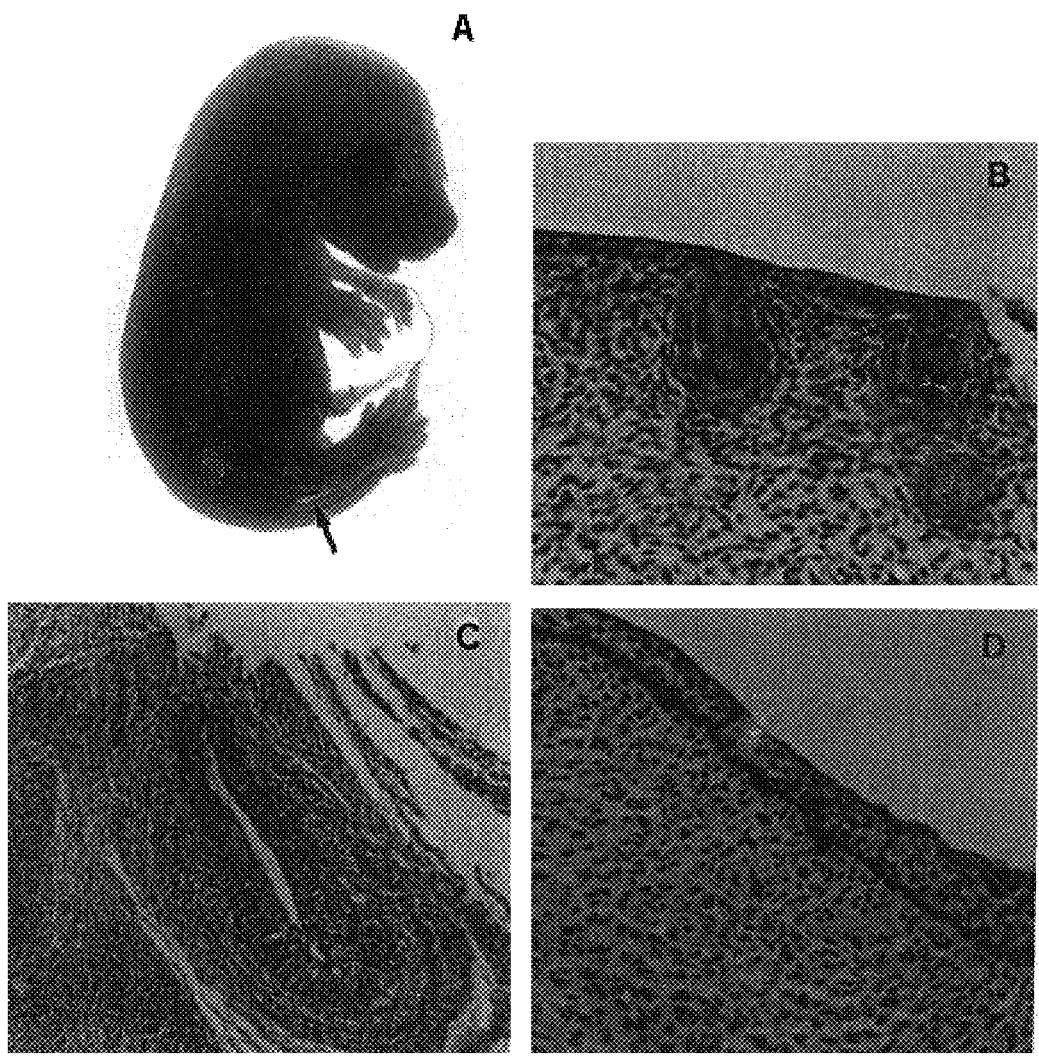
FIGS. 9A–D. Expression of LAMC2-LacZ reporter gene constructs in 15.5-day-old transgenic mouse embryos. (9A), Staining of the whole 15.5-day-old embryo reveals highly restricted expression of β-galactosidase as observed in some hair follicles and some regions of skin and testicles (arrow). Construct HH-2. (9B), Scattered epithelial cells of hair follicles are positive. Construct HH-1. (9C), Scattered positive epithelial cells of ductus deferens. Construct HH-1. (9D), Some positive epithelial cells of skin. Construct HH-2.

In mouse embryos very little expression was observed with both constructs. In 15.5-day-old whole embryos only some hair follicles, testicles and some regions of the skin showed positive reaction (FIG. 9A). Microscopic analysis revelad positive staining in scattered basal keratinocytes of skin and some epithelial cells of hair follicles and ductus deferens (FIG. 9B-D). Importantly, cells of all other epithelia were negative for expression. These results sharply contrast our previous results showing strong expression of the LAMC2 gene in epithelial layers, including those of skin, respiratory tract and kidney in human embryos as determined by in situ hybridization (Kallunki, P., Sainio, K., Eddy, R., Byers, M., Kallunki, T., Sariola, H., Beck, K., Hirvonen, H., Shows, T. B. & Tryggvason, K. (1992) J. Cell Biol. 119: 679–693). This shows that the reporter gene constructs made in this study did not contain the cis-acting elements necessary for epithelial expression, although the restricted expression observed was limited to only some epithelial cells.

Figure 10:
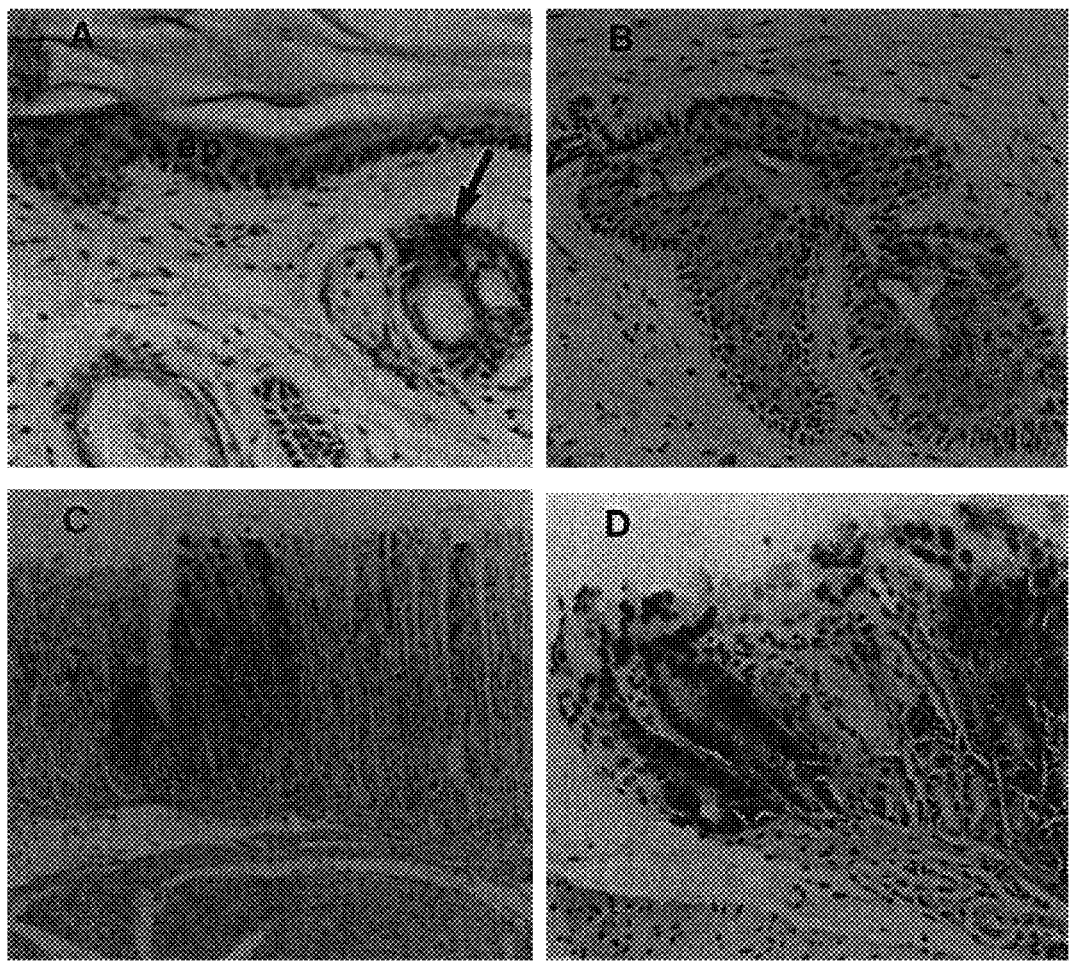
FIGS. 10A–D. Expression of shorter LAMC2-LacZ reporter gene construct HH-2 in adult transgenic mouse tissues. (10A), Regionally positive epithelial cells of the epidermis (ep) and hair follicles (arrow). (10B), Scattered positive epithelial cells in ductus deferens (10C and 10D), Expression can be seen in some areas of the gastric mucosa. Note that the expression can be localized to epithelial cells of both the surface and in the gastric pits.

Expression was also examined in tissues of adult transgenic mice harboring the two constructs. Both constructs yielded highly similar, but restricted expression in the embryos, whereas in the adult tissues the distribution of expression was slightly more extensive. Interestingly, as was the case for the embryos, the limited expression was confined to epithelial cells, i.e. cell types normally expressing only the LAMC2 gene in vivo. For example, in skin discontinuous expression was observed in keratinocytes of the epidermis and epithelial cells of some hair follicles (FIG. 10A). In the stomach intense expression could be seen in some villi of the gastric mucosa, but it was absent in most areas (FIG. 10B,C). In positive areas expression could be seen in surface epithelial cells and in cells of the gastric pits. As in the embryos expression was also observed in epithelial cells of the ductus deferens (FIG. 10D). However, epithelia such as those of the respiratory tracts normally showing strong expression in vivo did not show any expression at all in the present study.

Identification of a Cis-Element with Migration-Related Activity in the LAMC2 Gene in Transgenic Mice—The in vitro cell migration studies described above, together with previous morphological studies have indicated a role for laminin-5 in cell movement. These data imply that the genes for the subunits chains of this protein should have regulatory elements induced during cell migration. In order to further examine the association of cell migration with laminin-5 expression, we decided to initiate search for potential migration-related cis-acting elements in the two laminin γ2 chain gene promoter-LacZ reporter gene constructs, HH-1 and HH-2, using transgenic mice as a model system.

Figure 11:
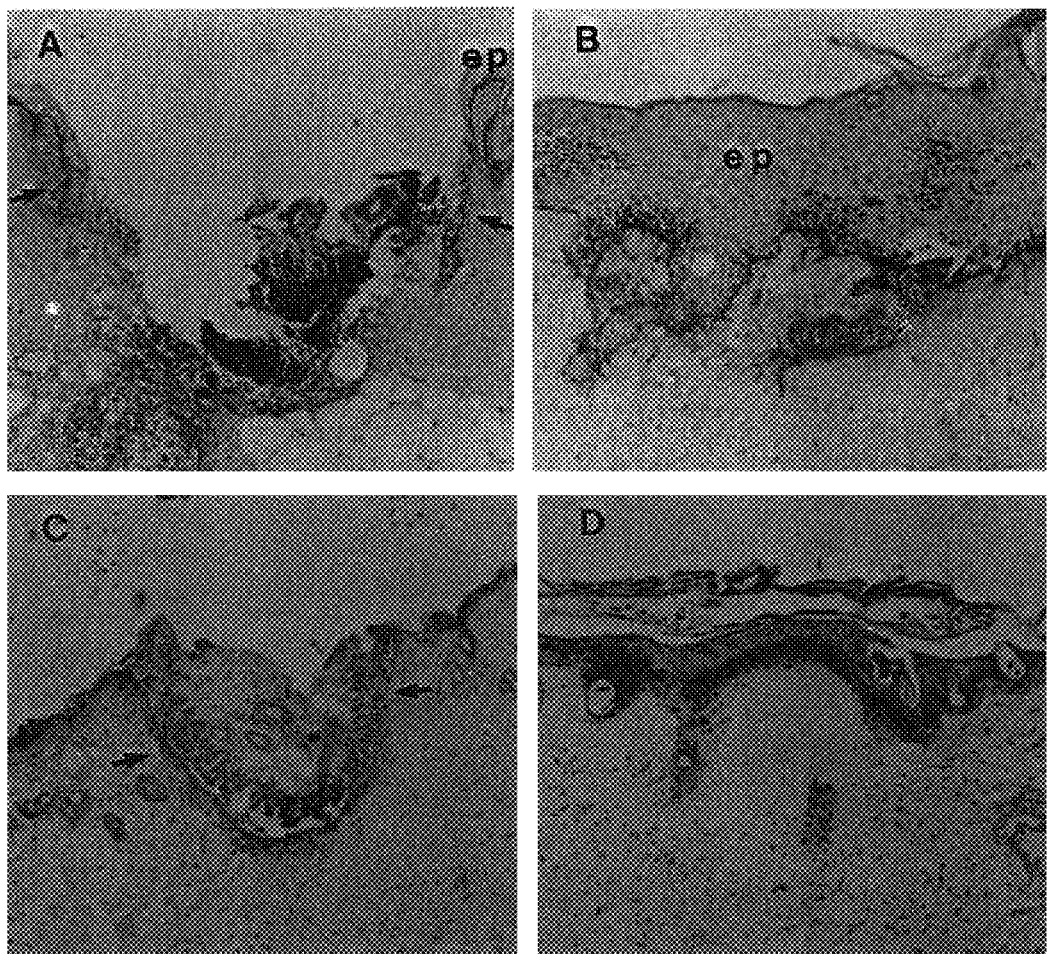
FIGS. 11A–D. Immunolocalization of laminin-5 γ2 chain and expression of LAMC2-LacZ reporter gene constructs in dorsal incision skin wounds in transgenic mice. (11A), Immunostaining localizes the γ2 chain to the basement membrane (arrow) beneath keratinocytes of the uninjured epithelium (ep) at the edges of the 3-day-old wound (11B), Immunostaining reveals the presence of the γ2 chain in the entire newly formed basement membrane deposited under the epithelium (ep) covering the 7-day-old incision wound. (11C), Expression of the LAMC2-LacZ reporter gene construct HH-2 in keratinocytes migrating from edges of the 3-day-old incision wound (arrows) during the initial phase of re-epithelialization. Only minor expression is observed in keratinocytes of the uninjured epithelium. (11D), Keratinocytes of the new epithelium covering the entire 7-day-old incision wound exhibit intense expression of the reporter gene.

As we have previously shown, the LAMC2 gene is expressed in keratinocytes migrating over a healing skin wound (Pyke, C., Romer, I., Kallunki, P., Lund, L. R., Ralfkiaer, E., Dano, K. & Tryggvason, K (1994) Am. J. Pathol. 145: 782–791). According to the present invention, small incision wounds were made into the dorsal skin and tails of mice made transgenic with the two constructs mentioned above to examine if the LacZ gene is expressed in migrating keratinocytes during wound healing. As can be seen in FIG. 11, immunostaining of the dorsal skin wound showed distinct linear staining for the laminin γ2 chain in the normal subepithelial basement membrane and also strong immunostaining for this chain beneath keratinocytes migrating over the healing wound could be seen. This confirms previous reports that laminin-5 is present in the normal epithelial basement membrane and also that the migrating keratinocytes express laminin-5. Staining with polyclonal antibodies against EHS tumor laminin-1 containing the α1, β1 and γ1 chains showed a weak staining of the subepithelial basement membrane as well as staining of basement membranes in blood vessels and muscle. Staining for expression of the two β-galactosidase reporter gene constructs showed intense staining in keratinocytes migrating over the healing wound (FIG. 11C,D), while no color reaction was noted in keratinocytes resting on a normal epithelial basement membrane. The staining was seen in several layers of keratinocytes indicating that the enhancer element(s) directs expression in proliferating and migrating keratinocytes. Identical patterns were obtained in mice made with both constructs, demonstrating that the element necessary for driving the expression is located within the 613 base pair region immediately upstream of the transcription site of the LAMC2 gene.

Thus, according to the present invention, intact laminin-5 effectively mediates attachment of epithelial cells. As set forth above in Example 4, the present invention utilized human keratinocytes and KLN-205 mouse squamous carcinoma cells, both of which were shown to express laminin-5. The effect of laminin-5 on adhesion was similar to that of laminin-1 isolated from the mouse EHS tumor. Both laminin isoforms have been shown to have similar adhesive properties. This adhesion is presumably mediated through α6β4 and α3β1 integrins that both bind to the long arm of the laminin molecule. However, there is also an indication that the short arm of the γ2 chain is also involved in the anchorage of epithelial cells, as an in-frame deletion mutation removing 73 amino acid recidues from domains III and IV of the short arm of the γ2 chain results in lethal (Herlitz) junctional epidermolysis bullosa. In determining whether this particular chain promoted cell adhesion adhesion studies were carried out using full-length recombinant human γ2 chain produced in insect cells using the baculovirus system. It has been shown by rotary shadowing that individually produced recombinant β1 and γ1 chains maintain apparent normal tertiary structure of the short arm (Pikkarainen, T., Schulthess, T., Engel, J. and Tryggvason, K. (1992) *Eur. J Biochem.* 209, 571–582), and, therefore, the tertiary structure of the short arm of the γ2 chain studied here was assumed to be normal and exposed. This recombinant chain did not show any significant effects on cell adhesion as compared with plastic. The recombinant chain was not secreted to the cell culture medium, presumably because it was not incorporated into a heterotrimeric molecule and, therefore, it needed to be purified from the cytosol under denaturing conditions, prior to renaturation. Although it is possible that this polypeptide chain lost its adhesive properties due to the denaturing conditions, it is not considered likely, as intact laminin-5, also denatured and renatured using the same conditions, maintained its adhesion activity. Furthermore, since it has been shown that recombinant laminin α chains (or their domains) produced in an eukaryotic expression system bind cellular receptors (Yurchenco, P. D., U. Sung, M. Ward, Y. Yamada & J. J. O'Rear (1993). J. Biol. Chem. 268: 8356–8365; Sung, U., J. J. O'Rear & P. D. Yurchenco (1993). J. Cell Biol. 123: 1255–1268; Colognato-Pyke, H., J. J. O'Rear, Y. Yamada, S. Carbonetto Y.-S. Cheng, & P. D. Yurchenco (1995). J. Biol. Chem. 270: 9398–9406; Colognato, H., M. MacCarrick, J. J. O'Rear & P. D. Yurchenco (1997). J. Biol. Chem. 272: 29330–29336), it was concluded that the recombinant γ2 chain analyzed in the present study also should be functional. Thus, according to the present invention, the short arm of the laminin γ2 chain does not bind to cellular receptors, and the important binding site lost in the above mentioned lethal skin blistering disease interacts with some protein(s) of the extracellular matrix. This explanation is plausible also because it has been shown that the E8 fragment of laminin-1 containing the distal portion of the triple coiled coil (long arm) and recombinant C-terminal G domain of the α1 and α2 chains contains the cell binding sites (Yurchenco, P. D., U. Sung, M. Ward, Y. Yamada & J. J. O'Rear (1993). J. Biol. Chem. 268: 8356–8365; Sung, U., J. J. O'Rear & P. D. Yurchenco (1993). J. Cell Biol. 123: 1255–1268; Colognato-Pyke, H., J. J. O'Rear, Y. Yamada, S. Carbonetto Y.-S. Cheng, & P. D. Yurchenco (1995). J. Biol. Chem. 270: 9398–9406; Colognato, H., M. MacCarrick, J. J. ORear & P. D. Yurchenco (1997). J. Biol. Chem. 272: 29330–29336 Aumailley, M., Nurcombe, V., Edgar, D., Paulsson, M. & Timpl, R. (1987) J. Biol. Chem. 262: 11532–11539). The laminin binding sites on the epithelial cells have later been assigned to the integrins α6β4 and α3β1. The conclusion that the short arm of the γ2 chain does not interact with cellular receptors was further supported by the present results showing that polyclonal antibodies raised against the short arm do not inhibit adhesion of cells to intact laminin-5.

Previous work has shown that expression of laminin-5 is upregulated in migrating keratinocytes of healing wounds (Ryan, M. C., Tizard, R., VanDevanter, D. R. & Carter, W. G. (1994) J. Biol. Chem. 269: 22779–22787; Larjava, H., Salo, T., Haapasalmi, K., Kramer, R. H. & Heino J. (1993) Clin. Invest. 92: 1425–1435; Pyke, C., Romer, J., Kallunki, P., Lund, L. R., Ralfkiaer, E., Dano, K. & Tryggvason, K (1994) Am. J. Pathol. 145: 782–791), and also in tumor cells of invasive carcinomas (Pyke, C., Romer, J., Kallunki, P., Lund, L. R., Ralfkiaer, E., Dano, K. & Tryggvason, K (1994) Am. J. Pathol. 145: 782–791; Pyke, C., Salo, S., Ralfkiaer, E., Romer, J., Dano, K. & Tryggvason, K. (1995) Cancer Res. 55: 4132–4139; Tani, T., Karttunen, T., Kiviluoto, T., Kivilaakso, E., Burgeson, R. E., Sipponen, P. & Virtanen, I. (1996) Am. J. Pathol. 149: 781–793). Thus, this laminin isoform could not only be surmised to be crucial for anchoring epithelial cells to the underlying basement membrane but, additionally, a protein of importance for anchoring epithelial cells or epithelium-derived cancer cells to the extracellular environment during cell migration. According to the results of Example 4 of the present invention, antibodies against the short arm of the laminin γ2 chain inhibited the migration of KLN-205 squamous carcinoma cells by about 55–65% as determined in the Boyden chamber migration assay. Interestingly, the antibodies used here were directed against 177 amino acid residues of domain III that when deleted by mutation cause lethal junctional epidermolysis bullosa. Accordingly, the short arm of the laminin γ2 chain is important for the interaction of this laminin isoform to other extracellular matrix proteins, and this interaction is also crucial for the migration process. Importantly, polyclonal antibodies raised against the long arm of the γ2 chain did not inhibit migration of KLN-205 cells. Consequently, the results of the present study demonstrate that the short arm of the γ2 chain is important for the adhesive function of laminin-5 similarly the short arm of the laminin γ1 chain that contains the only known binding site of laminins for nidogen. This nidogen binding site is essential for the formation of a bridge between the laminin network on the one hand and the type IV collagen network and perlecan on the other and, thus, it is necessary for the integrity of the entire basement membrane matrix. The present and previous data discussed above indicate that similarly to the γ1 chain, the laminin γ2 chain possesses an important binding site that anchors laminin-5 to some components of the extracellular matrix. However, the laminin γ2 chain does not bind to nidogen.

The results of the experiments shown in Example 4 above with the LAMC2 promoter-reporter gene constructs further emphasized the involvement of the γ2 chain and laminin-5 in cell migration, as the reporter gene was strongly expressed in migratory cells of healing wounds. The actual cis-acting element required for this migration-related expression were not identified but it must be located in the 613 base pair upstream region flanking the gene. This region contains several motifs known to be important for gene expression such as a GATAA box, AP-1 and Sp1 binding sites and a CTF motif. However, none of those have been shown to be associated with cell migration. The results of the transgenic mouse experiments carried out in this study further demonstrated that all the enhancer elements necessary for driving normal expression in epithelial cells are not present in a sequence reaching as far as 5,900 bp upstream of the transcription initiation site. Thus far, no other tissue-specific enhancer elements have been reported for any laminin gene.

Those skilled in the art will know, or be able to ascertain, using no more than routine experimentation, many equivalents to the specific embodiments of the invention described herein. These and all other equivalents are intended to be encompassed by the following claims.

We claim:

1. A method for decreasing cell migration, comprising contacting epithelial-derived cells with antibodies against γ2 chain domain III of laminin 5, wherein the contacting results in decreased migration of the epithelial-derived cells.

2. The method of claim 1 wherein the epithelial-derived cells comprise tumor cells.

3. The method of claim 1 wherein the contacting occurs in vitro.

4. The method of claim 1 wherein the contacting occurs in vivo.

5. The method of claim 1 wherein the antibodies comprise monoclonal antibodies.

6. The method of claim 1 wherein the antibodies comprise polyclonal antibodies.

* * * * *

SEQUENCE LISTING

```
(1) GENERAL INFORMATION:

(iii) NUMBER OF SEQUENCES: 20

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligomer primers"

(xi) SEQUENCE DESCRIPTION: SEQ ID NO: 1:

GGCTCACCAA GACTTACACA                                               20

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 2:

GAATCACTGA GCAGCTGAAC                                               20

(2) INFORMATION FOR SEQ ID NO: 3:

(i) SEQUENCE CHARACTERISTICS:
        (A) LENGTH: 20 base pairs
        (B) TYPE: nucleic acid
```

```
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 3:

CAGTACCAGA ACCGAGTTCG                                               20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 4:

CTGGTTACCA GGCTTGAGAG                                               20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 5:

TTACTGCGGA ATCTCACAGC                                               20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 6:

TACACTGTTC AACCCAGGGT                                               20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 7:

AAACAAGCCC TCTCACTGGT                                               20

(2) INFORMATION FOR SEQ ID NO: 8:

(i) SEQUENCE CHARACTERISTICS:
        (A) LENGTH: 20 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 8:

GCGGAGACTG TGCTGATAAG                                           20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 9:

CATACCTCTC TACATGGCAT                                           20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 10:

AGTCTCGCTG AATCTCTCTT                                           20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGOMER PRIMER"

(xi) SEQUENCE DESCRIPTION: SEQ ID NO: 11:

TTACAACTAG CATGGTGCCC                                           20

(2) INFORMATION FOR SEQ ID NO: 12:

(i) SEQUENCE CHARACTERISTICS:
        (A) LENGTH: 5200 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: sig_peptide
        (B) LOCATION: 118..183

(ix) FEATURE:
        (A) NAME/KEY: CDS
        (B) LOCATION: 118..3699

(ix) FEATURE:
        (A) NAME/KEY: polyA_site (B) LOCATION: 4433

(ix) FEATURE:
        (A) NAME/KEY: polyA_site
        (B) LOCATION: 5195

(xi) SEQUENCE DESCRIPTION: SEQ ID NO: 12:

```
GACCACCTGA TCGAAGGAAA AGGAAGGCAC AGCGGAGCGC AGAGTGAGAA CCACCAACCG          60

AGGCGCCGGG CAGCGACCCC TGCAGCGGAG ACAGAGACTG AGCGGCCCGG CACCGCC            117

ATG CCT GCG CTC TGG CTG GGC TGC TGC CTC TGC TTC TCG CTC CTC CTG           165
Met Pro Ala Leu Trp Leu Gly Cys Cys Leu Cys Phe Ser Leu Leu Leu
 1               5                  10                  15

CCC GCA GCC CGG GCC ACC TCC AGG AGG GAA GTC TGT GAT TGC AAT GGG           213
Pro Ala Ala Arg Ala Thr Ser Arg Arg Glu Val Cys Asp Cys Asn Gly
                20                  25                  30

AAG TCC AGG CAG TGT ATC TTT GAT CGG GAA CTT CAC AGA CAA ACT GGT           261
Lys Ser Arg Gln Cys Ile Phe Asp Arg Glu Leu His Arg Gln Thr Gly
            35                  40                  45

AAT GGA TTC CGC TGC CTC AAC TGC AAT GAC AAC ACT GAT GGC ATT CAC           309
Asn Gly Phe Arg Cys Leu Asn Cys Asn Asp Asn Thr Asp Gly Ile His
        50                  55                  60

TGC GAG AAG TGC AAG AAT GGC TTT TAC CGG CAC AGA GAA AGG GAC CGC           357
Cys Glu Lys Cys Lys Asn Gly Phe Tyr Arg His Arg Glu Arg Asp Arg
 65                  70                  75                  80

TGT TTG CCC TGC AAT TGT AAC TCC AAA GGT TCT CTT AGT GCT CGA TGT           405
Cys Leu Pro Cys Asn Cys Asn Ser Lys Gly Ser Leu Ser Ala Arg Cys
                85                  90                  95

GAC AAC TCT GGA CGG TGC AGC TGT AAA CCA GGT GTG ACA GGA GCC AGA           453
Asp Asn Ser Gly Arg Cys Ser Cys Lys Pro Gly Val Thr Gly Ala Arg
                100                 105                 110

TGC GAC CGA TGT CTG CCA GGC TTC CAC ATG CTC ACG GAT GCG GGG TGC           501
Cys Asp Arg Cys Leu Pro Gly Phe His Met Leu Thr Asp Ala Gly Cys
            115                 120                 125

ACC CAA GAC CAG AGA CTG CTA GAC TCC AAG TGT GAC TGT GAC CCA GCT           549
Thr Gln Asp Gln Arg Leu Leu Asp Ser Lys Cys Asp Cys Asp Pro Ala
        130                 135                 140

GGC ATC GCA GGG CCC TGT GAC GCG GGC CGC TGT GTC TGC AAG CCA GCT           597
Gly Ile Ala Gly Pro Cys Asp Ala Gly Arg Cys Val Cys Lys Pro Ala
145                 150                 155                 160

GTT ACT GGA GAA CGC TGT GAT AGG TGT CGA TCA GGT TAC TAT AAT CTG           645
Val Thr Gly Glu Arg Cys Asp Arg Cys Arg Ser Gly Tyr Tyr Asn Leu
                165                 170                 175

GAT GGG GGG AAC CCT GAG GGC TGT ACC CAG TGT TTC TGC TAT GGG CAT           693
Asp Gly Gly Asn Pro Glu Gly Cys Thr Gln Cys Phe Cys Tyr Gly His
                180                 185                 190

TCA GCC AGC TGC CGC AGC TCT GCA GAA TAC AGT GTC CAT AAG ATC ACC           741
Ser Ala Ser Cys Arg Ser Ser Ala Glu Tyr Ser Val His Lys Ile Thr
            195                 200                 205

TCT ACC TTT CAT CAA GAT GTT GAT GGC TGG AAG GCT GTC CAA CGA AAT           789
Ser Thr Phe His Gln Asp Val Asp Gly Trp Lys Ala Val Gln Arg Asn
210                 215                 220

GGG TCT CCT GCA AAG CTC CAA TGG TCA CAG CGC CAT CAA GAT GTG TTT           837
Gly Ser Pro Ala Lys Leu Gln Trp Ser Gln Arg His Gln Asp Val Phe
225                 230                 235                 240

AGC TCA GCC CAA CGA CTA GAT CCT GTC TAT TTT GTG GCT CCT GCC AAA           885
Ser Ser Ala Gln Arg Leu Asp Pro Val Tyr Phe Val Ala Pro Ala Lys
                245                 250                 255

TTT CTT GGG AAT CAA CAG GTG AGC TAT GGG CAA AGC CTG TCC TTT GAC           933
Phe Leu Gly Asn Gln Gln Val Ser Tyr Gly Gln Ser Leu Ser Phe Asp
                260                 265                 270
```

-continued

| | |
|---|---|
| TAC CGT GTG GAC AGA GGA GGC AGA CAC CCA TCT GCC CAT GAT GTG ATC<br>Tyr Arg Val Asp Arg Gly Gly Arg His Pro Ser Ala His Asp Val Ile<br>        275                     280                  285 | 981 |
| CTG GAA GGT GCT GGT CTA CGG ATC ACA GCT CCC TTG ATG CCA CTT GGC<br>Leu Glu Gly Ala Gly Leu Arg Ile Thr Ala Pro Leu Met Pro Leu Gly<br>    290                        295                     300 | 1029 |
| AAG ACA CTG CCT TGT GGG CTC ACC AAG ACT TAC ACA TTC AGG TTA AAT<br>Lys Thr Leu Pro Cys Gly Leu Thr Lys Thr Tyr Thr Phe Arg Leu Asn<br>305                    310                    315                  320 | 1077 |
| GAG CAT CCA AGC AAT AAT TGG AGC CCC CAG CTG AGT TAC TTT GAG TAT<br>Glu His Pro Ser Asn Asn Trp Ser Pro Gln Leu Ser Tyr Phe Glu Tyr<br>                          325                        330                  335 | 1125 |
| CGA AGG TTA CTG CGG AAT CTC ACA GCC CTC CGC ATC CGA GCT ACA TAT<br>Arg Arg Leu Leu Arg Asn Leu Thr Ala Leu Arg Ile Arg Ala Thr Tyr<br>            340                       345                     350 | 1173 |
| GGA GAA TAC AGT ACT GGG TAC ATT GAC AAT GTG ACC CTG ATT TCA GCC<br>Gly Glu Tyr Ser Thr Gly Tyr Ile Asp Asn Val Thr Leu Ile Ser Ala<br>                355                      360                      365 | 1221 |
| CGC CCT GTC TCT GGA GCC CCA GCA CCC TGG GTT GAA CAG TGT ATA TGT<br>Arg Pro Val Ser Gly Ala Pro Ala Pro Trp Val Glu Gln Cys Ile Cys<br>370                            375                       380 | 1269 |
| CCT GTT GGG TAC AAG GGG CAA TTC TGC CAG GAT TGT GCT TCT GGC TAC<br>Pro Val Gly Tyr Lys Gly Gln Phe Cys Gln Asp Cys Ala Ser Gly Tyr<br>385                    390                    395                  400 | 1317 |
| AAG AGA GAT TCA GCG AGA CTG GGG CCT TTT GGC ACC TGT ATT CCT TGT<br>Lys Arg Asp Ser Ala Arg Leu Gly Pro Phe Gly Thr Cys Ile Pro Cys<br>                      405                      410                  415 | 1365 |
| AAC TGT CAA GGG GGA GGG GCC TGT GAT CCA GAC ACA GGA GAT TGT TAT<br>Asn Cys Gln Gly Gly Gly Ala Cys Asp Pro Asp Thr Gly Asp Cys Tyr<br>                    420                      425                     430 | 1413 |
| TCA GGG GAT GAG AAT CCT GAC ATT GAG TGT GCT GAC TGC CCA ATT GGT<br>Ser Gly Asp Glu Asn Pro Asp Ile Glu Cys Ala Asp Cys Pro Ile Gly<br>                  435                      440                     445 | 1461 |
| TTC TAC AAC GAT CCG CAC GAC CCC CGC AGC TGC AAG CCA TGT CCC TGT<br>Phe Tyr Asn Asp Pro His Asp Pro Arg Ser Cys Lys Pro Cys Pro Cys<br>450                            455                       460 | 1509 |
| CAT AAC GGG TTC AGC TGC TCA GTG ATT CCG GAG ACG GAG GAG GTG GTG<br>His Asn Gly Phe Ser Cys Ser Val Ile Pro Glu Thr Glu Glu Val Val<br>465                    470                    475                  480 | 1557 |
| TGC AAT AAC TGC CCT CCC GGG GTC ACC GGT GCC CGC TGT GAG CTC TGT<br>Cys Asn Asn Cys Pro Pro Gly Val Thr Gly Ala Arg Cys Glu Leu Cys<br>                      485                      490                  495 | 1605 |
| GCT GAT GGC TAC TTT GGG GAC CCC TTT GGT GAA CAT GGC CCA GTG AGG<br>Ala Asp Gly Tyr Phe Gly Asp Pro Phe Gly Glu His Gly Pro Val Arg<br>                  500                      505                     510 | 1653 |
| CCT TGT CAG CCC TGT CAA TGC AAC AGC AAT GTG GAC CCC AGT GCC TCT<br>Pro Cys Gln Pro Cys Gln Cys Asn Ser Asn Val Asp Pro Ser Ala Ser<br>            515                      520                    525 | 1701 |
| GGG AAT TGT GAC CGG CTG ACA GGC AGG TGT TTG AAG TGT ATC CAC AAC<br>Gly Asn Cys Asp Arg Leu Thr Gly Arg Cys Leu Lys Cys Ile His Asn<br>530                    535                    540 | 1749 |
| ACA GCC GGC ATC TAC TGC GAC CAG TGC AAA GCA GGC TAC TTC GGG GAC<br>Thr Ala Gly Ile Tyr Cys Asp Gln Cys Lys Ala Gly Tyr Phe Gly Asp<br>545                    550                    555                  560 | 1797 |
| CCA TTG GCT CCC AAC CCA GCA GAC AAG TGT CGA GCT TGC AAC TGT AAC<br>Pro Leu Ala Pro Asn Pro Ala Asp Lys Cys Arg Ala Cys Asn Cys Asn<br>                    565                      570                    575 | 1845 |
| CCC ATG GGC TCA GAG CCT GTA GGA TGT CGA AGT GAT GGC ACC TGT GTT<br>Pro Met Gly Ser Glu Pro Val Gly Cys Arg Ser Asp Gly Thr Cys Val | 1893 |

```
                  580                585                590
TGC AAG CCA GGA TTT GGT GGC CCC AAC TGT GAG CAT GGA GCA TTC AGC    1941
Cys Lys Pro Gly Phe Gly Gly Pro Asn Cys Glu His Gly Ala Phe Ser
        595                600                605

TGT CCA GCT TGC TAT AAT CAA GTG AAG ATT CAG ATG GAT CAG TTT ATG    1989
Cys Pro Ala Cys Tyr Asn Gln Val Lys Ile Gln Met Asp Gln Phe Met
610                615                620

CAG CAG CTT CAG AGA ATG GAG GCC CTG ATT TCA AAG GCT CAG GGT GGT    2037
Gln Gln Leu Gln Arg Met Glu Ala Leu Ile Ser Lys Ala Gln Gly Gly
625                630                635                640

GAT GGA GTA GTA CCT GAT ACA GAG CTG GAA GGC AGG ATG CAG CAG GCT    2085
Asp Gly Val Val Pro Asp Thr Glu Leu Glu Gly Arg Met Gln Gln Ala
                645                650                655

GAG CAG GCC CTT CAG GAC ATT CTG AGA GAT GCC CAG ATT TCA GAA GGT    2133
Glu Gln Ala Leu Gln Asp Ile Leu Arg Asp Ala Gln Ile Ser Glu Gly
                660                665                670

GCT AGC AGA TCC CTT GGT CTC CAG TTG GCC AAG GTG AGG AGC CAA GAG    2181
Ala Ser Arg Ser Leu Gly Leu Gln Leu Ala Lys Val Arg Ser Gln Glu
                675                680                685

AAC AGC TAC CAG AGC CGC CTG GAT GAC CTC AAG ATG ACT GTG AAA AGA    2229
Asn Ser Tyr Gln Ser Arg Leu Asp Asp Leu Lys Met Thr Val Glu Arg
690                695                700

GTT CGG GCT CTG GGA AGT CAG TAC CAG AAC CGA GTT CGG GAT ACT CAC    2277
Val Arg Ala Leu Gly Ser Gln Tyr Gln Asn Arg Val Arg Asp Thr His
705                710                715                720

AGG CTC ATC ACT CAG ATG CAG CTG AGC CTG GCA GAA AGT GAA GCT TCC    2325
Arg Leu Ile Thr Gln Met Gln Leu Ser Leu Ala Glu Ser Glu Ala Ser
                725                730                735

TTG GGA AAC ACT AAC ATT CCT GCC TCA GAC CAC TAC GTG GGG CCA AAT    2373
Leu Gly Asn Thr Asn Ile Pro Ala Ser Asp His Tyr Val Gly Pro Asn
                740                745                750

GGC TTT AAA AGT CTG GCT CAG GAG GCC ACA AGA TTA GCA GAA AGC CAC    2421
Gly Phe Lys Ser Leu Ala Gln Glu Ala Thr Arg Leu Ala Glu Ser His
                755                760                765

GTT GAG TCA GCC AGT AAC ATG GAG CAA CTG ACA AGG GAA ACT GAG GAC    2469
Val Glu Ser Ala Ser Asn Met Glu Gln Leu Thr Arg Glu Thr Glu Asp
770                775                780

TAT TCC AAA CAA GCC CTC TCA CTG GTG CGC AAG GCC CTG CAT GAA GGA    2517
Tyr Ser Lys Gln Ala Leu Ser Leu Val Arg Lys Ala Leu His Glu Gly
785                790                795                800

GTC GGA AGC GGA AGC GGT AGC CCG GAC GGT GCT GTG GTG CAA GGG CTT    2565
Val Gly Ser Gly Ser Gly Ser Pro Asp Gly Ala Val Val Gln Gly Leu
                805                810                815

GTG GAA AAA TTG GAG AAA ACC AAG TCC CTG GCC CAG CAG TTG ACA AGG    2613
Val Glu Lys Leu Glu Lys Thr Lys Ser Leu Ala Gln Gln Leu Thr Arg
                820                825                830

GAG GCC ACT CAA GCG GAA ATT GAA GCA GAT AGG TCT TAT CAG CAC AGT    2661
Glu Ala Thr Gln Ala Glu Ile Glu Ala Asp Arg Ser Tyr Gln His Ser
                835                840                845

CTC CGC CTC CTG GAT TCA GTG TCT CCG CTT CAG GGA GTC AGT GAT CAG    2709
Leu Arg Leu Leu Asp Ser Val Ser Pro Leu Gln Gly Val Ser Asp Gln
850                855                860

TCC TTT CAG GTG GAA GAA GCA AAG AGG ATC AAA CAA AAA GCG GAT TCA    2757
Ser Phe Gln Val Glu Glu Ala Lys Arg Ile Lys Gln Lys Ala Asp Ser
865                870                875                880

CTC TCA AGC CTG GTA ACC AGG CAT ATG GAT GAG TTC AAG CGT ACA CAA    2805
Leu Ser Ser Leu Val Thr Arg His Met Asp Glu Phe Lys Arg Thr Gln
                885                890                895

AAG AAT CTG GGA AAC TGG AAA GAA GAA GCA CAG CAG CTC TTA CAG AAT    2853
```

```
                                                        -continued

Lys Asn Leu Gly Asn Trp Lys Glu Glu Ala Gln Gln Leu Leu Gln Asn
                900             905                 910

GGA AAA AGT GGG AGA GAG AAA TCA GAT CAG CTG CTT TCC CGT GCC AAT    2901
Gly Lys Ser Gly Arg Glu Lys Ser Asp Gln Leu Leu Ser Arg Ala Asn
            915                 920                 925

CTT GCT AAA AGC AGA GCA CAA GAA GCA CTG AGT ATG GGC AAT GCC ACT    2949
Leu Ala Lys Ser Arg Ala Gln Glu Ala Leu Ser Met Gly Asn Ala Thr
        930                 935                 940

TTT TAT GAA GTT GAG AGC ATC CTT AAA AAC CTC AGA GAG TTT GAC CTG    2997
Phe Tyr Glu Val Glu Ser Ile Leu Lys Asn Leu Arg Glu Phe Asp Leu
945                 950                 955                 960

CAG GTG GAC AAC AGA AAA GCA GAA GCT GAA GAA GCC ATG AAG AGA CTC    3045
Gln Val Asp Asn Arg Lys Ala Glu Ala Glu Glu Ala Met Lys Arg Leu
                965                 970                 975

TCC TAC ATC AGC CAG AAG GTT TCA GAT GCC AGT GAC AAG ACC CAG CAA    3093
Ser Tyr Ile Ser Gln Lys Val Ser Asp Ala Ser Asp Lys Thr Gln Gln
            980                 985                 990

GCA GAA AGA GCC CTG GGG AGC GCT GCT GCT GAT GCA CAG AGG GCA AAG    3141
Ala Glu Arg Ala Leu Gly Ser Ala Ala Ala Asp Ala Gln Arg Ala Lys
        995                 1000                1005

AAT GGG GCC GGG GAG GCC CTG GAA ATC TCC AGT GAG ATT GAA CAG GAG    3189
Asn Gly Ala Gly Glu Ala Leu Glu Ile Ser Ser Glu Ile Glu Gln Glu
    1010                1015                1020

ATT GGG AGT CTG AAC TTG GAA GCC AAT GTG ACA GCA GAT GGA GCC TTG    3237
Ile Gly Ser Leu Asn Leu Glu Ala Asn Val Thr Ala Asp Gly Ala Leu
1025                1030                1035                1040

GCC ATG GAA AAG GGA CTG GCC TCT CTG AAG AGT GAG ATG AGG GAA GTG    3285
Ala Met Glu Lys Gly Leu Ala Ser Leu Lys Ser Glu Met Arg Glu Val
                1045                1050                1055

GAA GGA GAG CTG GAA AGG AAG GAG CTG GAG TTT GAC ACG AAT ATG GAT    3333
Glu Gly Glu Leu Glu Arg Lys Glu Leu Glu Phe Asp Thr Asn Met Asp
            1060                1065                1070

GCA GTA CAG ATG GTG ATT ACA GAA GCC CAG AAG GTT GAT ACC AGA GCC    3381
Ala Val Gln Met Val Ile Thr Glu Ala Gln Lys Val Asp Thr Arg Ala
        1075                1080                1085

AAG AAC GCT GGG GTT ACA ATC CAA GAC ACA CTC AAC ACA TTA GAC GGC    3429
Lys Asn Ala Gly Val Thr Ile Gln Asp Thr Leu Asn Thr Leu Asp Gly
    1090                1095                1100

CTC CTG CAT CTG ATG GAC CAG CCT CTC AGT GTA GAT GAA GAG GGG CTG    3477
Leu Leu His Leu Met Asp Gln Pro Leu Ser Val Asp Glu Glu Gly Leu
1105                1110                1115                1120

GTC TTA CTG GAG CAG AAG CTT TCC CGA GCC AAG ACC CAG ATC AAC AGC    3525
Val Leu Leu Glu Gln Lys Leu Ser Arg Ala Lys Thr Gln Ile Asn Ser
                1125                1130                1135

CAA CTG CGG CCC ATG ATG TCA GAG CTG GAA GAG AGG GCA CGT CAG CAG    3573
Gln Leu Arg Pro Met Met Ser Glu Leu Glu Glu Arg Ala Arg Gln Gln
            1140                1145                1150

AGG GGC CAC CTC CAT TTG CTG GAG ACA AGC ATA GAT GGG ATT CTG GCT    3621
Arg Gly His Leu His Leu Leu Glu Thr Ser Ile Asp Gly Ile Leu Ala
        1155                1160                1165

GAT GTG AAG AAC TTG GAG AAC ATT AGG GAC AAC CTG CCC CCA GGC TGC    3669
Asp Val Lys Asn Leu Glu Asn Ile Arg Asp Asn Leu Pro Pro Gly Cys
    1170                1175                1180

TAC AAT ACC CAG GCT CTT GAG CAA CAG TGA AGCTGCCATA AATATTTCTC      3719
Tyr Asn Thr Gln Ala Leu Glu Gln Gln  *
1185                1190

AACTGAGGTT CTTGGGATAC AGATCTCAGG GCTCGGAGC CATGTCATGT GAGTGGGT     3779

GATGGGGACA TTTGAACATG TTTAATGGGT ATGCTCAGGT CAACTGACCT GACCCCAT    3839
```

-continued

```
CTGATCCCAT GGCCAGGTGG TTGTCTTATT GCACCATACT CCTTGCTTCC TGATGCTG      3899
CATGAGGCAG ATAGGCACTG GTGTGAGAAT GATCAAGGAT CTGGACCCCA AAGATAGA      3959
GGATGGAAAG ACAAACTGCA CAGGCAGATG TTTGCCTCAT AATAGTCGTA AGTGGAGT      4019
TGGAATTTGG ACAAGTGCTG TTGGGATATA GTCAACTTAT TCTTTGAGTA ATGTGACT      4079
AGGAAAAAAC TTTGACTTTG CCCAGGCATG AAATTCTTCC TAATGTCAGA ACAGAGTG      4139
ACCCAGTCAC ACTGTGGCCA GTAAAATACT ATTGCCTCAT ATTGTCCTCT GCAAGCTT      4199
TGCTGATCAG AGTTCCTCCT ACTTACAACC CAGGGTGTGA ACATGTTCTC CATTTTCA      4259
CTGGAAGAAG TGAGCAGTGT TGGAGTGAGG ACCTGTAAGG CAGGCCCATT CAGAGCTA      4319
GTGCTTGCTG GTGCCTGCCA CCTTCAAGTT CTGGACCTGG GCATGACATC CTTTCTTT      4379
ATGATGCCAT GGCAACTTAG AGATTGCATT TTTATTAAAG CATTTCCTAC CAGCAAAG      4439
AATGTTGGGA AAGTATTTAC TTTTTCGGTT TCAAAGTGAT AGAAAGTGT GGCTTGGG       4499
TTGAAAGAGG TAAAATTCTC TAGATTTATT AGTCCTAATT CAATCCTACT TTTCGAAC      4559
CAAAAATGAT GCGCATCAAT GTATTTTATC TTATTTTCTC AATCTCCTCT CTCTTTCC      4619
CACCCATAAT AAGAGAATGT TCCTACTCAC ACTTCAGCTG GGTCACATCC ATCCCTCC      4679
TCATCCTTCC ATCCATCTTT CCATCCATTA CCTCCATCCA TCCTTCCAAC ATATATTT      4739
TGAGTACCTA CTGTGTGCCA GGGGCTGGTG GGACAGTGGT GACATAGTCT CTGCCCTC      4799
AGAGTTGATT GTCTAGTGAG GAAGACAAGC ATTTTTAAAA AATAAATTTA AACTTACA      4859
CTTTGTTTGT CACAAGTGGT GTTTATTGCA ATAACCGCTT GGTTTGCAAC CTCTTTGC      4919
AACAGAACAT ATGTTGCAAG ACCCTCCCAT GGGCACTGAG TTTGGCAAGG ATGACAGA      4979
TCTGGGTTGT GCACATTTCT TTGCATTCCA GCGTCACTCT GTGCCTTCTA CAACTGAT      5039
CAACAGACTG TTGAGTTATG ATAACACCAG TGGGAATTGC TGGAGGAACC AGAGGCAC      5099
CCACCTTGGC TGGAAGACT ATGGTGCTGC CTTGCTTCTG TATTTCCTTG GATTTTCC       5159
AAAGTGTTTT TAAATAAAGA ACAATTGTTA GATGCCAAAA A                        5200
```

(2) INFORMATION FOR SEQ ID NO: 13:

(i) SEQUENCE CHARACTERISTICS:
        (A) LENGTH: 1193 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Pro Ala Leu Trp Leu Gly Cys Cys Leu Cys Phe Ser Leu Leu Leu
 1               5                  10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110
```

-continued

```
Cys Asp Arg Cys Leu Pro Gly Phe His Met Leu Thr Asp Ala Gly Cys
            115                 120                 125
Thr Gln Asp Gln Arg Leu Leu Asp Ser Lys Cys Asp Cys Asp Pro Ala
        130                 135                 140
Gly Ile Ala Gly Pro Cys Asp Ala Gly Arg Cys Val Cys Lys Pro Ala
145                 150                 155                 160
Val Thr Gly Glu Arg Cys Asp Arg Cys Arg Ser Gly Tyr Tyr Asn Leu
                165                 170                 175
Asp Gly Gly Asn Pro Glu Gly Cys Thr Gln Cys Phe Cys Tyr Gly His
            180                 185                 190
Ser Ala Ser Cys Arg Ser Ser Ala Glu Tyr Ser Val His Lys Ile Thr
        195                 200                 205
Ser Thr Phe His Gln Asp Val Asp Gly Trp Lys Ala Val Gln Arg Asn
    210                 215                 220
Gly Ser Pro Ala Lys Leu Gln Trp Ser Gln Arg His Gln Asp Val Phe
225                 230                 235                 240
Ser Ser Ala Gln Arg Leu Asp Pro Val Tyr Phe Val Ala Pro Ala Lys
                245                 250                 255
Phe Leu Gly Asn Gln Gln Val Ser Tyr Gly Gln Ser Leu Ser Phe Asp
            260                 265                 270
Tyr Arg Val Asp Arg Gly Gly Arg His Pro Ser Ala His Asp Val Ile
        275                 280                 285
Leu Glu Gly Ala Gly Leu Arg Ile Thr Ala Pro Leu Met Pro Leu Gly
    290                 295                 300
Lys Thr Leu Pro Cys Gly Leu Thr Lys Thr Tyr Thr Phe Arg Leu Asn
305                 310                 315                 320
Glu His Pro Ser Asn Asn Trp Ser Pro Gln Leu Ser Tyr Phe Glu Tyr
                325                 330                 335
Arg Arg Leu Leu Arg Asn Leu Thr Ala Leu Arg Ile Arg Ala Thr Tyr
            340                 345                 350
Gly Glu Tyr Ser Thr Gly Tyr Ile Asp Asn Val Thr Leu Ile Ser Ala
        355                 360                 365
Arg Pro Val Ser Gly Ala Pro Ala Pro Trp Val Glu Gln Cys Ile Cys
    370                 375                 380
Pro Val Gly Tyr Lys Gly Gln Phe Cys Gln Asp Cys Ala Ser Gly Tyr
385                 390                 395                 400
Lys Arg Asp Ser Ala Arg Leu Gly Pro Phe Gly Thr Cys Ile Pro Cys
                405                 410                 415
Asn Cys Gln Gly Gly Ala Cys Asp Pro Asp Thr Gly Asp Cys Tyr
            420                 425                 430
Ser Gly Asp Glu Asn Pro Asp Ile Glu Cys Ala Asp Cys Pro Ile Gly
        435                 440                 445
Phe Tyr Asn Asp Pro His Asp Pro Arg Ser Cys Lys Pro Cys Pro Cys
    450                 455                 460
His Asn Gly Phe Ser Cys Ser Val Ile Pro Glu Thr Glu Glu Val Val
465                 470                 475                 480
Cys Asn Asn Cys Pro Pro Gly Val Thr Gly Ala Arg Cys Glu Leu Cys
                485                 490                 495
Ala Asp Gly Tyr Phe Gly Asp Pro Phe Gly Glu His Gly Pro Val Arg
            500                 505                 510
Pro Cys Gln Pro Cys Gln Cys Asn Ser Asn Val Asp Pro Ser Ala Ser
        515                 520                 525
Gly Asn Cys Asp Arg Leu Thr Gly Arg Cys Leu Lys Cys Ile His Asn
```

-continued

```
            530                 535                 540
Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
            580                 585                 590

Cys Lys Pro Gly Phe Gly Pro Asn Cys Glu His Gly Ala Phe Ser
        595                 600                 605

Cys Pro Ala Cys Tyr Asn Gln Val Lys Ile Gln Met Asp Gln Phe Met
610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
            660                 665                 670

Ala Ser Arg Ser Leu Gly Leu Gln Leu Ala Lys Val Arg Ser Gln Glu
        675                 680                 685

Asn Ser Tyr Gln Ser Arg Leu Asp Asp Leu Lys Met Thr Val Glu Arg
690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
            740                 745                 750

Gly Phe Lys Ser Leu Ala Gln Glu Ala Thr Arg Leu Ala Glu Ser His
        755                 760                 765

Val Glu Ser Ala Ser Asn Met Glu Gln Leu Thr Arg Glu Thr Glu Asp
        770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
        835                 840                 845

Leu Arg Leu Leu Asp Ser Val Ser Pro Leu Gln Gly Val Ser Asp Gln
850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
        915                 920                 925

Leu Ala Lys Ser Arg Ala Gln Glu Ala Leu Ser Met Gly Asn Ala Thr
930                 935                 940

Phe Tyr Glu Val Glu Ser Ile Leu Lys Asn Leu Arg Glu Phe Asp Leu
945                 950                 955                 960
```

```
Gln Val Asp Asn Arg Lys Ala Glu Ala Glu Ala Met Lys Arg Leu
            965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Asp Ala Gln Arg Ala Lys
            995                 1000                1005

Asn Gly Ala Gly Glu Ala Leu Glu Ile Ser Ser Glu Ile Glu Gln Glu
            1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
            1045                1050                1055

Glu Gly Glu Leu Glu Arg Lys Glu Leu Glu Phe Asp Thr Asn Met Asp
            1060                1065                1070

Ala Val Gln Met Val Ile Thr Glu Ala Gln Lys Val Asp Thr Arg Ala
            1075                1080                1085

Lys Asn Ala Gly Val Thr Ile Gln Asp Thr Leu Asn Thr Leu Asp Gly
1090                1095                1100

Leu Leu His Leu Met Asp Gln Pro Leu Ser Val Asp Glu Glu Gly Leu
1105                1110                1115                1120

Val Leu Leu Glu Gln Lys Leu Ser Arg Ala Lys Thr Gln Ile Asn Ser
            1125                1130                1135

Gln Leu Arg Pro Met Met Ser Glu Leu Glu Glu Arg Ala Arg Gln Gln
            1140                1145                1150

Arg Gly His Leu His Leu Leu Glu Thr Ser Ile Asp Gly Ile Leu Ala
            1155                1160                1165

Asp Val Lys Asn Leu Glu Asn Ile Arg Asp Asn Leu Pro Pro Gly Cys
            1170                1175                1180

Tyr Asn Thr Gln Ala Leu Glu Gln Gln
1185                1190

(2) INFORMATION FOR SEQ ID NO: 14:

(i) SEQUENCE CHARACTERISTICS:
        (A) LENGTH: 4316 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: sig_peptide
        (B) LOCATION: 118..183

(ix) FEATURE:
        (A) NAME/KEY: CDS
        (B) LOCATION: 118..3453

(ix) FEATURE:
        (A) NAME/KEY: repeat_unit
        (B) LOCATION: 4021..4316
        (D) OTHER INFORMATION: /rpt_type= "other"
            /rpt_family= "HUMAN ALU"

(ix) FEATURE:
        (A) NAME/KEY: polyA_site
        (B) LOCATION: 4296

(xi) SEQUENCE DESCRIPTION: SEQ ID NO: 14:

GACCACCTGA TCGAAGGAAA AGGAAGGCAC AGCGGAGCGC AGAGTGAGAA CCACCAACCG    60
```

-continued

```
AGGCGCCGGG CAGCGACCCC TGCAGCGGAG ACAGAGACTG AGCGGCCCGG CACCGCC         117

ATG CCT GCG CTC TGG CTG GGC TGC TGC CTC TGC TTC TCG CTC CTC CTG         165
Met Pro Ala Leu Trp Leu Gly Cys Cys Leu Cys Phe Ser Leu Leu Leu
1195                1200                1205                1210

CCC GCA GCC CGG GCC ACC TCC AGG AGG GAA GTC TGT GAT TGC AAT GGG         213
Pro Ala Ala Arg Ala Thr Ser Arg Arg Glu Val Cys Asp Cys Asn Gly
                1215                1220                1225

AAG TCC AGG CAG TGT ATC TTT GAT CGG GAA CTT CAC AGA CAA ACT GGT         261
Lys Ser Arg Gln Cys Ile Phe Asp Arg Glu Leu His Arg Gln Thr Gly
                1230                1235                1240

AAT GGA TTC CGC TGC CTC AAC TGC AAT GAC AAC ACT GAT GGC ATT CAC         309
Asn Gly Phe Arg Cys Leu Asn Cys Asn Asp Asn Thr Asp Gly Ile His
                1245                1250                1255

TGC GAG AAG TGC AAG AAT GGC TTT TAC CGG CAC AGA GAA AGG GAC CGC         357
Cys Glu Lys Cys Lys Asn Gly Phe Tyr Arg His Arg Glu Arg Asp Arg
                1260                1265                1270

TGT TTG CCC TGC AAT TGT AAC TCC AAA GGT TCT CTT AGT GCT CGA TGT         405
Cys Leu Pro Cys Asn Cys Asn Ser Lys Gly Ser Leu Ser Ala Arg Cys
1275                1280                1285                1290

GAC AAC TCT GGA CGG TGC AGC TGT AAA CCA GGT GTG ACA GGA GCC AGA         453
Asp Asn Ser Gly Arg Cys Ser Cys Lys Pro Gly Val Thr Gly Ala Arg
                1295                1300                1305

TGC GAC CGA TGT CTG CCA GGC TTC CAC ATG CTC ACG GAT GCG GGG TGC         501
Cys Asp Arg Cys Leu Pro Gly Phe His Met Leu Thr Asp Ala Gly Cys
                1310                1315                1320

ACC CAA GAC CAG AGA CTG CTA GAC TCC AAG TGT GAC TGT GAC CCA GCT         549
Thr Gln Asp Gln Arg Leu Leu Asp Ser Lys Cys Asp Cys Asp Pro Ala
                1325                1330                1335

GGC ATC GCA GGG CCC TGT GAC GCG GGC CGC TGT GTC TGC AAG CCA GCT         597
Gly Ile Ala Gly Pro Cys Asp Ala Gly Arg Cys Val Cys Lys Pro Ala
                1340                1345                1350

GTT ACT GGA GAA CGC TGT GAT AGG TGT CGA TCA GGT TAC TAT AAT CTG         645
Val Thr Gly Glu Arg Cys Asp Arg Cys Arg Ser Gly Tyr Tyr Asn Leu
1355                1360                1365                1370

GAT GGG GGG AAC CCT GAG GGC TGT ACC CAG TGT TTC TGC TAT GGG CAT         693
Asp Gly Gly Asn Pro Glu Gly Cys Thr Gln Cys Phe Cys Tyr Gly His
                1375                1380                1385

TCA GCC AGC TGC CGC AGC TCT GCA GAA TAC AGT GTC CAT AAG ATC ACC         741
Ser Ala Ser Cys Arg Ser Ser Ala Glu Tyr Ser Val His Lys Ile Thr
                1390                1395                1400

TCT ACC TTT CAT CAA GAT GTT GAT GGC TGG AAG GCT GTC CAA CGA AAT         789
Ser Thr Phe His Gln Asp Val Asp Gly Trp Lys Ala Val Gln Arg Asn
                1405                1410                1415

GGG TCT CCT GCA AAG CTC CAA TGG TCA CAG CGC CAT CAA GAT GTG TTT         837
Gly Ser Pro Ala Lys Leu Gln Trp Ser Gln Arg His Gln Asp Val Phe
                1420                1425                1430

AGC TCA GCC CAA CGA CTA GAT CCT GTC TAT TTT GTG GCT CCT GCC AAA         885
Ser Ser Ala Gln Arg Leu Asp Pro Val Tyr Phe Val Ala Pro Ala Lys
1435                1440                1445                1450

TTT CTT GGG AAT CAA CAG GTG AGC TAT GGG CAA AGC CTG TCC TTT GAC         933
Phe Leu Gly Asn Gln Gln Val Ser Tyr Gly Gln Ser Leu Ser Phe Asp
                1455                1460                1465

TAC CGT GTG GAC AGA GGA GGC AGA CAC CCA TCT GCC CAT GAT GTG ATC         981
Tyr Arg Val Asp Arg Gly Gly Arg His Pro Ser Ala His Asp Val Ile
                1470                1475                1480

CTG GAA GGT GCT GGT CTA CGG ATC ACA GCT CCC TTG ATG CCA CTT GGC        1029
Leu Glu Gly Ala Gly Leu Arg Ile Thr Ala Pro Leu Met Pro Leu Gly
                1485                1490                1495

AAG ACA CTG CCT TGT GGG CTC ACC AAG ACT TAC ACA TTC AGG TTA AAT        1077
```

```
                                                                         -continued
Lys Thr Leu Pro Cys Gly Leu Thr Lys Thr Tyr Thr Phe Arg Leu Asn
1500                1505                1510

GAG CAT CCA AGC AAT AAT TGG AGC CCC CAG CTG AGT TAC TTT GAG TAT        1125
Glu His Pro Ser Asn Asn Trp Ser Pro Gln Leu Ser Tyr Phe Glu Tyr
1515                1520                1525                1530

CGA AGG TTA CTG CGG AAT CTC ACA GCC CTC CGC ATC CGA GCT ACA TAT        1173
Arg Arg Leu Leu Arg Asn Leu Thr Ala Leu Arg Ile Arg Ala Thr Tyr
                1535                1540                1545

GGA GAA TAC AGT ACT GGG TAC ATT GAC AAT GTG ACC CTG ATT TCA GCC        1221
Gly Glu Tyr Ser Thr Gly Tyr Ile Asp Asn Val Thr Leu Ile Ser Ala
            1550                1555                1560

CGC CCT GTC TCT GGA GCC CCA GCA CCC TGG GTT GAA CAG TGT ATA TGT        1269
Arg Pro Val Ser Gly Ala Pro Ala Pro Trp Val Glu Gln Cys Ile Cys
        1565                1570                1575

CCT GTT GGG TAC AAG GGG CAA TTC TGC CAG GAT TGT GCT TCT GGC TAC        1317
Pro Val Gly Tyr Lys Gly Gln Phe Cys Gln Asp Cys Ala Ser Gly Tyr
    1580                1585                1590

AAG AGA GAT TCA GCG AGA CTG GGG CCT TTT GGC ACC TGT ATT CCT TGT        1365
Lys Arg Asp Ser Ala Arg Leu Gly Pro Phe Gly Thr Cys Ile Pro Cys
1595                1600                1605                1610

AAC TGT CAA GGG GGA GGG GCC TGT GAT CCA GAC ACA GGA GAT TGT TAT        1413
Asn Cys Gln Gly Gly Gly Ala Cys Asp Pro Asp Thr Gly Asp Cys Tyr
                1615                1620                1625

TCA GGG GAT GAG AAT CCT GAC ATT GAG TGT GCT GAC TGC CCA ATT GGT        1461
Ser Gly Asp Glu Asn Pro Asp Ile Glu Cys Ala Asp Cys Pro Ile Gly
            1630                1635                1640

TTC TAC AAC GAT CCG CAC GAC CCC CGC AGC TGC AAG CCA TGT CCC TGT        1509
Phe Tyr Asn Asp Pro His Asp Pro Arg Ser Cys Lys Pro Cys Pro Cys
        1645                1650                1655

CAT AAC GGG TTC AGC TGC TCA GTG ATT CCG GAG ACG GAG GAG GTG GTG        1557
His Asn Gly Phe Ser Cys Ser Val Ile Pro Glu Thr Glu Glu Val Val
    1660                1665                1670

TGC AAT AAC TGC CCT CCC GGG GTC ACC GGT GCC CGC TGT GAG CTC TGT        1605
Cys Asn Asn Cys Pro Pro Gly Val Thr Gly Ala Arg Cys Glu Leu Cys
1675                1680                1685                1690

GCT GAT GGC TAC TTT GGG GAC CCC TTT GGT GAA CAT GGC CCA GTG AGG        1653
Ala Asp Gly Tyr Phe Gly Asp Pro Phe Gly Glu His Gly Pro Val Arg
                1695                1700                1705

CCT TGT CAG CCC TGT CAA TGC AAC AGC AAT GTG GAC CCC AGT GCC TCT        1701
Pro Cys Gln Pro Cys Gln Cys Asn Ser Asn Val Asp Pro Ser Ala Ser
            1710                1715                1720

GGG AAT TGT GAC CGG CTG ACA GGC AGG TGT TTG AAG TGT ATC CAC AAC        1749
Gly Asn Cys Asp Arg Leu Thr Gly Arg Cys Leu Lys Cys Ile His Asn
        1725                1730                1735

ACA GCC GGC ATC TAC TGC GAC CAG TGC AAA GCA GGC TAC TTC GGG GAC        1797
Thr Ala Gly Ile Tyr Cys Asp Gln Cys Lys Ala Gly Tyr Phe Gly Asp
    1740                1745                1750

CCA TTG GCT CCC AAC CCA GCA GAC AAG TGT CGA GCT GCA ACT GTA AC        1845
Pro Leu Ala Pro Asn Pro Ala Asp Lys Cys Arg Ala Cys Asn Cys Asn
1755                1760                1765                1770

CCC ATG GGC TCA GAG CCT GTA GGA TGT CGA AGT GAT GGC ACC TGT GTT        1893
Pro Met Gly Ser Glu Pro Val Gly Cys Arg Ser Asp Gly Thr Cys Val
                1775                1780                1785

TGC AAG CCA GGA TTT GGT GGC CCC AAC TGT GAG CAT GGA GCA TTC AGC        1941
Cys Lys Pro Gly Phe Gly Gly Pro Asn Cys Glu His Gly Ala Phe Ser
            1790                1795                1800

TGT CCA GCT TGC TAT AAT CAA GTG AAG ATT CAG ATG GAT CAG TTT ATG        1989
Cys Pro Ala Cys Tyr Asn Gln Val Lys Ile Gln Met Asp Gln Phe Met
        1805                1810                1815
```

-continued

| | |
|---|---|
| CAG CAG CTT CAG AGA ATG GAG GCC CTG ATT TCA AAG GCT CAG GGT GGT<br>Gln Gln Leu Gln Arg Met Glu Ala Leu Ile Ser Lys Ala Gln Gly Gly<br>            1820                          1825                      1830 | 2037 |
| GAT GGA GTA GTA CCT GAT ACA GAG CTG GAA GGC AGG ATG CAG CAG GCT<br>Asp Gly Val Val Pro Asp Thr Glu Leu Glu Gly Arg Met Gln Gln Ala<br>1835                      1840                      1845                      1850 | 2085 |
| GAG CAG GCC CTT CAG GAC ATT CTG AGA GAT GCC CAG ATT TCA GAA GGT<br>Glu Gln Ala Leu Gln Asp Ile Leu Arg Asp Ala Gln Ile Ser Glu Gly<br>            1855                          1860                      1865 | 2133 |
| GCT AGC AGA TCC CTT GGT CTC CAG TTG GCC AAG GTG AGG AGC CAA GAG<br>Ala Ser Arg Ser Leu Gly Leu Gln Leu Ala Lys Val Arg Ser Gln Glu<br>            1870                          1875                      1880 | 2181 |
| AAC AGC TAC CAG AGC CGC CTG GAT GAC CTC AAG ATG ACT GTG GAA AGA<br>Asn Ser Tyr Gln Ser Arg Leu Asp Asp Leu Lys Met Thr Val Glu Arg<br>            1885                          1890                      1895 | 2229 |
| GTT CGG GCT CTG GGA AGT CAG TAC CAG AAC CGA GTT CGG GAT ACT CAC<br>Val Arg Ala Leu Gly Ser Gln Tyr Gln Asn Arg Val Arg Asp Thr His<br>1900                      1905                      1910 | 2277 |
| AGG CTC ATC ACT CAG ATG CAG CTG AGC CTG GCA GAA AGT GAA GCT TCC<br>Arg Leu Ile Thr Gln Met Gln Leu Ser Leu Ala Glu Ser Glu Ala Ser<br>1915                      1920                      1925                      1930 | 2325 |
| TTG GGA AAC ACT AAC ATT CCT GCC TCA GAC CAC TAC GTG GGG CCA AAT<br>Leu Gly Asn Thr Asn Ile Pro Ala Ser Asp His Tyr Val Gly Pro Asn<br>            1935                          1940                      1945 | 2373 |
| GGC TTT AAA AGT CTG GCT CAG GAG GCC ACA AGA TTA GCA GAA AGC CAC<br>Gly Phe Lys Ser Leu Ala Gln Glu Ala Thr Arg Leu Ala Glu Ser His<br>            1950                          1955                      1960 | 2421 |
| GTT GAG TCA GCC AGT AAC ATG GAG CAA CTG ACA AGG GAA ACT GAG GAC<br>Val Glu Ser Ala Ser Asn Met Glu Gln Leu Thr Arg Glu Thr Glu Asp<br>            1965                          1970                      1975 | 2469 |
| TAT TCC AAA CAA GCC CTC TCA CTG GTG CGC AAG GCC CTG CAT GAA GGA<br>Tyr Ser Lys Gln Ala Leu Ser Leu Val Arg Lys Ala Leu His Glu Gly<br>1980                      1985                      1990 | 2517 |
| GTC GGA AGC GGA AGC GGT AGC CCG GAC GGT GCT GTG GTG CAA GGG CTT<br>Val Gly Ser Gly Ser Gly Ser Pro Asp Gly Ala Val Val Gln Gly Leu<br>1995                      2000                      2005                      2010 | 2565 |
| GTG GAA AAA TTG GAG AAA ACC AAG TCC CTG GCC CAG CAG TTG ACA AGG<br>Val Glu Lys Leu Glu Lys Thr Lys Ser Leu Ala Gln Gln Leu Thr Arg<br>            2015                          2020                      2025 | 2613 |
| GAG GCC ACT CAA GCG GAA ATT GAA GCA GAT AGG TCT TAT CAG CAC AGT<br>Glu Ala Thr Gln Ala Glu Ile Glu Ala Asp Arg Ser Tyr Gln His Ser<br>            2030                          2035                      2040 | 2661 |
| CTC CGC CTC CTG GAT TCA GTG TCT CCG CTT CAG GGA GTC AGT GAT CAG<br>Leu Arg Leu Leu Asp Ser Val Ser Pro Leu Gln Gly Val Ser Asp Gln<br>            2045                          2050                      2055 | 2709 |
| TCC TTT CAG GTG GAA GAA GCA AAG AGG ATC AAA CAA AAA GCG GAT TCA<br>Ser Phe Gln Val Glu Glu Ala Lys Arg Ile Lys Gln Lys Ala Asp Ser<br>            2060                          2065                      2070 | 2757 |
| CTC TCA AGC CTG GTA ACC AGG CAT ATG GAT GAG TTC AAG CGT ACA CAA<br>Leu Ser Ser Leu Val Thr Arg His Met Asp Glu Phe Lys Arg Thr Gln<br>2075                      2080                      2085                      2090 | 2805 |
| AAG AAT CTG GGA AAC TGG AAA GAA GAA GCA CAG CAG CTC TTA CAG AAT<br>Lys Asn Leu Gly Asn Trp Lys Glu Glu Ala Gln Gln Leu Leu Gln Asn<br>            2095                          2100                      2105 | 2853 |
| GGA AAA AGT GGG AGA GAG AAA TCA GAT CAG CTG CTT TCC CGT GCC AAT<br>Gly Lys Ser Gly Arg Glu Lys Ser Asp Gln Leu Leu Ser Arg Ala Asn<br>            2110                          2115                      2120 | 2901 |
| CTT GCT AAA AGC AGA GCA CAA GAA GCA CTG AGT ATG GGC AAT GCC ACT<br>Leu Ala Lys Ser Arg Ala Gln Glu Ala Leu Ser Met Gly Asn Ala Thr<br>            2125                          2130                      2135 | 2949 |

```
TTT TAT GAA GTT GAG AGC ATC CTT AAA AAC CTC AGA GAG TTT GAC CTG      2997
Phe Tyr Glu Val Glu Ser Ile Leu Lys Asn Leu Arg Glu Phe Asp Leu
    2140                2145                2150

CAG GTG GAC AAC AGA AAA GCA GAA GCT GAA GAA GCC ATG AAG AGA CTC      3045
Gln Val Asp Asn Arg Lys Ala Glu Ala Glu Glu Ala Met Lys Arg Leu
2155                2160                2165                2170

TCC TAC ATC AGC CAG AAG GTT TCA GAT GCC AGT GAC AAG ACC CAG CAA      3093
Ser Tyr Ile Ser Gln Lys Val Ser Asp Ala Ser Asp Lys Thr Gln Gln
                2175                2180                2185

GCA GAA AGA GCC CTG GGG AGC GCT GCT GCT GAT GCA CAG AGG GCA AAG      3141
Ala Glu Arg Ala Leu Gly Ser Ala Ala Ala Asp Ala Gln Arg Ala Lys
            2190                2195                2200

AAT GGG GCC GGG GAG GCC CTG GAA ATC TCC AGT GAG ATT GAA CAG GAG      3189
Asn Gly Ala Gly Glu Ala Leu Glu Ile Ser Ser Glu Ile Glu Gln Glu
        2205                2210                2215

ATT GGG AGT CTG AAC TTG GAA GCC AAT GTG ACA GCA GAT GGA GCC TTG      3237
Ile Gly Ser Leu Asn Leu Glu Ala Asn Val Thr Ala Asp Gly Ala Leu
    2220                2225                2230

GCC ATG GAA AAG GGA CTG GCC TCT CTG AAG AGT GAG ATG AGG GAA GTG      3285
Ala Met Glu Lys Gly Leu Ala Ser Leu Lys Ser Glu Met Arg Glu Val
2235                2240                2245                2250

GAA GGA GAG CTG GAA AGG AAG GAG CTG GAG TTT GAC ACG AAT ATG GAT      3333
Glu Gly Glu Leu Glu Arg Lys Glu Leu Glu Phe Asp Thr Asn Met Asp
                2255                2260                2265

GCA GTA CAG ATG GTG ATT ACA GAA GCC CAG AAG GTT GAT ACC AGA GCC      3381
Ala Val Gln Met Val Ile Thr Glu Ala Gln Lys Val Asp Thr Arg Ala
            2270                2275                2280

AAG AAC GCT GGG GTT ACA ATC CAA GAC ACA CTC AAC ACA TTA GAC GGC      3429
Lys Asn Ala Gly Val Thr Ile Gln Asp Thr Leu Asn Thr Leu Asp Gly
        2285                2290                2295

CTC CTG CAT CTG ATG GGT ATG TGA ACCCACAACC CACAACCTTC CAGCTCCAT      3483
Leu Leu His Leu Met Gly Met  *
    2300                2305

CTCCAGGGCT TGCTCCAGA ACACTCACTA TACCTAGCCC CAGCAAAGGG GAGTCTCA       3543

TTTCCTTAAG GATATCAGTA AATGTGCTTT GTTTCCAGGC CCAGATAACT TTCGGCAG      3603

TCCCTTACAT TTACTGGACC CTGTTTTACC GTTGCTAAGA TGGGTCACTG AACACCTA      3663

GCACTTGGGG GTAAAGGTCT GTGGGCCAAA GAACAGGTGT ATATAAGCAA CTTCACAG      3723

CACGAGACAG CTTGGGAATC CTGCTAAAGA GTCTGGCCTG ACCCTGAGA AGCCAGTG       3783

CAGTTTTAAG CAGAGGAATA ACATCACCAC TGTATATTTC AGAAAGATCA CTAGGGCA      3843

CGAGTGGAGG AAAGCTTGAA GAGGGGGTTA GAGAGAAGGC AGGTTGAGAC TACTTAAG      3903

ATTGTTGAAA TAATTGAAGA GAGAAATGAC AGGAGCCTGC TCTAAGGCAG TAGAATGG      3963

GCTGGGAAGA TGTGAAGGAA GATTTTCCCA GTCTGTGAAG TCAAGAATCA CTTGCCGG      4023

GGGTGTGGTG GCTCACGCCT GTAATTCTAG CACTTTGGGA GACTGAAGCG GTGGATC       4083

CCGAGGTCAG GAGTTGAAGA CCAGCCTGGC CAACATGGTG AAACCCTGTC TCTACTAA      4143

GTACAAAAAT TAGCTGGATG ATGGTGGTGG GCGCCTGTAA TTCCAGCTAC TCAGGAGT      4203

GAGGCAGGAG AATCGCTTGA ACCCAGGAGG CGAGGTTACA GTGAGCCAAG ATTGCACC      4263

TGCTCTTCCA GCCTGGGAAC AGAGAGACTG CCTAAAAAAA AAAAAAAAA AAA           4316

(2) INFORMATION FOR SEQ ID NO: 15:

(i) SEQUENCE CHARACTERISTICS:
        (A) LENGTH: 1111 amino acids
        (B) TYPE: amino acid
```

-continued (D) TOPOLOGY: linear (ii) MOLECULE TYPE: protein (xi) SEQUENCE DESCRIPTION: SEQ ID NO: 15:

```
Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Ile Cys
370                 375                 380

Pro Val Gly Tyr Lys Gly Gln Phe Cys Gln Asp Cys Ala Ser Gly Tyr
```

```
                385                 390                 395                 400

Lys Arg Asp Ser Ala Arg Leu Gly Pro Phe Gly Thr Cys Ile Pro Cys
                405                 410                 415

Asn Cys Gln Gly Gly Gly Ala Cys Asp Pro Asp Thr Gly Asp Cys Tyr
                420                 425                 430

Ser Gly Asp Glu Asn Pro Asp Ile Glu Cys Ala Asp Cys Pro Ile Gly
                435                 440                 445

Phe Tyr Asn Asp Pro His Asp Pro Arg Ser Cys Lys Pro Cys Pro Cys
                450                 455                 460

His Asn Gly Phe Ser Cys Ser Val Ile Pro Glu Thr Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
                500                 505                 510

Pro Cys Gln Pro Cys Gln Cys Asn Ser Asn Val Asp Pro Ser Ala Ser
                515                 520                 525

Gly Asn Cys Asp Arg Leu Thr Gly Arg Cys Leu Lys Cys Ile His Asn
                530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
                580                 585                 590

Cys Lys Pro Gly Phe Gly Gly Pro Asn Cys Glu His Gly Ala Phe Ser
                595                 600                 605

Cys Pro Ala Cys Tyr Asn Gln Val Lys Ile Gln Met Asp Gln Phe Met
                610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
                660                 665                 670

Ala Ser Arg Ser Leu Gly Leu Gln Leu Ala Lys Val Arg Ser Gln Glu
                675                 680                 685

Asn Ser Tyr Gln Ser Arg Leu Asp Asp Leu Lys Met Thr Val Glu Arg
                690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
                740                 745                 750

Gly Phe Lys Ser Leu Ala Gln Glu Ala Thr Arg Leu Ala Glu Ser His
                755                 760                 765

Val Glu Ser Ala Ser Asn Met Glu Gln Leu Thr Arg Glu Thr Glu Asp
                770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815
```

```
Val Glu Lys Leu Glu Lys Thr Lys Ser Leu Ala Gln Gln Leu Thr Arg
        820                 825                 830

Glu Ala Thr Gln Ala Glu Ile Glu Ala Asp Arg Ser Tyr Gln His Ser
        835                 840                 845

Leu Arg Leu Leu Asp Ser Val Ser Pro Leu Gln Gly Val Ser Asp Gln
        850                 855                 860

Ser Phe Gln Val Glu Glu Ala Lys Arg Ile Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
            915                 920                 925

Leu Ala Lys Ser Arg Ala Gln Glu Ala Leu Ser Met Gly Asn Ala Thr
        930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Ala Met Lys Arg Leu
                965                 970                 975

Ser Tyr Ile Ser Gln Lys Val Ser Asp Ala Ser Asp Lys Thr Gln Gln
                980                 985                 990

Ala Glu Arg Ala Leu Gly Ser Ala Ala Asp Ala Gln Arg Ala Lys
            995                 1000                1005

Asn Gly Ala Gly Glu Ala Leu Glu Ile Ser Ser Glu Ile Glu Gln Glu
    1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
                1045                1050                1055

Glu Gly Glu Leu Glu Arg Lys Glu Leu Glu Phe Asp Thr Asn Met Asp
            1060                1065                1070

Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
    1090                1095                1100

Leu Leu His Leu Met Gly Met
1105                1110

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligomer primers"

(xi) SEQUENCE DESCRIPTION: SEQ ID NO: 16:

GAGCGCAGAG TGAGAACCAC                                          20

(2) INFORMATION FOR SEQ ID NO: 17:

(i) SEQUENCE CHARACTERISTICS:
        (A) LENGTH: 20 base pairs
```

(B) TYPE: nucleic acid
            (C) STRANDEDNESS: single
            (D) TOPOLOGY: linear (ii) MOLECULE TYPE: other nucleic acid
            (A) DESCRIPTION: /desc = "oligomer primers"

(xi) SEQUENCE DESCRIPTION: SEQ ID NO: 17:

ACTGTATTCT GCAGAGCTGC                                                    20

(2) INFORMATION FOR SEQ ID NO: 18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligomer primers"

(xi) SEQUENCE DESCRIPTION: SEQ ID NO: 18:

TTCCTTTCCCCTACCTTGTG                                                     20

(2) INFORMATION FOR SEQ ID NO: 19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "OLIGOMER PRIMER"

(xi) SEQUENCE DESCRIPTION: SEQ ID NO: 19:

TGTGGAAGCCTGGCAGACAT                                                     20

(2) INFORMATION FOR SEQ ID NO: 20:

(i) SEQUENCE CHARACTERISTICS:
            (A) LENGTH: 720 amino acids
            (B) TYPE: amino acid
            (D) TOPOLOGY: linear (ii) MOLECULE TYPE: protein (xi) SEQUENCE DESCRIPTION: SEQ ID NO: 20:

Ala Gly Thr Cys Thr Thr Thr Ala Thr Ala Gly Gly Gly Ala Gly Gly
1               5                   10                  15

Thr Thr Gly Gly Cys Cys Ala Gly Thr Cys Ala Ala Thr Ala Gly Gly
                20                  25                  30

Thr Thr Ala Cys Thr Thr Thr Ala Thr Gly Ala Gly Thr Thr Gly Cys
            35                  40                  45

Thr Ala Ala Cys Cys Cys Thr Gly Gly Thr Gly Ala Gly Cys Ala Gly
        50                  55                  60

Gly Ala Ala Gly Thr Thr Ala Thr Gly Thr Gly Gly Ala Cys Cys Ala
65                  70                  75                  80

Gly Gly Ala Gly Ala Gly Ala Ala Ala Cys Cys Thr Thr Gly Gly
                85                  90                  95

Thr Thr Cys Ala Gly Cys Cys Thr Gly Gly Ala Gly Ala Ala Ala Gly
                100                 105                 110

Gly Ala Gly Ala Gly Gly Thr Thr Gly Ala Cys Cys Cys Thr Ala Ala
            115                 120                 125

-continued

Ala Cys Thr Gly Gly Ala Gly Gly Gly Thr Gly Gly Ala Gly Ala Gly
    130                 135                 140

Gly Ala Cys Cys Cys Thr Gly Thr Thr Gly Thr Gly Ala Cys Thr Cys
145                 150                 155                 160

Thr Cys Cys Gly Ala Cys Thr Gly Ala Cys Thr Thr Gly Thr Cys Thr
                165                 170                 175

Thr Cys Cys Thr Thr Gly Ala Thr Gly Thr Cys Cys Thr Thr Thr Ala
            180                 185                 190

Ala Gly Cys Cys Gly Gly Ala Gly Cys Thr Gly Ala Thr Thr Cys Gly
        195                 200                 205

Gly Gly Cys Thr Gly Cys Thr Gly Cys Cys Thr Thr Ala Thr Thr Thr
    210                 215                 220

Cys Thr Gly Ala Gly Thr Thr Ala Gly Cys Gly Cys Thr Cys Thr Thr
225                 230                 235                 240

Ala Ala Gly Ala Thr Thr Gly Gly Gly Cys Cys Thr Cys Cys Cys Ala
                245                 250                 255

Gly Thr Thr Thr Gly Ala Gly Gly Ala Ala Gly Gly Gly Gly Cys Gly
            260                 265                 270

Gly Gly Cys Thr Gly Cys Thr Gly Thr Cys Thr Ala Cys Cys Thr Cys
        275                 280                 285

Thr Gly Thr Gly Ala Ala Thr Cys Thr Gly Cys Cys Cys Thr Gly Gly
    290                 295                 300

Ala Cys Cys Ala Cys Cys Cys Cys Gly Gly Gly Ala Gly Ala Gly Ala
305                 310                 315                 320

Ala Gly Gly Ala Gly Gly Gly Cys Thr Cys Cys Gly Gly Gly Gly Ala
                325                 330                 335

Ala Thr Cys Thr Cys Gly Cys Ala Cys Ala Thr Thr Cys Cys Ala Gly
            340                 345                 350

Gly Cys Ala Ala Ala Gly Gly Cys Thr Cys Cys Cys Gly Gly Gly Cys
        355                 360                 365

Cys Gly Cys Ala Gly Cys Cys Thr Cys Thr Gly Thr Gly Cys Cys Ala
    370                 375                 380

Cys Ala Cys Cys Cys Thr Thr Gly Gly Cys Cys Cys Gly Gly Gly Cys
385                 390                 395                 400

Cys Ala Gly Gly Thr Gly Thr Gly Cys Gly Cys Cys Cys Thr Cys Cys
                405                 410                 415

Thr Cys Gly Cys Thr Gly Cys Gly Ala Gly Gly Gly Gly Gly Ala Gly
            420                 425                 430

Cys Gly Gly Gly Cys Gly Gly Cys Thr Gly Cys Gly Gly Gly Gly Ala
        435                 440                 445

Gly Cys Gly Ala Thr Thr Thr Thr Cys Cys Ala Gly Cys Cys Cys Gly
    450                 455                 460

Gly Thr Thr Thr Gly Thr Gly Cys Thr Cys Thr Gly Thr Gly Thr Gly
465                 470                 475                 480

Thr Thr Thr Gly Thr Cys Thr Gly Cys Cys Thr Cys Thr Gly Gly Ala
                485                 490                 495

Gly Gly Gly Cys Thr Gly Gly Gly Thr Cys Cys Thr Cys Cys Thr Thr
            500                 505                 510

Ala Thr Thr Cys Ala Cys Ala Gly Gly Thr Gly Ala Gly Thr Cys Ala
        515                 520                 525

Cys Ala Cys Cys Cys Thr Gly Ala Ala Ala Cys Ala Cys Ala Gly Gly
    530                 535                 540

Cys Thr Cys Thr Cys Thr Thr Cys Cys Thr Gly Thr Cys Ala Gly Gly

```
                                  -continued
545                 550                 555                 560
Ala Cys Thr Gly Ala Gly Thr Cys Ala Gly Gly Thr Ala Gly Ala Ala
                565                 570                 575
Gly Ala Gly Thr Cys Gly Ala Thr Ala Ala Ala Cys Cys Ala Cys
                580                 585                 590
Cys Thr Gly Ala Thr Cys Ala Ala Gly Gly Ala Ala Ala Gly Gly
            595                 600                 605
Ala Ala Gly Gly Cys Ala Cys Ala Gly Cys Gly Gly Ala Gly Cys Gly
        610                 615                 620
Cys Ala Gly Ala Gly Thr Gly Ala Gly Ala Ala Cys Cys Ala Cys Cys
625                 630                 635                 640
Ala Ala Cys Cys Gly Ala Gly Gly Cys Gly Cys Cys Gly Gly Gly Cys
                645                 650                 655
Ala Gly Cys Gly Ala Cys Cys Cys Thr Gly Cys Ala Gly Cys Gly
                660                 665                 670
Gly Ala Gly Ala Cys Ala Gly Ala Gly Ala Cys Thr Gly Ala Gly Cys
            675                 680                 685
Gly Gly Cys Cys Cys Gly Gly Cys Ala Cys Cys Gly Cys Cys Ala Thr
        690                 695                 700
Gly Cys Cys Thr Gly Cys Gly Cys Thr Cys Thr Gly Gly Cys Thr Gly
705                 710                 715                 720
```